(12) United States Patent
Bjornson et al.

(10) Patent No.: US 8,658,365 B2
(45) Date of Patent: *Feb. 25, 2014

(54) NUCLEIC ACID SYNTHESIS COMPOSITIONS AND METHODS AND SYSTEMS FOR USING SAME

(75) Inventors: Keith Bjornson, Newark, CA (US); Harold Ray Lee, Sunnyvale, CA (US); Jonas Korlach, Newark, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 240 days.

This patent is subject to a terminal disclaimer.

(21) Appl. No.: 12/537,130

(22) Filed: Aug. 6, 2009

(65) Prior Publication Data

US 2010/0047802 A1 Feb. 25, 2010

Related U.S. Application Data

(63) Continuation of application No. 12/414,191, filed on Mar. 30, 2009, now Pat. No. 8,133,672.

(60) Provisional application No. 61/139,287, filed on Dec. 19, 2008, provisional application No. 61/072,645, filed on Mar. 31, 2008, provisional application No. 61/094,843, filed on Sep. 5, 2008.

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC ........ 435/6.12; 435/91.2; 536/23.1; 536/24.3

(58) Field of Classification Search
None
See application file for complete search history.

(56) References Cited

U.S. PATENT DOCUMENTS

| | | |
|---|---|---|
| 5,001,050 A | 3/1991 | Blanco et al. |
| 5,409,811 A | 4/1995 | Tabor et al. |
| 6,165,765 A | 12/2000 | Hong et al. |
| 6,399,320 B1 | 6/2002 | Markau et al. |
| 6,399,335 B1 | 6/2002 | Kao et al. |
| 6,447,724 B1 | 9/2002 | Jensen et al. |
| 6,610,486 B1 | 8/2003 | Dahlhauser |
| 6,762,048 B2 | 7/2004 | Williams et al. |
| 6,787,308 B2 | 9/2004 | Balasubramanian et al. |
| 6,917,726 B2 | 7/2005 | Levene et al. |
| 6,936,702 B2 | 8/2005 | Williams et al. |

(Continued)

FOREIGN PATENT DOCUMENTS

| | | |
|---|---|---|
| WO | 02088088 A2 | 10/2002 |
| WO | 2007075987 A2 | 7/2007 |

(Continued)

OTHER PUBLICATIONS

Rechkunova, N. I. et al., Biochemistry (Moscow), vol. 65, pp. 609-614 (2000).*

(Continued)

*Primary Examiner* — Teresa E Strzelecka
(74) *Attorney, Agent, or Firm* — Robert H. Reamey

(57) ABSTRACT

The Application relates to compositions, kits, methods, and systems for nucleotide sequencing comprising producing polymerase reactions that comprise both catalytic and non-catalytic divalent metal ions. Effective ratios and amounts of catalytic and non-catalytic divalent metal ions are described.

10 Claims, 24 Drawing Sheets

(56) References Cited

U.S. PATENT DOCUMENTS

| | | | |
|---|---|---|---|
| 7,041,812 | B2 | 5/2006 | Kumar et al. |
| 7,057,026 | B2 | 6/2006 | Barnes et al. |
| 7,315,019 | B2 | 1/2008 | Turner et al. |
| 2006/0051807 | A1 | 3/2006 | Fuller |
| 2006/0063173 | A1 | 3/2006 | Williams et al. |
| 2007/0036511 | A1 | 2/2007 | Lundquist et al. |
| 2007/0077564 | A1 | 4/2007 | Roitman et al. |
| 2007/0188750 | A1 | 8/2007 | Lundquist et al. |
| 2007/0196846 | A1 | 8/2007 | Hanzel et al. |
| 2007/0206187 | A1 | 9/2007 | Lundquist et al. |
| 2008/0030628 | A1 | 2/2008 | Lundquist et al. |
| 2008/0108082 | A1 | 5/2008 | Rank et al. |
| 2008/0212960 | A1 | 9/2008 | Lundquist et al. |
| 2008/0299565 | A1 | 12/2008 | Schneider et al. |
| 2009/0029385 | A1 | 1/2009 | Christians et al. |

FOREIGN PATENT DOCUMENTS

| | | |
|---|---|---|
| WO | 2007076057 A2 | 7/2007 |
| WO | 2007137060 A2 | 11/2007 |
| WO | WO2007123763 | 11/2007 |
| WO | 2008051530 A2 | 5/2008 |
| WO | 2008154317 A1 | 12/2008 |
| WO | 2009102470 A1 | 8/2009 |
| WO | 2009145828 A2 | 12/2009 |

OTHER PUBLICATIONS

Esteban, J.A. et al., Biochemistry, vol. 31, pp. 350-359 (1992).*
Slatko, B.E. et al., Current Prot. Mol. Biol., Suppl. 47, pp. 7.4.A.1-7.4.A.39 (1999).*
U.S. Appl. No. 12/384,112, filed Mar. 30, 2009, Clark, et al.
U.S. Appl. No. 12/383,855, filed Sep. 24, 2008, Patel, et al.
U.S. Appl. No. 61/094,843, filed Sep. 5, 2008, Travers, et al.
Zhou, et al., "Kinetic Analysis of Sequential Multistep Reactions", J. Phys. Chem. B, 2007, 111, pp. 13600-13610.
Miyake, et al., "Real-Time Imaging of Single-Molecule Fluorescence with a Zero-Mode Waveguide for the Analysis of Protein-Protein Interaction", Analytical Chemistry, 2008, 80(15), pp. 6018-6022.
Castro, et al., "Two proton transfers in the transition state for nucleotidyl transfer catalyzed by RNA and DNA-dependent RNA and DNA polymerases", PNAS, 104(11) pp. 4267-4272, (2007).
Paul M. Lundquist, et al., "Parallel confocal detection of single molecules in real time", Optics Letters, vol. 33, (2008), pp. 1026-1028.
Korlach, et al., "Long, Processive Enzymatic DNA Synthesis Using 100% Dye-Labeled Terminal Phosphate-Linked Nucleotides, Nucleosides, Nucleotides and Nucleic Acids", 27: pp. 1072-1083, (2008).
Korlach, et al., "Selective aluminum passivation for targeted immobilization of single DNA polymerase molecules in zero-mode waveguide nanostructures", PNAS 105(4): pp. 1176-1181 (2008).
Levene, et a., "Zero-Mode Waveguides for Single-Molecule Analysis at High Concentrations", Science 299, pp. 682-686, Jan. 2003.
Eid, et al., "Real-Time DNA Sequencing from Single Polymerase Molecules", Science, 323(5910), pp. 133-138 (2009).
Xie, S., et al., "Single-Molecule Enzymology", J. Biol. Chem., vol. 274, No. 23, Issue of Jun. 4, pp. 15967-15970, (1999).
Arndt, et al., Insight into the Catalytic Mechanism of DNA Polymerase β: Structures of Intermediate Complexes, Biochemistry, (2001), 40, pp. 5368-5375.
Soengas, et al., EMBO (1992) 11(11): pp. 4227-4237.
Tang, et al., "Mismatched dNTP Incorporation by DNA Polymerase β does not Proceed via Globally Different Conformational Pathways", Nucleic Acids Research, 36(9) pp. 2948-2957, 2008.
Bakhtina, et al., "Use of Viscogens, dNTPaS, and Rhodium (III) as Probes in Stopped-Flow Experiments to Obtain New Evidence for the Mechanism of Catalysis by DNA Polymerase", Vo. 44, No. 13, pp. 5177-5187, Biochemistry, 2005.
Arnold, J.J. et al. "Polivirus RNA-dependent RNA poiymerase(3pol): pre-steady-state kinetic analysis of ribonucleotide incorporation in the presence of Mn2+" Biochem (2004) 43(18):5138-5148.
Berman et al. "Structures of phi29 polymerase complexes with substrate: the mechanism of translocation in polymerases" EMBO J (2007) 26;3494-3605.
Blanco et al. "Mutational analysis of bacteriophage phi29 DNA polymerase" Meth in Enzyun (1995).
Blasco at al. "phi29 DNA polymerase active site" J Biol Chem (1993) 268(22):16763-16770.
Nicholson et al. "Enhanced protein themnostability from designed mutations that interact with alpha-helix dipoles" Nature (1988) 336:651-656.
Rechkunova, N.I. et al. "Thermostable DNA polymerase from Thermus thermophilus B35: influence of divalent metal ions on the interaction with deoxynucleoside triohosphates" Biochem (2000) 65(5):609-614.
Tock. M.R. et al. "Dynamic evidence for metal ion catalysis in the reaction mediated by a flap endonuclease" EMBO J. (2003) 22(5):995-1004.
Truniger et al. "A positively charged residue of phi29 DNA polymerase, highly conserved in DNA polymerases from families A and B, is involved in binding the incoming nucleotide" Nuc Acids Res (2002) 30(7):1483-1894.
ISR and Written Opinion dated Dec. 1, 2009 for related case PCT/US2009/002003.
IPRP dated Oct. 14, 2010 for related case PCT/US2009/002003.
ISR and Written Opinion dated Apr. 19, 2010 for related case PCT/US2009/004993.
IPRP dated Mar. 17, 2011 for related case PCT/US2009/004983.
EP Search Report dated Mar. 23, 2011 for related case EP 09755191.5.
International Search Report and Written Opinion dated Jan. 29, 2010 for related case PCT/US2009/001974.
International Preliminary Report on Patentability dated Oct. 14, 2010 for related case PCT/US2009/001974.
EP Search Report dated Aug. 12, 2011 for related case EP 09755183.2.
International Search Report and Written Opinion dated Aug. 31, 2011 for related case PCT/US2010/002659.
First Examination Report dated Apr. 24, 2012 for related case EP 09755191.5.

* cited by examiner

5'-ctg act gca tct aga cgt gac tga
   gac tga cgt aga tct gca ctg act gac tga

NUCLEIC ACID SYNTHESIS COMPOSITIONS AND METHODS AND SYSTEMS FOR USING SAME

CROSS-REFERENCE TO RELATED APPLICATIONS

This application is a Continuation Patent Application from U.S. patent application Ser. No. 12/414,191, filed March 30, which claims priority to U.S. Provisional Patent Application No. 61/072,645, filed Mar. 31, 2008, U.S. Provisional Patent Application No. 61/094,843, filed Sep. 5, 2008, and U.S. Provisional Patent Application No. 61/139,287, filed Dec. 19, 2008, the full disclosures of which are incorporated herein by reference in their entirety for all purposes.

BACKGROUND OF THE INVENTION

The ability to read the genetic code has opened countless opportunities to benefit humankind. Whether it involves the improvement of food crops and livestock used for food, the identification of the causes of disease, the generation of targeted therapeutic methods and compositions, or simply the better understanding of what makes us who we are, a fundamental understanding of the blueprints of life is an integral and necessary component.

A variety of techniques and processes have been developed to obtain genetic information, including broad genetic profiling or identifying patterns of discrete markers in genetic codes and nucleotide level sequencing of entire genomes. With respect to determination of genetic sequences, while techniques have been developed to read, at the nucleotide level, a genetic sequence, such methods can be time-consuming and extremely costly.

Approaches have been developed to sequence genetic material with improved speed and reduced costs. Many of these methods rely upon the identification of nucleotides being incorporated by a polymerization enzyme during a template sequence-dependent nucleic acid synthesis reaction. In particular, by identifying nucleotides incorporated against a complementary template nucleic acid strand, one can identify the sequence of nucleotides in the template strand. A variety of such methods have been previously described. These methods include iterative processes where individual nucleotides are added one at a time, washed to remove free, unincorporated nucleotides, identified, and washed again to remove any terminator groups and labeling components before an additional nucleotide is added. Still other methods employ the "real-time" detection of incorporation events, where the act of incorporation gives rise to a signaling event that can be detected. In particularly elegant methods, labeling components are coupled to portions of the nucleotides that are removed during the incorporation event, eliminating any need to remove such labeling components before the next nucleotide is added (See, e.g., Eid, J. et al., Science, 323(5910), 133-138 (2009)).

In any of the enzyme mediated template-dependent processes, the overall fidelity, processivity and/or accuracy of the incorporation process can have direct impacts on the sequence identification process, e.g., lower accuracy may require multiple fold coverage to identify the sequence with a high level of confidence.

The present invention provides methods, systems and compositions that provide for increased performance of such polymerization based sequencing methods, among other benefits.

BRIEF SUMMARY OF THE INVENTION

The present invention is generally directed to enzyme reactions, and in particular, nucleic acid synthesis compositions, systems, and methods that exhibit kinetic mechanisms having two or more kinetically observable reaction steps within an observable phase of the polymerase reaction. Such systems can be useful for observing the activity of a polymerase enzyme in real-time, for example, for carrying out single-molecule nucleic acid sequencing. We have discovered that a system in which the reaction kinetics exhibit two or more rate-limiting, kinetically observable (slow) steps within an observable phase reduce the relative number of short, difficult to detect pulses, resulting in more observable sequencing events, and allowing for a more accurate determination of a nucleic acid sequence.

In single-molecule DNA sequencing by synthesis, for example as described Eid. J. et al. Science, 323(5910), 133-138 (2009), the incorporation of specific nucleotides can be determined by observing bright phases and dark phases which correspond, for example, to reaction steps in which a fluorescent label is associated with the polymerase enzyme, and steps in which the fluorescent label is not associated with the enzyme. In some embodiments of the invention, the polymerase reaction system will exhibit two slow (kinetically observable) reaction steps wherein each of the steps is in a bright phase. In some embodiments of the invention, the system will exhibit two kinetically observable reaction steps wherein each of the steps is in a dark phase. In some cases, the system will have four kinetically observable (slow) reaction steps, two slow steps in a bright phase and two slow steps in a dark phase.

Obtaining a system with kinetically observable reaction steps can involve selection and/or production of 1) the type of polymerase enzyme, 2) the polymerase reaction conditions, including the type and levels of cofactors, and 3) the reaction substrates. We describe herein ways in which each of these aspects can be controlled in order to obtain a reaction system with two slow steps within an observable phase of the polymerase reaction.

In one aspect, the invention provides a method for nucleotide sequencing comprising: providing a reaction mixture having: (i) a polymerase enzyme, (ii) polymerase reaction conditions including cofactors, and (iii) polymerase reaction substrates including a primed template and nucleotides, such that a reaction comprising incorporation of the nucleotides into a growing nucleic acid occurs; and observing the reaction mixture to determine the incorporation of nucleotides into the growing nucleic acid; wherein at least one of the polymerase enzyme, the polymerase reaction conditions, or the polymerase reaction substrates are selected such that the reaction exhibits two kinetically observable steps within an observable phase of the polymerase reaction.

In some embodiments the two kinetically observable steps are each steps which proceed in a bright phase. In some embodiments the two kinetically observable steps are each steps which proceed in a dark phase. In some embodiments the reaction exhibits two kinetically observable steps which proceed in a bright phase, and two kinetically observable steps which proceed in a dark phase.

In some embodiments the two kinetically observable steps are selected from a group consisting of enzyme isomerization, nucleotide incorporation, and product release. In some embodiments two kinetically observable steps are template translocation and nucleotide binding.

In some embodiments the ratio of the rate constants of the kinetically observable steps is from 10:1 to 1:10. In some embodiments the ratio of the rate constants of the kinetically observable steps is from 5:1 to 1:5. In some embodiments the ratio of the rate constants of the kinetically observable steps is from 2:1 to 1:2.

In some embodiments the rate constant for one of the kinetically observable steps is less than about 100 per second. In some embodiments the rate constant for one of the kinetically observable steps is between about 0.1 per second and about 60 per second. In some embodiments the rate constant for one of the kinetically observable steps is between about 1 per second and about 20 per second. In some embodiments the reaction exhibits more than two kinetically observable steps.

In some embodiments the polymerase enzyme comprises a modified recombinant Φ29-type polymerase. In some embodiments the polymerase enzyme comprises a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. In some embodiments the polymerase enzyme comprises a modified recombinant DNA polymerase having at least one amino acid substitution or combination of substitutions selected from the group consisting of: an amino acid substitution at position 484, an amino acid substitution at position 198, and an amino acid substitution at position 381. In some embodiments the polymerase enzyme comprises a modified recombinant DNA polymerase having at least one amino acid substitution or combination of substitutions selected from the group consisting of E375Y, K512Y, T368F, A484E, A484Y, N387L, T379Q, T372L, K478Y, I370W, F198W, and L381A.

In some embodiments the polymerase reaction conditions comprise one or more of metal cofactor concentration, pH, temperature, an enzyme activity modulator, D2O, an organic solvent, and buffer. In some embodiments the polymerase reaction conditions comprise a mixture of divalent metal ions comprising at least one catalytic metal ion and at least one non-catalytic metal ion. In some embodiments the catalytic metal is selected from $Mg^{2+}$, $Mn^{2+}$ and mixtures thereof, and the non-catalytic metal is selected from $Ca^{2+}$, $Zn^{2+}$, $Co^{2+}$, $Ni^{2+}$, $Eu^{2+}$, $Sr^{2+}$, $Ba^{2+}$, $Fe^{2+}$, $Eu^{2+}$ and mixtures thereof. In some embodiments a ratio of catalytic metal to non-catalytic metal in the reaction mixture is from about 10:1 to about 1:10.

In some embodiments the polymerase reaction conditions comprise the presence of D2O. In some embodiments the D2O/H2O volume ratio in the reaction mixture is about 0.1 to about 2. In some embodiments the D2O/H2O volume ratio in the reaction mixture is about 0.2 to about 0.5. In some embodiments the D2O/H2O volume ratio in the reaction mixture is about 0.2 to about 0.3.

In some embodiments the conditions comprise an organic solvent selected from the group consisting of ethanol, methanol, THF, dioxane, DMA, DMF, and DMSO. In some embodiments the solvent comprises DMA. In some embodiments the solvent comprises DMSO.

In some embodiments the polymerase conditions comprise an additive that when added, changes the polymerase enzyme kinetics relative to a reaction having no additive. In some embodiments the additive is a thiol containing amino acid. In some embodiments the additive is L-cysteine.

In some embodiments one or more of the nucleotides comprise an optical label. In some embodiments one or more of the nucleotides comprise tetra, penta, or hexaphosphate groups having fluorescent labels linked to the terminal phosphate. In some embodiments the nucleotide comprises one, two, or three non-bridging thiol groups in its polyphosphate portion. In some embodiments the nucleotide has one non-bridging thiol. In some embodiments substantially only one chiral isomer is used.

In some embodiments the polymerase substrate that is selected such that the reaction exhibits two kinetically observable steps comprises a modified primer-template nucleotide complex.

In some embodiments at least two of the polymerase enzyme, the polymerase reaction conditions, or the polymerase reaction substrates are selected such that the reaction exhibits two kinetically observable steps.

In some embodiments all of the polymerase enzyme, the polymerase reaction conditions, or the polymerase reaction substrates are selected such that the reaction exhibits two kinetically observable steps.

In another aspect, the invention provides compositions useful for nucleotide sequencing comprising: a reaction mixture having (i) a polymerase enzyme, (ii) polymerase reaction conditions including cofactors, and (iii) reaction substrates including a primed template nucleotide and nucleotides, wherein at least one of the polymerase enzyme, the polymerase reaction conditions, or the polymerase reaction substrates are selected such that the reaction resulting in the incorporation of the nucleotides or nucleotide analogs exhibits two kinetically observable steps.

In another aspect, the invention provides systems for single-molecule nucleotide sequencing comprising: a zero-mode waveguide having, within its core, a reaction mixture comprising (i) a polymerase enzyme, (ii) polymerase reaction conditions including cofactors, and (iii) polymerase reaction substrates including nucleotides or nucleotide analogs and a primed template nucleotide wherein one or more of the polymerase reaction substrates is labeled with an optically observable label; and an optical detection system to detect the optically observable label to measure the sequential incorporation of nucleotides into a growing nucleic acid; wherein at least one of the polymerase enzyme, the polymerase reaction conditions, or the polymerase reaction substrates are selected such that the incorporation of the nucleotides or nucleotide analogs exhibits two kinetically observable steps within an observable phase of the polymerase reaction.

In some embodiments the system comprises an array of zero-mode waveguides.

In another aspect, the invention provides a method for identifying a polymerase reaction system having two or more kinetically observable steps within an observable phase of the polymerase reaction comprising: selecting a first polymerase reaction mixture comprising: (i) a polymerase enzyme, (ii) polymerase reaction conditions including cofactors, and (iii) polymerase reaction substrates including nucleotides or nucleotide analogs and a primed template nucleotide such that a polymerase reaction occurs; observing the polymerase reaction progress over a time period; and fitting the observed reaction progress over time in step (b) to a model to determine if the reaction shows two or more kinetically observable steps within an observable phase of the polymerase reaction.

In some embodiments the method is carried out in stop-flow apparatus.

In another aspect, the invention provides a method of sequencing a nucleic acid, comprising:

providing a complex comprising a polymerase enzyme, a template nucleic acid, and a primer sequence complementary to at least a portion of the template nucleic acid; contacting the complex with a reaction mixture that comprises a mixture of divalent metal ions comprising at least one catalytic metal ion and at least one non-catalytic metal ion, and one or more types of nucleotides or nucleotide analogs; and detecting incorporation of one or more of the nucleotide into the complex.

In some embodiments the catalytic metal is selected from $Mg^{2+}$, $Mn^{2+}$ and mixtures thereof and the non-catalytic metal is selected from $Ca^{2+}$, $Zn^{2+}$, $Co^{2+}$, $Ni^{2+}$, $Eu^{2+}$, $Sr^{2+}$, $Ba^{2+}$, $Fe^{2+}$, $Eu^{2+}$ and mixtures thereof. In some embodiments the catalytic metal comprises $Mn^{2+}$ and the non-catalytic metal comprises $Ca^{2+}$. In some embodiments a ratio of catalytic metal to non-catalytic metal in the reaction mixture is from about 10:1 to about 1:10. In some embodiments a ratio of catalytic metal to non-catalytic metal in the reaction mixture is from about 10:1 to about 1:5. In some embodiments a ratio of catalytic metal to non-catalytic metal in the reaction mixture is from about 5:1 to about 1:1. In some embodiments a ratio of catalytic metal to non-catalytic metal in the reaction mixture is from about 2.5:1 to about 1.5:1. In some embodiments the catalytic metal and non-catalytic metal are present in the reaction mixture at a total concentration of from about 0.1 mM to about 10 mM.

In some embodiments the detecting step comprises detecting incorporation of nucleotides in real-time as they are incorporated into the complex. In some embodiments the complex is immobilized on a solid support. In some embodiments the complex is immobilized on a solid support in an individually optically resolvable configuration.

In another aspect, the invention provides a method of sequencing a nucleic acid, comprising: providing a complex comprising a polymerase enzyme, a template nucleic acid, and a primer sequence complementary to at least a portion of the template nucleic acid; contacting the complex with a reaction mixture that comprises a plurality of types of nucleotides, and a mixture of divalent metal ions comprising at least one catalytic metal ion and at least one non-catalytic metal ion at first and second concentrations, respectively, wherein the mixture of divalent metal ions is selected to provide improved sequencing accuracy over a complex exposed to the first concentration of the catalytic metal in the absence of the non-catalytic metal; and detecting incorporation of a nucleotide into the complex.

In another aspect, the invention provides a composition, comprising: a complex comprising a template nucleic acid, a primer sequence and a polymerase enzyme; a mixture of divalent metal ions comprising at least one catalytic metal ion and at least one non-catalytic metal ion; and at least a first incorporatable nucleotide or nucleotide analog.

In another aspect, the invention provides method of modulating a polymerase activity, comprising: sequestering a bound nucleotide in a non-exchangeable state with a polymerase enzyme by contacting the polymerase enzyme with a first non-catalytic exchangeable co-factor; and contacting the polymerase enzyme with a catalytic exchangeable co-factor to exchange the non-catalytic co-factor, rendering the bound nucleotide into an exchangeable state with the polymerase enzyme.

In another aspect, the invention provides a kit, comprising: one or more components of a nucleic acid synthesis complex, selected from a DNA polymerase enzyme and a primer sequence; a reaction buffer comprising a mixture of catalytic metal ions and non-catalytic metal ions; a plurality of types of fluorescently labeled nucleotide analogs; and instructions for carrying out a sequence by synthesis reaction.

DETAILED DESCRIPTION OF THE INVENTION

Figure 1:
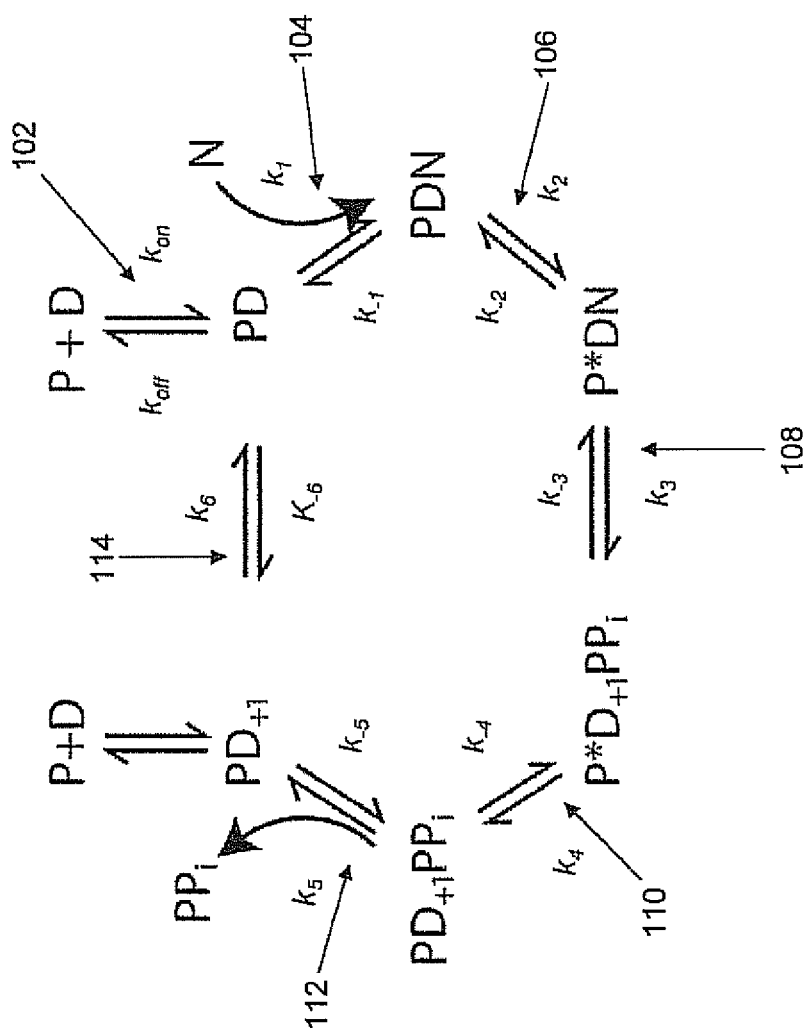
FIG. 1 is a schematic illustration of the reaction cycle for polymerase-mediated nucleic acid primer extension.

The present invention is generally directed to improved enzyme reaction compositions, methods, and systems that exhibit kinetic mechanisms having two or more slow, kinetically observable, or partially rate-limiting reaction steps within an observable phase of the polymerase reaction. Such systems can be useful for example, in single-molecule, real-time observations of such enzyme activity, which rely, at least in part, on detecting and identifying the enzyme reaction as it is occurring. By designing the reaction system to have two or more partially rate-limiting steps, the relative number of short, difficult to detect, events can be lowered. Enzymatic reactions often occur at rates that can far exceed the speed of a variety of detection systems, e.g., optical detectors. As such, by providing two or more partially rate-limiting steps within a phase of an enzyme reaction, one improves the ability to monitor that reaction using optical detection systems.

One particular exemplary system includes compositions for carrying out single-molecule DNA sequencing. We describe systems that exhibit two slow steps within an observable phase. An observable phase will generally have a time period during which the phase is observable. The time period for a bright phase, for example, can be represented by the pulse width. The time period for a dark phase can be represented, for example, by the interpulse distance. The length of each time period will not be the same for each nucleotide addition, resulting in a distribution of the length of the time periods. In some cases, the time periods with the shortest length will not be detected, leading to errors, for example in single-molecule sequencing. We have found that by designing enzyme systems such as polymerase reaction systems in which there are two slow, or kinetically observable, steps within an observable phase, the relative number of short, unobservable, time periods can be reduced, resulting in a higher proportion of observable sequencing events, and allowing for a more accurate determination of nucleotide sequence. As used herein, an observable phase includes phases that are not directly observable, but can be ascertained by measurements of other, related phases. For example, the lengths of dark phases can be observed by measuring the times between optical pulses corresponding to a related bright optical phase. Also as described herein, a phase which is dark under some labeling conditions can be bright under other labeling conditions.

While primarily described in terms of nucleic acid polymerases, and particularly DNA polymerases, it will be appreciated that the approach of providing multiple slow, or kinetically observable steps, within an enzyme system is applicable to other enzyme systems where one may wish to directly observe the enzyme reaction, in real time. Such enzyme systems include, for example, other synthesizing enzymes, e.g., RNA polymerases, reverse transcriptases, ribosomal polymerases, as well as other enzyme systems, such as kinases, phosphatases, proteases, nucleases, ligases, and the like.

I. Polymerase-Mediated Synthesis

In natural polymerase-mediated nucleic acid synthesis, a complex is formed between a polymerase enzyme, a template nucleic acid sequence, and a priming sequence that serves as the point of initiation of the synthetic process. During synthesis, the polymerase samples nucleotide monomers from the reaction mix to determine their complementarity to the next base in the template sequence. When the sampled base is complementary to the next base, it is incorporated into the growing nascent strand. This process continues along the length of the template sequence to effectively duplicate that template. Although described in a simplified schematic fashion, the actual biochemical process of incorporation is relatively complex.

The process can be described as a sequence of steps, wherein each step can be characterized as having a particular forward and reverse reaction rate that can be represented by a rate constant. One representation of the incorporation biochemistry is provided in FIG. 1. It is to be understood that the scheme shown in FIG. 1 does not provide a unique representation of the process. In some cases, the process can be described using fewer steps. For example, the process is sometimes represented without inclusion of the enzyme isomerization steps 106 and 110. Alternatively, the process can be represented by including additional steps such as cofactor binding. Generally, steps which can be slow, and thus limit the rate of reaction will tend to be included. The present invention relates to methods, systems, and compositions in which the polymerization reaction has two or more slow steps within certain phases of the polymerase reaction. Various schemes can be used to represent a reaction having two slow steps that may have more or fewer identified steps. In some cases the two or more slow steps are consecutive. In some cases, there can be intervening fast steps between the two or more slow steps.

As shown in FIG. 1, the synthesis process begins with the binding of the primed nucleic acid template (D) to the polymerase (P) at step 102. Nucleotide (N) binding with the complex occurs at step 104. Step 106 represents the isomerization of the polymerase from the open to closed configuration. Step 108 is the chemistry step where the nucleotide is incorporated into the growing strand of the nucleic acid being synthesized. At step 110, polymerase isomerization occurs from the closed to the open position. The polyphosphate component that is cleaved upon incorporation is released from the complex at step 112. The polymerase then translocates on the template at step 114. As shown, the various steps can include reversible paths and may be characterized by the reaction constants shown in FIG. 1 where:

$k_{on}/k_{off}$=DNA binding/release;
$k_1/k_{-1}$=nucleotide binding/release;
$k_2/k_{-2}$=polymerase isomerization (open/closed);
$k_3/k_{-3}$=nucleotide incorporation (chemistry);
$k_4/k_{-4}$=polymerase isomerization (closed/open);
$k_5/k_{-5}$=polyphosphate release/binding;
$k_6/k_{-6}$=polymerase translocation.

Thus, during steps 104 through 110, the nucleotide is retained within the overall complex, and during steps 104 and 106, reversal of the reaction step will yield an unproductive event, i.e., not resulting in incorporation. For example, a bound nucleotide at step 104 may be released regardless of whether it is the correct nucleotide for incorporation.

By selecting the appropriate polymerase enzyme, polymerase reaction conditions, and polymerase substrates, the absolute and relative rates of the various steps can be controlled. We have found that controlling the reaction such that the reaction exhibits two or more kinetically observable, or slow steps can produce a nucleic acid polymerization reaction in which the incorporation of the nucleotides can be observed more accurately. These characteristics are particularly useful for sequencing applications, and in particular single-molecule DNA sequencing.

In some cases, the invention involves a process having two or more kinetically observable steps that comprise steps after nucleotide binding through the step of product release. For the mechanism shown in FIG. 1, this would be, for example, any of steps 106, 108, 110, and 112. In some cases, steps 108 (nucleotide incorporation) and 112 (product release) are the two slow, or kinetically observable steps. As noted previously, where one desires systems with slow steps in a dark phase, the invention may involve a process having two or more slow steps that comprise the steps after product release through nucleotide binding. For the mechanism shown in FIG. 1, this would include steps 114 and 104.

In some cases, the invention involves a process in which there are two or more slow steps in two different observable phases within the polymerization, for example, two slow steps in a bright phase and two slow steps in a dark phase. For example, this could include a system having two slow steps in the steps after nucleotide binding through product release, and two slow steps for the steps after product release through nucleotide binding.

As is described herein, producing a process in which there are two or more slow steps in these portions of the polymerase reaction can result in a higher proportion of detectable enzyme states which can be useful, for example, to observe the sequential incorporation of nucleotides for nucleotide sequencing.

By the term slow-step we generally mean a kinetically observable step or partially rat-limiting step. The slow step need not be slow in the absolute sense, but will be relatively slow as compared with other steps in the enzymatic reaction. The slow, or kinetically observable steps, can be, for example, each partially rate-limiting, in that the rate of the step has a measurable effect on the kinetics of the enzymatic reaction. An enzymatic process, such as nucleic acid polymerization, can have both slower, kinetically observable steps and faster steps which can be so fast that they have no measurable effect on the kinetics, or rate, of the reaction. In some reactions, there can be a single rate-limiting step. For such reactions, the kinetics can be characterized by the rate of that single step. Other reactions will not have a single rate-limiting step, but will have two or more steps which are close enough in rate such that the characteristics of each will contribute to the kinetics of the reaction. A kinetically observable step is generally a step which is slow enough relative to the other steps in the reaction such that it can be experimentally ascertained. The experimental identification of a kinetically observable step can be done by the methods described herein, or by methods for assessing the kinetics of chemical and enzymatic reactions known in the art. For the current invention, the slow, or kinetically observable steps, need not be the slowest step or the rate-limiting step of the reaction. For example, a process of the current invention can involve a reaction in which step 104, nucleotide addition is the slowest (rate-limiting) step, while two or more of steps 106, 108, 110, or 112 are each kinetically observable.

As used herein, the term rate, as applied to the steps of a reaction can refer to the average rate of reaction. For example, when observing a single-molecule reaction, there will generally be variations in the rates as each individual nucleotide is added to a growing nucleic acid. In such cases the rate of the reaction can be represented by observing a number of individual events, and combining the rates, for example, by obtaining an average of the rates.

As used herein, the reference to the rate of a step or rate constant for a step can refer to the forward reaction rate of the polymerase reaction. As is generally understood in the art, reaction steps can be characterized as having forward and reverse rate constants. For example, for step 108, $k_3$ represents the forward rate constant, and $k_{-3}$ represents the reverse rate constant for the nucleotide incorporation. Some reaction steps, such as step 108, constitute steps which would be expected to be first order steps. Other steps, such as the forward reaction of step 104, with rate constant $k_2$, would be expected to be second order rate constants. For the purposes of the invention, for comparing the rate or the rate constant of a first order to a second order step, the second order rate constant $k_2$ can be treated as a pseudo-first order rate constant with the value $[N]*k_2$ where the concentration of nucleotide [N] is known.

It is generally desirable that the kinetically observable steps of the invention have rate constants that are lower than about 1000 per second. In some cases, the rate constants are lower than about 500 per second, lower than about 200 per second, lower than about 100 per second, lower than about 60 per second, lower than about 50 per second, lower than about 30 per second, lower than about 20 per second, lower than about 10 per second, lower than about 5 per second, lower than about 2 per second, or lower than about 1 per second.

In some embodiments the slowest of the two or more kinetically observable steps has a rate constant when measured under single-molecule conditions of between about 500 to about 0.1 per second, about 200 to about 0.1 per second, about 60 to about 0.5 per second, about 30 per second to about 2 per second, or about 10 to about 3 per second.

The ratio of the rate constants of each the two or more slow steps is generally greater than 1:10, in some cases the ratio of the rate constants is about 1:5, in some cases the ratio of the rate constants is about 1:2, in some cases, the ratio of rate constants is about 1:1. The ratio of the rate constants can be between about 1:10 and about 1:1, between about 1:5 and about 1:1, or between about 1:2 and about 1:1.

In some cases it is useful to consider the two slow-step system in terms of rates rather than rate constants. It is generally desirable that the kinetically observable steps of the invention have rates that are lower than about 1000 molecules per second when the reactions are carried out under single-molecule conditions. In some cases, the rates are lower than about 500 molecules per second, lower than about 200 molecules per second, lower than about 100 molecules per second, lower than about 60 molecules per second, lower than about 50 molecules per second, lower than about 30 molecules per second, lower than about 20 molecules per second, lower than about 10 molecules per second, lower than about 5 molecules per second, lower than about 2 molecules per second, or lower than about 1 molecule per second.

In some embodiments the slowest of the two or more kinetically observable steps has a rate when measured under single-molecule conditions of between about 500 to about 0.01 molecules per second, between about 200 to about 0.1 molecules per second, between about 60 to about 0.5 molecules per second, about 30 molecules per second to about 2 molecules per second, or about 10 to about 3 molecules per second.

The ratio of the rates of each the two or more slow steps is generally greater than 1:10, in some cases the ratio of the rates is about 1:5, in some cases the ratio of the rates is about 1:2, in some cases, the ratio of rates is about 1:1. The ratio can be between about 1:10 and about 1:1, between about 1:5 and about 1:1, or between about 1:2 and about 1:1.

A two or more slow-step system of the present invention can be obtained by selecting the correct set of polymerase enzyme, polymerase reaction conditions, and polymerase reaction substrates.

II. Sequencing by Incorporation

For sequencing processes that rely upon monitoring of the incorporation of nucleotides into growing nascent strands being synthesized by the complex, the progress of the reaction through these steps is of significant importance. In particular, for certain "real-time" nucleotide incorporation monitoring processes, the detectability of the incorporation event is improved based upon the amount of time the nucleotide is incorporated into and retained within the synthesis complex during its ultimate incorporation into a primer extension product.

By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al., Science 299:682-686, January 2003, and Eid, J. et al., Science, 323(5910), 133-138 (2009), the full disclosures of which are incorporated herein by reference in their entirety for all purposes.

Figure 2:
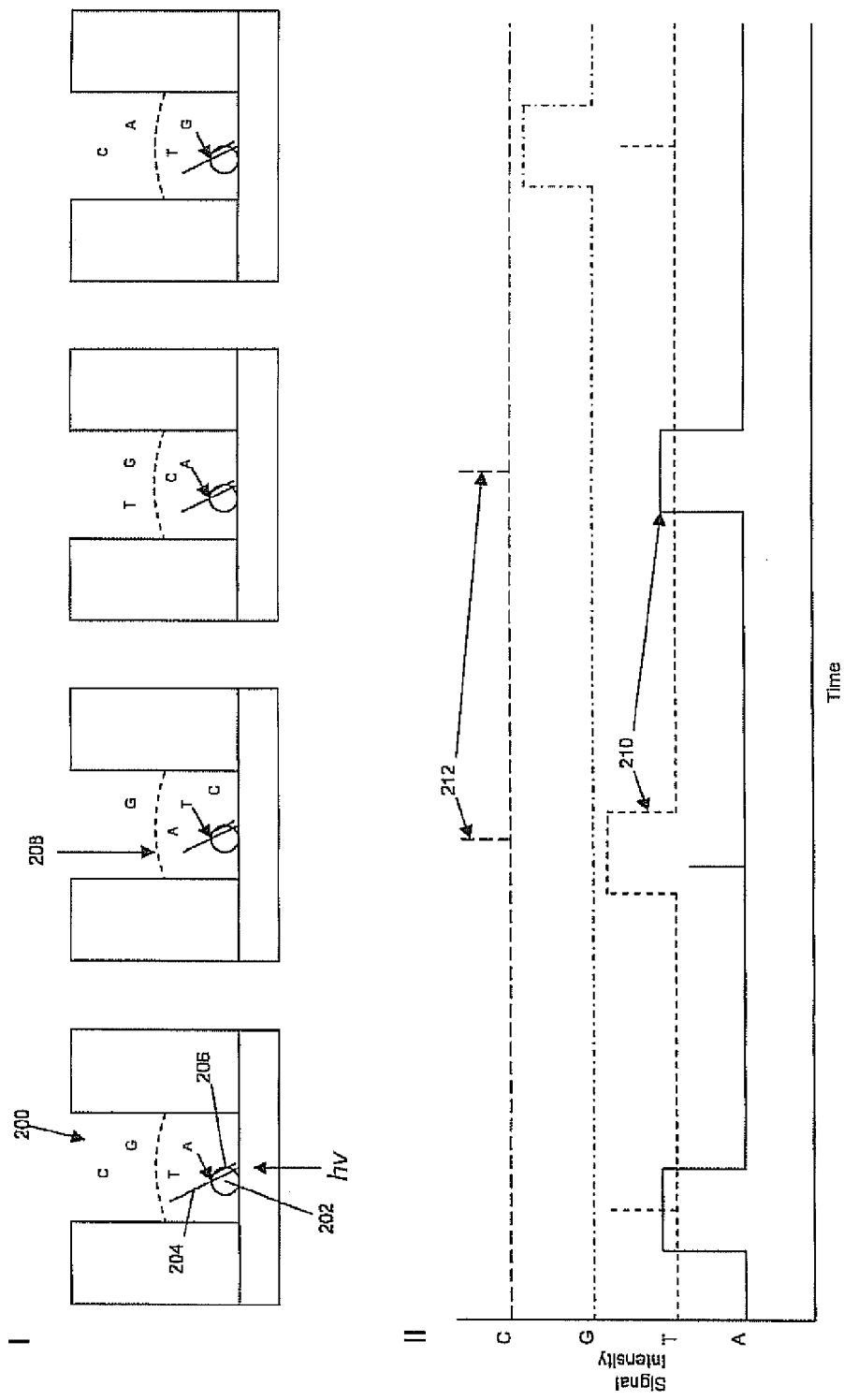
FIG. 2 schematically illustrates an exemplar single-molecule sequencing-by-incorporation process in which the compositions of the invention provide particular advantages.

In the first exemplary technique, as schematically illustrated in FIG. 2, a nucleic acid synthesis complex, including a polymerase enzyme 202, a template sequence 204 and a complementary primer sequence 206, is provided immobilized within an observation region 200, that permits illumination (as shown by hv) and observation of a small volume that includes the complex without excessive illumination of the surrounding volume (as illustrated by dashed line 208). By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume.

In particular, as shown in panel II of FIG. 2, when a nucleotide, e.g., A, is incorporated into by the polymerase, it is retained within the observation volume for a prolonged period of time, and upon continued illumination yields a prolonged fluorescent signal (shown by peak 210). By comparison, randomly diffusing and not incorporated nucleotides remain within the observation volume for much shorter periods of time, and thus produce only transient signals (such as peak 212), many of which go undetected, due to their extremely short duration.

In particularly preferred exemplary systems, the confined illumination volume is provided through the use of arrays of optically confined apertures termed zero-mode waveguides, e.g., as shown by confined reaction region 100 (ZMWs) (See, e.g., U.S. Pat. No. 6,917,726, which is incorporated herein by reference in its entirety for all purposes). For sequencing applications, the DNA polymerase is provided immobilized upon the bottom of the ZMW (See, e.g., Korlach et al., PNAS U.S.A. 105(4): 1176-1181. (2008), which is incorporated herein by reference in its entirety for all purposes.

In operation, the fluorescently labeled nucleotides (shown as A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuses away from the complex following incorporation of the associated nucleotide, nor do such labels interfere with the incorporation event. See, e.g., Korlach et al., Nucleosides, Nucleotides and Nucleic Acids, 27:1072:1083, 2008.

In the second exemplary technique, the nucleotides to be incorporated are each provided with interactive labeling components that are interactive with other labeling components provided coupled to, or sufficiently near the polymerase (which labels are interchangeably referred to herein as "complex borne"). Upon incorporation, the nucleotide borne labeling component is brought into sufficient proximity to the complex-borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair or FRET pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal, e.g., quenched or otherwise indicative of energy transfer. Upon incorporation and cleavage of the terminal phosphate groups, e.g., bearing a donor fluorophore, the quenching or other energy transfer is removed and the resulting characteristic fluorescent signal of the donor is observable.

In exploiting the foregoing processes, where the incorporation reaction occurs too rapidly, it may result in the incorporation event not being detected, i.e., the event speed exceeds the detection speed of the monitoring system. The missed detection of incorporated nucleotides can lead to an increased rate of errors in sequence determination, as omissions in the real sequence. In order to mitigate the potential for missed pulses due to short reaction times, in one aspect, the current invention can result in increased reaction time for incorporations. An advantage of the methods, systems, and compositions that produce a two or more slow-step process is an increased frequency of longer, detectable, binding/incorporation events. This advantage may also be seen as an increased ratio of longer, detectable pulses to shorter, non-detectable pulses, where the pulses represent binding/incorporation events.

Single-molecule sequencing often involves the optical observation of the polymerase process during the process of nucleotide incorporation, for example observation of the enzyme-DNA complex. During this process, there are generally two or more observable phases. For example, where a terminal-phosphate labeled nucleotide is used, and the enzyme-DNA complex is observed, there is a bright phase during the steps where the label is incorporated with (bound to) the polymerase enzyme, and a dark phase where there label is not incorporated with the enzyme. For the purposes of this invention, both the dark phase and the bright phase are generally referred to as observable phases, because the characteristics of these phases can be observed.

Whether a phase of the polymerase reaction is bright or dark can depend, for example, upon how and where the components of the reaction are labeled, and also how the reaction is observed. For example, as described above, the phase of the polymerase reaction where the nucleotide is bound can be bright where the nucleotide is labeled on its terminal phosphate. However, where there is a quenching dye associated with the enzyme or template, the bound state may be quenched, and therefore be a dark phase. Analogously, in a ZMW, or other optically confined configuration, the release and diffusion away of the label-bearing terminal phosphate may result in a dark phase, whereas in other systems, the release of the terminal phosphate may be observable, and therefore constitute a bright phase.

For example, consider again the reaction scheme of FIG. 1 in the context of the sequencing by incorporation embodiment described above which utilizes nucleotides having labels on their terminal phosphates. For this system, intermediates PDN, P*DN, P*D$_{+1}$PP$_i$, and PD$_{+1}$PP$_i$ would all represent bright states of a bright phase because for each of these intermediates, the label is associated with the polymerase enzyme. In contrast, intermediates PD$_{+1}$ and PD correspond to dark states of a dark phase, because for these intermediates, no dye is associated with the polymerase enzyme. In one aspect of the invention, any two of the steps which proceed from a bright intermediate, e.g. steps 106, 108, 110, and 112 of FIG. 1 are slow. By having two or more bright steps that are partially rate-limiting, the relative number of pulses with a longer pulse width, and/or detectable incorporation events increases.

Another example of a polymerase reaction with distinct observable phases is one in which the nucleotide is labeled such that its label does not dissociated from the enzyme upon product release, for example where the nucleotide is labeled on the base or on the sugar moiety. Here, the phase in which the label is associated with the active site of the enzyme (bright or dark) may extend past product release until translocation. For this example, an observable phase may extend from nucleotide binding until translocation.

In addition, the systems of the present invention may have two or more different distinct bright phases, for example, phases that can be distinguished based on different colors, e.g. different fluorescent emission wavelengths in the different observable phases. For all of these cases, we have discovered that it can be advantageous to have more than one rate-limiting (kinetically observable) step within a phase. Having more than one rate-limiting step within a phase can result in a distribution of pulse widths having relatively fewer undetectable or poorly detectable short pulses.

Figure 3:
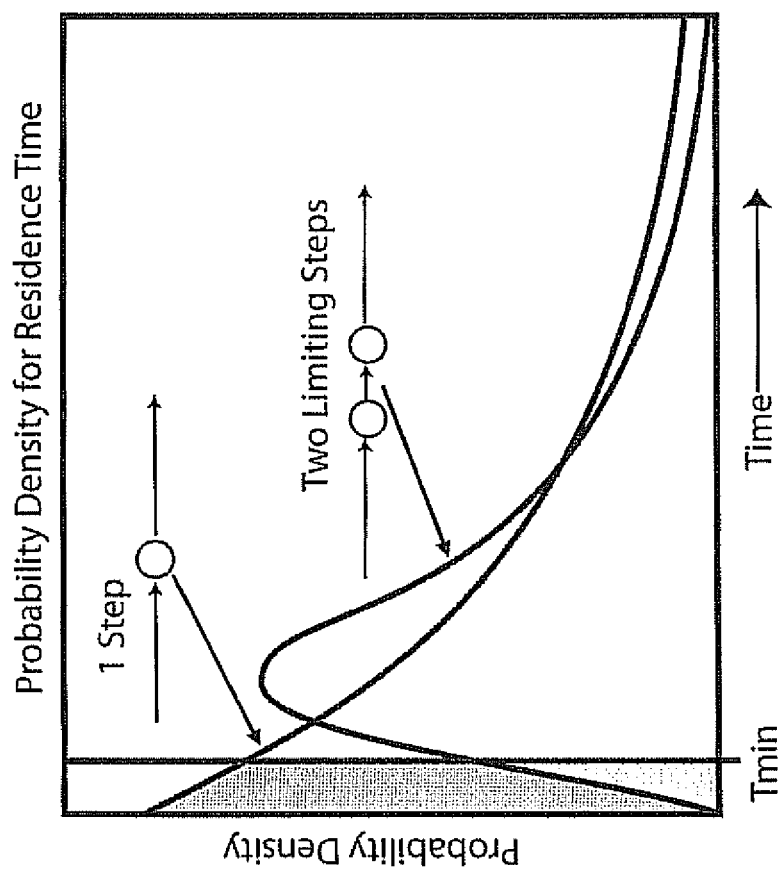
FIG. 3 shows a theoretical representation of the probability density for residence time for a polymerase reaction having 1 rate-limiting step or two rate-limiting steps within an observable phase.

While not being bound by theory, we provide the following theoretical basis for obtaining improved single-molecule sequencing results by using a system having two or more slow steps within an observable phase. While described here for nucleic acid polymerization, it will be appreciated that the two slow step systems of the invention can also be used for improved observation of other enzyme systems. A model for the effect of two slow steps on the probability density for residence time is described herein. FIG. 3 shows a plot of calculated probability density for residence time for cases in which (1) one step is rate-limiting and (2) two equivalent partially rate-limiting (slow) steps are present for the observable phase in which the nucleotide is associated with the enzyme.

For the case in which one step is rate-limiting, the probability distribution for the binding time can be represented by the single exponential equation:

$$y = A_0 e^{-kt} \quad \text{Eq. 1}$$

This represents the case in which, for example, incorporation of nucleotide into the growing nucleic acid (step 108 in FIG. 1) is the single slow step.

FIG. 3 illustrates that where one slow-step is present in this phase, there is an exponentially decreasing probability of a given residence time as the residence time increases, providing a distribution in which there is a relatively high probability that the residence time will be short.

For the case in which there are two slow steps in this phase, for example where both the incorporation step (step 108 in FIG. 1) and the release of product (PPi) step (step 112 in FIG. 1) are slow, the probability density versus residence time can be represented by a double exponential equation:

$$y = A_0 e^{-k_1 t} - B_0 e^{-k_2 t} \quad \text{Eq. 2}$$

FIG. 3 illustrates that for the case in where there are two slow steps, the probability of very fast residence times is relatively low as compared to the case having one slow step. In addition, the probability distribution for two slow steps exhibits a peak in the plot of probability density versus residence time. This type of residence time distribution can be advantageous for single-molecule sequencing where it is desired to measure a high proportion of binding events and where fast binding events may be unreliably detected.

Typically, for a given illumination/detection system there will be a minimum detection time below which events, such as binding events, will be unreliably detected or not detected at all. This minimum detection time can be attributed, for example, to the frame acquisition time or frame rate of the optical detector, for example, a CCD camera. A discussion of detection times and approaches to detection for these types of systems is provided in U.S. patent application Ser. No. 12/351,173 the full disclosures of which are incorporated herein by reference in their entirety for all purposes. FIG. 3 includes a line which indicates a point where the residence time equals a minimum detection time (Tmin). The area under the curve in the region below Tmin represents the population of short pulses which will not be accurately detected for this system. It can be seen from FIG. 3 that the relative proportion of binding times that fall below Tmin is significantly lower for the case in which the reaction exhibits two slow steps as compared to the case where the reaction exhibits one slow step.

Thus, as described above, one aspect of the invention relates to methods, systems, and compositions for performing nucleic acid sequencing with a nucleic acid synthesis reaction in which the reaction exhibits two or more slow steps within a bright phase. In addition, an aspect of the invention relates to nucleic acid synthesis reactions having two or more slow states wherein each of the slow steps proceeds from a state in which the labeled component is associated with the polymerase enzyme.

In some embodiments of the invention, the two or more slow steps are within a dark phase. In some cases the two or more slow steps proceed from states in which the labeled component is not associated with the enzyme. Having two or more slow states that proceed from a dark intermediate can be advantageous, for example, for lowering the frequency of events having a very short dark state or having a very short interpulse distance. The advantage of this type of system can be demonstrated by again considering FIG. 1 in the context of the sequencing by incorporation embodiment described above which utilizes nucleotides having labels on their terminal phosphates. In this system, intermediates $PD_{+1}$ and PD can correspond to dark states within a dark phase, for example in a ZMW, because for these intermediates, no dye is associated with the polymerase enzyme.

The steps that comprise the two slow steps can include, for example, nucleotide addition, enzymatic isomerization such as to or from a closed state, cofactor binding or release, product release, incorporation of nucleic acid into the growing nucleic acid, or translocation.

(i) Determining Whether the Polymerase System Exhibits Two Slow Steps

In some cases the presence of two slow steps can be ascertained by the characteristics of the polymerase reaction run under single-molecule sequencing conditions, for example by measuring the distribution of pulse widths. For example, a distribution of pulse widths can be determined using systems described herein where the components of the system are labeled such that a bright state is observed during nucleotide binding, and a dark state is observed from after product release until the next nucleotide binding event. Under these conditions a bright pulse will be observed that corresponds to bound nucleotide. The width of the pulse corresponds to the amount of time that the nucleotide is bound. By measuring the width of a number of pulses, corresponding to a number of nucleotide incorporation events, a distribution of pulse widths can be obtained. From this distribution of pulse widths, in some cases, it can be determined that a polymerase reaction having two slow steps is occurring, and in particular, a polymerase reaction having two slow steps during the bright state during which the nucleotide is associated with the polymerase enzyme. The use of a distribution of pulses to determine a kinetic mechanism having two slow (kinetically observable) steps is described, for example, in Miyake et al. Analytical Chemistry 2008 80 (15), 6018-6022. The determination of the steps in a multistep reaction such as a polymerase reaction is described, for example, in Zhou, et al. J. Phys. Chem. B, 2007, 111, 13600-13610.

Analogously, the presence of two slow steps in the dark phase of a polymerase reaction can in some cases be detected by determining the distribution of the time between pulses (interpulse time). Where the system exhibits two slow steps, a distribution described by a double exponential can be seen.

In some cases, it is not possible or not practical to determine under single-molecule conditions whether a system is exhibiting two slow-step kinetics. For example, in some cases, the frame time of the detection optics will be slow enough that a significant number of pulses or interpulse times are not detected, precluding a reliable determination of pulse width or interpulse time distribution. In some cases, the short pulses are not detected because the short pulses generally have a smaller number of photons, making the pulses difficult to detect even were a short camera frame time is available. In such cases, the presence of two slow-step kinetics under such polymerase reaction conditions can be determined by running a reaction under substantially the same polymerase reaction conditions, but not under single-molecule conditions. For example, a reaction can be run under substantially the same polymerase reaction conditions as the single-molecule sequencing system, but with a higher concentration of polymerase enzyme and in some cases, a higher concentration of primer and/or template nucleotide. The reaction run under substantially the same polymerase reaction conditions, but with higher concentrations of polymerase enzyme, primer, and/or template can be used to determine whether the system shows two slow steps as described herein. The reaction to determine two slow-step kinetics may have labels on different components of the reaction than that for single-molecule sequencing, such as having labels on the template nucleic acid.

For example, a stopped-flow reaction such as described in the examples below can be used to determine whether the polymerase reaction conditions exhibit two slow steps. As described in the examples, stopped-flow experiments can be used to establish that the polymerase reaction is exhibiting two slow step kinetics either in a bright phase or in a dark phase for single-molecule sequencing.

A higher enzyme/primer/template concentration reaction such as a stopped-flow reaction can be used to identify systems having two slow steps for single-molecule sequencing. Alternatively, the reaction run under substantially the same conditions but higher concentration of enzyme/primer/template can be used to verify that a single-molecule sequencing system is being carried out under polymerase reaction conditions that exhibit two slow steps.

A. Polymerase Enzyme

One important aspect of obtaining a two slow-step system of the invention is selection of the enzyme that is used. The polymerase enzyme can be modified in a manner in which the relative rates of the steps of the polymerase reactions are changed such that the enzyme will be capable of showing two slow-step characteristics. Recombinant enzymes useful in the present invention are described, for example, in copending U.S. patent application Ser. No. 12/384,112 entitled "Generation of Modified Polymerases for Improved Accuracy in Single-molecule Sequencing", docket number 105-004901US, filed Mar. 30, 2009.

A modified polymerase (e.g., a modified recombinant Φ29-type DNA polymerase for example, a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase) that exhibits one or more slow steps optionally includes a mutation (e.g., an amino acid substitution or insertion) at one or more of positions 484, 249, 179, 198, 211, 255, 259, 360, 363, 365, 370, 372, 378, 381, 383, 387, 389, 393, 433, 478, 480, 514, 251, 371, 379, 380, 383, 458, 486, 101, 188, 189, 303, 313, 395, 414, 497, 500, 531, 532, 534, 558, 570, 572, 574, 64, 305, 392, 402, 422, 496, 529, 538, 555, 575, 254, 390, 372-397, and 507-514, where numbering of positions is relative to wild-type Φ29 polymerase. For example, relative to wild-type Φ29 a modified recombinant polymerase can include at least one amino acid substitution or combination of substitutions selected from the group consisting of: an amino acid substitution at position 484; an amino acid substitution at position 198; all amino acid substitution at position 381; an amino acid substitution at position 387 and an amino acid substitution at position 484; an amino acid substitution at position 372, an amino acid substitution at position 480, and an amino acid substitution at position 484; an amino acid substitution at position 372, an amino acid substitution at position 387, and an amino acid substitution at position 480; an amino acid substitution at position 372, an amino acid substitution at position 387, and an amino acid substitution at position 484; an amino acid substitution at position 372, an amino acid substitution at position 387, an amino acid substitution at position 478, and an amino acid substitution at position 484; A484E; A484Y; N387L; T372Q; T372Y; T372Y and K478Y; K478Y; I370W; F198W; L381A; T368F; A484E, E375Y, K512Y, and T368F; A484Y, E375Y, K512Y, and T368F; N387L, E375Y, K512Y, and T368F; T372Q, E375Y, K512Y and T368F; T372L, E375Y, K512Y, and T368F; T372Y, K478Y, E375Y, K512Y, and T368F; I370W, E375Y, K512Y, and T368F; F198W, E375Y, K512Y, and T368F; L381A, E375Y, K512Y, and T368F; and E375Y, K512Y, and T368F. A K512F substitution (or K512W, K512L, K512I, K512V, K512H, etc.) is optionally employed, e.g., where a K512Y substitution is listed herein. As another example, the modified polymerase can include an insertion of at least one amino acid (e.g., 1-7 amino acids, e.g., glycine) within residues 372-397 and/or 507-514. For example, a glycine residue can be introduced after residue 374, 375, 511, and/or 512 (designated as 374.1G, 375.1G, etc.). In some embodiments the enzyme has one or more of the amino acid substitutions E375Y K512Y, T368F, A484E, A484Y, N387L, T372Q, T372L, K478Y, I370W, F198W, and L381A.

A list of exemplary mutations and combinations thereof is provided in Table 1, and additional exemplary mutations are described herein. Essentially any of these mutations, or any combination thereof, can be introduced into a polymerase to produce a modified recombinant polymerase (e.g., into wild-type Φ29, an exonuclease deficient Φ29-type polymerase, and/or E375Y/K512Y/T368F Φ29, as just a few examples).

TABLE 1

| Mutation | Rationale |
| --- | --- |
| D249E | metal coordination |
| A484E | metal coordination |
| D249E/A484E | metal coordination |
| A484D | metal coordination |
| A484H | metal coordination |
| A484Y | metal coordination |
| D249E/A484D | metal coordination |
| D249E/A484H | metal coordination |
| D249E/A484Y | metal coordination |
| 374.1G/375.1A | dye interaction |
| 374.1Gins/375.1Gins | dye interaction |
| V514Y | dye interaction |
| V514F | dye interaction |
| 511.1G/K512Y/512.1G | dye interaction |
| T372H | closed conformation of fingers |
| T372V | closed conformation of fingers |
| T372I | closed conformation of fingers |
| T372F | closed conformation of fingers |
| T372Y | closed conformation of fingers |
| T372N | closed conformation of fingers |
| T372Q | closed conformation of fingers |
| T372L | closed conformation of fingers |
| T372L/K478Y | closed conformation of fingers |
| T372Y/K478Y | closed conformation of fingers |
| T372Y/K478L | closed conformation of fingers |
| K478Y | closed conformation of fingers |
| D365N | closed conformation of fingers |
| D365Q | closed conformation of fingers |
| L480H | closed conformation of fingers |
| L480F | closed conformation of fingers |
| L381A | closed conformation of finger and exo |
| I179A | closed conformation of finger and exo |
| I378A | closed conformation of finger and exo |
| I179A/L381A | closed conformation of finger and exo |
| I179A/I378A/L381A | closed conformation of finger and exo |
| I370A/I378A | closed conformation of finger and exo |
| I179A/I370A/I378A/L381A | closed conformation of finger and exo |
| I179W | closed conformation of finger and exo |
| I179H | closed conformation of finger and exo |
| F211A | closed conformation of finger and exo |
| F211W | closed conformation of finger and exo |
| F211H | closed conformation of finger and exo |
| F198A | closed conformation of finger and exo |
| F198W | closed conformation of finger and exo |
| F198H | closed conformation of finger and exo |
| P255A | closed conformation of finger and exo |
| P255W | closed conformation of finger and exo |
| P255H | closed conformation of finger and exo |
| Y259A | closed conformation of finger and exo |
| Y259W | closed conformation of finger and exo |
| Y259H | closed conformation of finger and exo |
| F360A | closed conformation of finger and exo |
| F360W | closed conformation of finger and exo |
| F360H | closed conformation of finger and exo |
| F363A | closed conformation of finger and exo |
| F363H | closed conformation of finger and exo |
| F363W | closed conformation of finger and exo |
| I370W | closed conformation of finger and exo |
| I370H | closed conformation of finger and exo |
| K371A | closed conformation of finger and exo |
| K371W | closed conformation of finger and exo |
| I378H | closed conformation of finger and exo |
| I378W | closed conformation of finger and exo |
| L381W | closed conformation of finger and exo |
| L381H | closed conformation of finger and exo |
| K383N | closed conformation of finger and exo |
| K383A | closed conformation of finger and exo |
| L389A | closed conformation of finger and exo |
| L389W | closed conformation of finger and exo |
| L389H | closed conformation of finger and exo |
| F393A | closed conformation of finger and exo |
| F393W | closed conformation of finger and exo |
| F393H | closed conformation of finger and exo |
| I433A | closed conformation of finger and exo |
| I433W | closed conformation of finger and exo |
| I433H | closed conformation of finger and exo |
| K383L | phosphate backbone interaction |
| K383H | phosphate backbone interaction |
| K383R | phosphate backbone interaction |
| Q380R | phosphate backbone interaction |
| Q380H | phosphate backbone interaction |
| Q380K | phosphate backbone interaction |
| K371L | phosphate backbone interaction |
| K371H | phosphate backbone interaction |
| K371R | phosphate backbone interaction |
| K379L | phosphate backbone interaction |
| K379H | phosphate backbone interaction |
| K379R | phosphate backbone interaction |
| E486A | phosphate backbone interaction |
| E486D | phosphate backbone interaction |
| N387L | incoming nucleotide base and translocation |
| N387F | incoming nucleotide base and translocation |
| N387V | incoming nucleotide base and translocation |
| N251H | phosphate interaction |
| N251Q | phosphate interaction |
| N251D | phosphate interaction |
| N251E | phosphate interaction |
| N251K | phosphate interaction |
| N251R | phosphate interaction |
| A484K | phosphate interaction |
| A484R | phosphate interaction |
| K383Q | phosphate interaction |
| K383N | phosphate interaction |
| K383T | phosphate interaction |
| K383S | phosphate interaction |
| K383A | phosphate interaction |
| I179H/I378H | closed conformation |
| I179W/I378W | closed conformation |
| I179Y/I378Y | closed conformation |
| K478L | |
| I378Y | |
| I370A | |
| I179Y | |
| N387L/A484E | |
| N387L/A484Y | |
| T372Q/N387L/A484E | |
| T372Q/N387L/A484Y | |
| T372L/N387L/A484E | |
| T372L/N387L/K478Y/A484Y | |
| T372Y/N387L/K478Y/A484E | |
| T372Y/N387L/K478Y/A484Y | |

Table 2 presents exemplary Φ29 mutants that can exhibit two slow step behavior under appropriate reaction conditions. The first three modified polymerases exhibit the most pronounced two slow step behavior, followed by the next six. As noted, the polymerases are optionally exonuclease-deficient; for example, they can also include an N62D substitution.

TABLE 2

A484E/E375Y/K512Y/T368F
A484Y/E375Y/K512Y/T368F
N387L/E375Y/K512Y/T368F
T372Q/E375Y/K512Y/T368F
T372L/E375Y/K512Y/T368F
T372Y/K478Y/E375Y/K512Y/T368F
I370W/E375Y/K512Y/T368F
F198W/E375Y/K512Y/T368F
L381A/E375Y/K512Y/T368F
E375Y/K512Y/T368F

Compositions, kits, and systems (e.g., sequencing systems) including the modified recombinant polymerases with decreased rate constants are features of the invention, as are methods employing the modified polymerases (e.g., methods of sequencing or making DNA). Methods for generating recombinant polymerases are also featured, as described in greater detail below, as are the resulting polymerases. Thus, one aspect provides a modified recombinant Φ29-type DNA polymerase comprising one or more mutations (e.g., amino acid substitutions or insertions) relative to a parental polymerase at one or more positions selected from the group consisting of: a) positions that form a binding site for a metal ion that interacts with an epsilon and/or digamma phosphate of a bound nucleotide analog having five or more phosphate groups; b) positions 372-397 and 507-514; c) positions that form a binding site for a terminal fluorophore on a phosphate-labeled nucleotide analog, particularly hexaphosphate analogs; d) positions at an intramolecular interface in a closed conformation of a ternary complex comprising the polymerase, a DNA, and a nucleotide or nucleotide analog; e) positions that form a binding site for a polyphosphate group of a bound nucleotide or nucleotide analog; f) positions that interact with the base of a bound nucleotide or nucleotide analog; and g) positions that interact with a bound DNA; wherein numbering of positions is relative to wild-type Φ29 polymerase. Preferably, the one or more mutations comprise at least one mutation other than a 514Y, 514W, 514F, 514I, 514K, 259S, 370V, 370K, 372D, 372E, 372R, 372K, 372N, 372L, 387A, 387D, 478D, 478E, 478R, 480K, 480M, 480R, 371Q, 379E, 379T, 486D, 486A, 188A, 188S, 254F, 254V, 254A, 390F, or 390A substitution. The modified polymerase optionally exhibits a decreased first rate constant, balanced first and second rate constants, and the like as for the embodiments described above.

A number of relevant positions and mutations are described herein. For example, the modified polymerase can comprise at least one amino acid substitution at at least one residue selected from the group consisting of positions 484, 249, 179, 198, 211, 255, 259, 360, 363, 365, 370, 372, 378, 381, 383, 387, 389, 393, 433, 478, 480, 514, 251, 371, 379, 380, 383, 458, 486, 101, 188, 189, 303, 313, 395, 414, 497, 500, 531, 532, 534, 558, 570, 572, 574, 64, 305, 392, 402, 422, 496, 529, 538, 555, 575, 254, and 390. Exemplary modified polymerases include those with at least one amino acid substitution or combination of substitutions selected from the group consisting of: an amino acid substitution at position 484; an amino acid substitution at position 198; an amino acid substitution at position 381; A484E; A484Y; N387L; T372Q; T372Y; T372Y and K478Y; K478Y; I370W; F198W; L381A; T368F; A484E, E375Y, K512Y, and T368F; A484Y, E375Y, K512Y, and T368F; N387L, E375Y, K512Y, and T368F; T372Q, E375Y, K512Y, and T368F; T372L, E375Y, K512Y, and T368F; T372Y, K478Y, E375Y, K512Y, and T368F; I370W, E375Y, K512Y, and T368F; F198W, E375Y, K512Y, and T368F; L381A, E375Y, K512Y, and T368F; and E375Y, K512Y, and T368F, as well as others described herein. As another example, the modified polymerase can include an insertion of at least one amino acid (e.g., 1-7 amino acids, e.g., glycine) within residues 372-397 and/or 507-514 (e.g., after residue 374, 375, 511, and/or 512).

The polymerase mutations and mutational strategies noted herein can be combined with each other and with essentially any other available mutations and mutational strategies to confer additional improvements in, e.g., nucleotide analog specificity, enzyme processivity, improved retention time of labeled nucleotides in polymerase-DNA-nucleotide complexes, and the like. For example, the mutations and mutational strategies herein can be combined with those taught in, e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al. This combination of mutations/mutational strategies can be used to impart several simultaneous improvements to a polymerase (e.g., decreased branch fraction formation, improved specificity, improved processivity, altered rates, improved retention time, improved stability of the closed complex, etc.). In addition, polymerases can be further modified for application-specific reasons, such as to improve activity of the enzyme when bound to a surface, as taught, e.g., in WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al., or to include purification or handling tags as is taught in the cited references and as is common in the art.

Specific mutations noted herein can be used alone or in combination with each other and/or with available mutations as described in the references noted above, or can be used in polymerases that lack such previously described mutations. As just one example, essentially any mutation or combination thereof noted herein can be introduced into an E375Y/K512Y/T368F Φ29 polymerase, optionally, an exonuclease-deficient E375Y/K512Y/T368F Φ29 polymerase.

For example, enzymological approaches have been reported for enhancing the reaction kinetics of the polymerization reaction (See, e.g., published U.S. Patent Application Nos. 2007-0196846 and 2008-0108082, and Provisional Patent Application 61/094,843, the full disclosures of which are incorporated herein by reference in their entirety for all purposes), to increase the residence time of an incorporating nucleotide in the active site of a polymerase. While such reactions yield improvements in detectability of a bound nucleotide, and thus, an incorporation event, for a number of circumstances, it has been shown that increasing the retention time of a nucleotide complexed with a polymerase, also results in an increased likelihood that the nucleotide will be released unproductively.

B. Polymerase Reaction Conditions

The polymerase reaction conditions can also be important for obtaining a two slow-step enzyme system. In particular, polymerase reaction conditions include components selected to produce two slow-step kinetics. The polymerase reaction conditions include the type and concentration of buffer, the pH of the reaction, the temperature, the type and concentration of salts, the presence of particular additives which influence the kinetics of the enzyme, and the type, concentration, and relative amounts of various cofactors, including metal cofactors. The term "polymerase reaction conditions" as used herein generally excludes the concentration of the polymerase enzyme or the concentration of the primer-template complex. Thus, two reactions are run under substantially the same polymerase reaction conditions where the first reaction has a small amount of polymerase enzyme, such as a single polymerase enzyme, and a small amount of primer template complex, such as a single primer-template complex associated with a single polymerase enzyme, and the second reaction has a higher concentration of polymerase enzyme, for example a concentration of polymerase enzyme of about 0.05 µM to 0.5 µM, and about 0.01 µM to about 0.1 µM.

It some embodiments the type and concentration of buffer are chosen in order to produce a reaction having two slow steps. Enzymatic reactions are often run in the presence of a buffer, which is used, in part, to control the pH of the reaction mixture. We have found that in some cases the type of buffer can influence the kinetics of the polymerase reaction in a way that can lead to two slow-step kinetics. For example, in some cases, we have found that the use of TRIS as buffer is useful for obtaining a two slow-step reaction. Buffers suitable for the invention include, for example, TAPS (3-{[tris(hydroxymethyl)methyl]amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the kinetics of the polymerase reaction, and can be used as one of the polymerase reaction conditions to obtain a reaction exhibiting two slow-step kinetics. The pH can be adjusted to a value that produces a two slow-step reaction mechanism. The pH is generally between about 6 and about 9. In some cases, the pH is between about 6.5 and about 8.0. In some cases, the pH is between about 6.5 and 7.5. In some cases, the pH is about 6.5, 6.6, 6.7, 6.8, 6.9, 7.0, 7.1, 7.2, 7.3, 7.4, or 7.5.

The temperature of the reaction can be adjusted in order to obtain a reaction exhibiting two slow-step kinetics. The reaction temperature may depend upon the type of polymerase which is employed. Temperatures between 15° C. and 90° C., between 20° C. and 50° C. between 20° C. and 40° C., or between 20° C. and 30° C. can be used.

In some cases, additives can be added to the reaction mixture that will change the kinetics of the polymerase reaction in a manner that can lead to two slow-step kinetics. In some cases, the additives can interact with the active site of the enzyme, acting for example as competitive inhibitors. In some cases, additives can interact with portions of the enzyme away from the active site in a manner that will change the kinetics of the reaction so as to produce a reaction exhibiting two slow steps. Additives that can influence the kinetics include, for example, competitive, but otherwise unreactive substrates or inhibitors in analytical reactions to modulate the rate of reaction as described in copending U.S. Utility patent application Ser. No. 12/370,472 the full disclosures of which is incorporated herein by reference in its entirety for all purposes.

One aspect of the invention is the use of a kinetic isotope effect, such as the addition of deuterium to the system in order to control the kinetics of the polymerase reaction in single-molecule sequencing. In some cases, the isotope, such as deuterium can be added to influence the rate of one or more step in the polymerase reaction for improving single-molecule sequencing. In some cases, the deuterium can be used to slow one or more steps in the polymerase reaction due to the deuterium isotope effect. By altering the kinetics of steps of the polymerase reaction, in some instances, two slow-step kinetics, as described herein, can be achieved. As described in the examples below, in some cases, the addition of deuterium can be used to increase the mean pulse width in a single-molecule sequencing system.

The substitution of deuterium for hydrogen in a chemical reaction such as the polymerase reaction can result in a change in the kinetics of the reaction. An isotopic substitution can significantly modify the reaction rate when the isotopic replacement is in a chemical bond that is broken or formed in the rate-limiting step. In such a case, the change is generally termed a primary isotope effect. When the substitution is not involved in the bond that is breaking or forming, a smaller rate change, generally termed a secondary isotope effect can be observed. The magnitude of the kinetic isotope effect has been used to elucidate reaction mechanisms. If other steps are partially rate-determining, the effect of isotopic substitution can be masked. The presence of a deuterium isotope effect for polymerase enzymes has been described in Castro et al., PNAS, 104(11), 4267-4272 (2007), the full disclosure of which is incorporated here by reference in its entirety for all purposes. We describe here the use of a kinetic isotope effect to control the kinetics of a polymerase reaction for single-molecule sequencing, for example to improve the accuracy of sequencing by influencing the characteristics of the light pulses which are measured. The deuterium isotope effect could be used, for example, to control the rate of incorporation of nucleotide, for example by slowing the incorporation rate.

The amount of deuterium isotope that is substituted for hydrogen can be used to control the characteristics of the reaction. For example, in some cases, the more deuterium that is added, the more of a rate effect on a given polymerase step can be obtained. In some cases, the deuterium is added to a readily exchangeable proton/deuterium position, such as to water, a hydroxyl or a carboxylic acid proton/deuterium. In these positions, the proton/deuterium in the system would be expected to rapidly exchange. In other cases, the deuterium could be added to a position that experiences less exchange, such as, for example, a carbon-hydrogen bond alpha to a hydroxyl group. In some cases, the use of a statistical mixture of $D_2O/H_2O$ is advantageous. For example, it allows one to change the incorporation rate and therefore the nucleotide residence time while keeping the other conditions of the polymerase reaction relatively unchanged. The volume percent of deuterium substituted for hydrogen can be, for example about 1, 2, 3, 4, 5, 7, 10, 15, 20, 25, 30, 40, 50, 60, 70, 75, 80, 90, 95, 99 percent or higher. In some cases, the amount of deuterium can be expressed as the percent of $D_2O$ out of the total $D_2O$ plus $H_2O$. In some cases, a range of D2O can be between about 1% and about 80%, between about 10% and about 60%, between about 20% and about 40%, or between about 20% and 30%. In some cases, adding a high level of deuterium can slow the reaction so as to diminish the yield of the polymerase reaction. The amount of deuterium can be controlled in order to improve the accuracy while retaining acceptable yield.

Other isotopes than deuterium can be used to control single-molecule sequencing. For example, isotopes of carbon (e.g. $^{13}C$), nitrogen, oxygen, sulfur, or phosphorous could also be used.

Additives that can be used to control the kinetics of the polymerase reaction include the addition of organic solvents. The solvent additives are generally water soluble organic solvents. The solvents need not be soluble at all concentrations, but are generally soluble at the amounts used to control the kinetics of the polymerase reaction. While not being bound by theory it is believed that the solvents call influence the three dimensional conformation of the polymerase enzyme which can affect the rates of the various steps in the polymerase reaction. For example, the solvents can provide affect steps involving conformational changes such as the isomerization steps shown in FIG. 1. Added solvents can also affect, and in some cases slow, the translocation step. The slowing of the translocation step can increase interpulse distances, and can be used in conjunction with slowing the nucleotide binding step, for example, to obtain two slow steps in the steps in which the nucleotide is not associated with the enzyme, for instance resulting in two slow steps in the dark phase of a polymerase reaction. In some cases, the solvent additives can increase the interpulse distance without substantially affecting the pulse widths in single-molecule sequencing. In some cases, the solvents act by influencing hydrogen bonding interactions. In some case, the addition of solvent can be used to change the rate of one or more steps in the polymerase reaction. For example, the solvent may slow one or more steps in the polymerase reaction. By influencing the rates of various steps of the polymerization, the solvent additives can be used, in some cases, to obtain two slow-step kinetics. The addition of organic solvents can be used, for example to increase the mean time between pulses (interpulse distance).

The water miscible organic solvents that can be used to control the rates of one or more steps of the polymerase reaction in single-molecule sequencing include alcohols, amines, amides, nitriles, sulfoxides, ethers, and esters and small molecules having more than one of these functional groups. Exemplary solvents include alcohols such as methanol, ethanol, propanol, isopropanol, glycerol, and small alcohols. The alcohols can have one, two, three, or more alcohol groups. Exemplary solvents include small molecule ethers such as tetrahydrofuran (THF), and dioxane. In some embodiments the solvent is dimethylacetamide (DMA). In some embodiments the solvent is dimethylsulfoxide (DMSO). In some embodiments, the solvent is dimethylformamide (DMF). In some embodiments the solvent is acetonitrile.

The water miscible organic solvent can be present in any amount sufficient to control the kinetics of the polymerase reaction. The solvents are generally added in an amount less than 40% of the solvent weight by weight or volume by volume. In some embodiments the solvents are added between about 0.1% and 30%, between about 1% and about 20%, between about 2% and about 15%, and between about 5% and 12%. The effective amount for controlling the kinetics can be determined by the methods described herein and those known in the art.

A suitable additive for obtaining a two slow-step system is the amino acid, cysteine, having the chemical formula $HO_2CCH(NH_2)CH_2SH$. Cysteine can be added to the reaction mixture as a salt, for example, as the hydrochloride salt. Generally, the naturally occurring L-cysteine (Cys) is used. Other additives with chemical structures related to cysteine can also be used. For example, homocysteine or any other suitable natural or artificial amino acid having an S atom, and in particular, a thiol group. We have found that the addition of cysteine can lead to an increase in both overall yield and in accuracy of single molecule sequencing. While not being bound by theory, Cys, because of its thiol side chain and AA polar moiety may have beneficial effects on both polymerase and nucleotides during sequencing. An increase in the pulse width with the addition of Cys has also been observed. The effect could be different from or cumulative to that of dithiothreitol (DTT), which can also be added to the sequencing reaction, owing to only a single-SH functionality in Cys and, therefore, larger tendency to participate in intermolecular interactions. In addition, Cys may influence the analog binding to polymerase via linking the two with hydrogen and S—S bonds. Cysteine can be added at any level suitable for improving the properties of the enzymatic reaction. For example, cysteine can be added at amounts greater than about 0.1 mM, greater than about 0.5 mM, greater than about 1 mM, greater than about 5 mM, greater than about 10 mM. In some cases, the cysteine can be added in amounts less than about 200 mM, less than about 100 mM, less than about 50 mM, less than about 20 mM, or less than about 10 mM. In some cases, the cysteine is present in amounts between about 1 mM and about 100 mM, between about 5 mM and about 50 mM, or between about 10 mM and about 30 mm.

Additives such as dithiothreitol (DTT), can also be present in the reaction. In some cases, such additives, which are often used in enzymatic systems, do not directly lead to two slow-step systems, but are useful for the functioning of the enzyme during, for example, nucleic acid synthesis.

One aspect of controlling the polymerase reaction conditions relates to the selection of the type, level, and relative amounts of cofactors. For example, during the course of the polymerase reaction, divalent metal co-factors, such as magnesium or manganese, will interact with the enzyme-substrate complex, playing a structural role in the definition of the active site. For a discussion of metal co-factor interaction in polymerase reactions, see, e.g., Arndt, et al., Biochemistry (2001) 40:5368-5375.

For example, and without being bound to any particular theory of operation, it is understood that metal cofactor binding in and around the active site serves to stabilize binding of incoming nucleotides and is required for subsequent catalysis, e.g., as shown in steps 106 and 108. Other metal cofactor binding sites in polymerases, e.g., in the exonuclease domains, are understood to contribute to different functionality of the overall proteins, such as exonuclease activity.

In the context of the present invention, however, it has been discovered that modulation, and particularly competitive modulation of divalent metal cofactors to the synthesis reaction can provide substantial benefits in terms of reaction kinetics without a consequent increase in negative reaction events.

In the synthesis reaction, certain divalent or trivalent metal cofactors, such as magnesium and manganese are known to interact with the polymerase to modulate the progress of the reaction (See, e.g., U.S. Pat. No. 5,409,811). Other divalent metal ions, such as $Ca^{2+}$, have been shown to interact with the polymerase, such as phi29 derived polymerases, to negative effect, e.g., to halt polymerization. As will be appreciated, depending upon the nature of the polymerization reaction, environmental conditions, the polymerase used, the nucleotides employed, etc., different metal co-factors will have widely varying catalytic effects upon the polymerization reaction. In the context of the present invention, different metal co-factors will be referred to herein based upon their relative catalytic impact on the polymerization reaction, as compared to a different metal included under the same reaction conditions. For purposes of discussion, a first metal co-factor that interacts with the polymerase complex to support the polymerization reaction to a higher level than a second metal co-factor under the same conditions is termed a "catalytic metal ion" or "catalytic metal". In preferred aspects, such catalytic metals support the continued, iterative or processive polymerization of nucleic acids under the particular polymerase reaction conditions, e.g., through the addition on multiple bases, while in some cases, a given type of metal cofactor may only support addition of a single base. Such metals may be sufficiently catalytic, depending upon the specific application.

In certain cases, particularly preferred divalent metal ions or catalytic metals, include, e.g., $Mn^{2+}$, and in some cases will include $Mg^{2+}$. Less preferred multivalent metal ions that may provide a sufficient level of catalytic activity depending upon the desired application include, e.g., zinc.

For purposes of the invention, metal ions that interact with the polymerase, but that do not promote the polymerization reaction, and in many cases act to arrest or prevent polymerization, are termed "non-catalytic metals". Included among the non-catalytic metals for various polymerase systems are calcium, barium, strontium, iron, cobalt, nickel, tin, zinc, and europium. For example, these metals can be added to the polymerization reaction in salt form such as $Sr(OAc)_2$, $Sr(OAc)_2$, $CoCl_2$, $SnCl_2$, $CaCl_2$, or $ZnSO_4$. As will be appreciated, a first metal co-factor that might be deemed to be catalytic under a first set of reaction conditions or relative to second metal co-factor, may be deemed to be a non-catalytic metal under another different set of reaction conditions, or with respect to a third metal co-factor. By way of example, as noted previously, magnesium is generally known to support DNA polymerization. However, under certain conditions, and/or relative to manganese, magnesium can operate as a non-catalytic co-factor. For purposes of the present invention, a catalytic co-factor will support polymerization to a greater degree than the non-catalytic metal under the same reaction conditions. The relative catalytic impact will typically be a function of the reactant turnover rate of the polymerization complex, with catalytic metal co-factors promoting a turnover that is at least 2×, more preferably at least 5×, still more preferably, at least 10×, and in some cases 20×, 50× or more than that of the non-catalytic metal co-factor under the same reaction conditions. Accordingly, in the context of various aspects of the invention, the polymerization complex is exposed to two different co-factors that have substantially different impacts on the polymerization reaction under the given set of reaction conditions, where the first metal co-factor promotes polymerization to a substantially greater degree than the second metal co-factor, or restated in the negative context, the second metal co-factor arrests or halts polymerization to a substantially greater degree than the first.

In particular, and without being bound to any particular theory of operation, it is believed that the presence of a non-catalytic metal in the polymerase complex, through binding in or around the active site, results in the inability for the synthesis reaction to proceed out of the complexed state. In particular, the presence of calcium ions has been shown to modulate both the forward progress of the polymerase reaction at step 106 and/or 108 (also shown as k2 and k3, respectively), as well as the reverse progress of the reaction at step 106 and/or 104 (also shown as k-2 and k-1, respectively). As a result, in the presence of calcium or other non-catalytic metals, the complexed nucleotide is effectively sequestered in the complex; unable to proceed forward to incorporation, or in reverse to the release of the unincorporated nucleotide, in an unproductive nucleotide binding event, to yield a free polymerase.

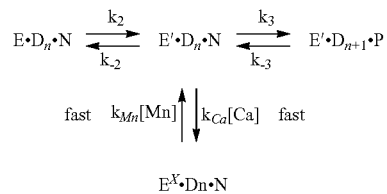

Such unproductive binding, and subsequent release of an otherwise correct nucleotide by a polymerization complex is referred to herein as "branching". For real-time sequence by incorporation processes, such branching can lead to incorrect repeat calls or insertion errors for a single base.

Because these non-catalytic metal ions interact with polymerase enzymes to promote the tight, non-exchangeable binding of nucleotides to polymerases, the use of such metals in polymerase based sequencing processes is counterintuitive. In particular, it would not be expected that the use of such non-catalytically competent metal ions would provide benefits in polymerase based sequencing processes, because they specifically interfere with the desired interaction.

Surprisingly however, it has been discovered that mixtures of both catalytic and non-catalytic metal ions in the polymerization reaction mixture yields surprisingly beneficial results in this process. In particular, it has been observed that the competitive exchange rate for catalytic and non-catalytic metal ions in nucleic acid polymerases is sufficiently fast, that one can exchange catalytic for non-catalytic ions in the reaction complex. Restated, upon exchange of the calcium ion with a catalytically more competent metal ion, e.g., manganese or magnesium, the polymerization reaction is again capable of proceeding forward to incorporation, or in reverse to release a bound nucleotide to return to the free polymerase state. Thus, these exchangeable catalytic and non-catalytic cofactors can be contacted with the polymerase complex to first sequester the nucleotide in a non-exchangeable state within the polymerase complex, from which it is substantially less likely to be released. Upon exchange of a non-catalytic cofactor with a catalytic co-factor, the nucleotide will be transitioned into an exchangeable state within the complex, from which it can proceed through an incorporation reaction. Further, the rate of the exchange is such that one can effectively modulate the speed of the polymerase reaction by modulating the relative proportion of catalytic/non-catalytic metal ions in the reaction mixture. In particular, modulating the relative concentrations of these ions effectively modulates the reaction kinetics of individual enzymes, rather than just in bulk. Furthermore, because the nature of the interaction of the complex with calcium ions interferes with both the forward progress of incorporation and the reverse progress of release or branching, one can effectively slow the reaction, or more specifically, increase the time the "to be incorporated" nucleotide is bound, without a consequent increase in the amount of nucleotide released or branching. In contrast, other approaches that have been exploited to increase the retention time of a nucleotide by a polymerase complex generally do so by slowing the kinetics of the forward reaction out of a given state, without concurrently slowing the reverse of the reaction into that state. Such methods include both enzymological approaches, as well as adjustment of the polymerase reaction conditions, e.g., temperature and pH, to slow the reaction. As such, the slowed forward progress of the reaction can result in a concurrent increase of the unproductive release of correct nucleotides for incorporation of similar magnitude.

Although generally described in terms of mixtures of a first and second metal co-factors, where the first has higher catalytic impact than the second, it will be appreciated that the reaction mixtures may include more than two metal co-factors of differing catalytic impact upon the polymerization complex. For example, the reaction mixtures may include three, four, five or more different metal co-factors that have differing catalytic impacts, i.e., promotion or inhibition of polymerization reaction under the given reaction conditions. Thus, in its broadest sense, the invention includes polymerization reaction mixtures that include mixtures of different metal co-factors that interact with the polymerization complex, where the different metal co-factors have different catalytic impacts upon the polymerization reaction, e.g., different effects on enzyme turnover rates, relative to each other. Such reaction mixtures can include two, three, four, five or more different metal co-factors that are capable of interacting with the polymerization complex, and particularly the polymerase itself, to promote or inhibit the polymerization reaction, relative to one or more other metal co-factors that are present.

In addition to the benefits of enhanced retention time without a substantial concurrent increase in branching, the presence of non-catalytic ions also provides additional advantages, such as increased ternary stability and reduced Km values. Further, the presence of such metals can provide an inhibitory effect on any exonuclease activity present in the reaction mixture, either as an activity of the polymerase enzyme, or otherwise. See FIGS. 9 and 10, and Soengas, et al., EMBO (1992) 11(11):4227-4237.

In an alternative aspect, the reaction rate of the polymerase may be modulated through the iterative modulation of catalytic and non-catalytic metals in the reaction mixture, rather than through the real-time modulation of metal ions in the complex. As a result, one can proceed, step wise, along the template sequence, monitoring the incorporation of nucleotides into the nascent strand.

In an exemplary operation, one introduces the four types of nucleotides, e.g., each labeled with a detectably different fluorophore on its terminal phosphate group or other portion of the nucleotide released upon incorporation, to the polymerase/template/primer complex that is immobilized upon a substrate, e.g., either in a spotted array format where all template/primers in a single spot represent the same sequence, or in a single-molecule observable configuration. The nucleotides are introduced along with a sufficient concentration of non-catalytic metal ions, e.g., $Ca^{2+}$, and without catalytic metal ions, e.g., $Mn^{2+}$. In the context of this reaction mixture, a cognate nucleotide (the correct nucleotide for incorporation into the nascent strand based upon the template), is bound by the polymerase which proceeds through the first portion of the incorporation reaction, e.g., through step 104 and/or 106 of FIG. 1. However, due to the presence of $Ca^{2+}$ and the lack of catalytic metals, the nucleotide is sequestered in the active site of the polymerase, unable to proceed to incorporation or be released from the complex. Excess labeled nucleotides are then washed from the complex, typically still in the presence of $Ca^{2+}$ ions. The remaining complex bound cognate nucleotides are then observed and identified based upon their fluorescent label, e.g., using a fluorescent microscope, array scanner, or the like.

Figure 11:
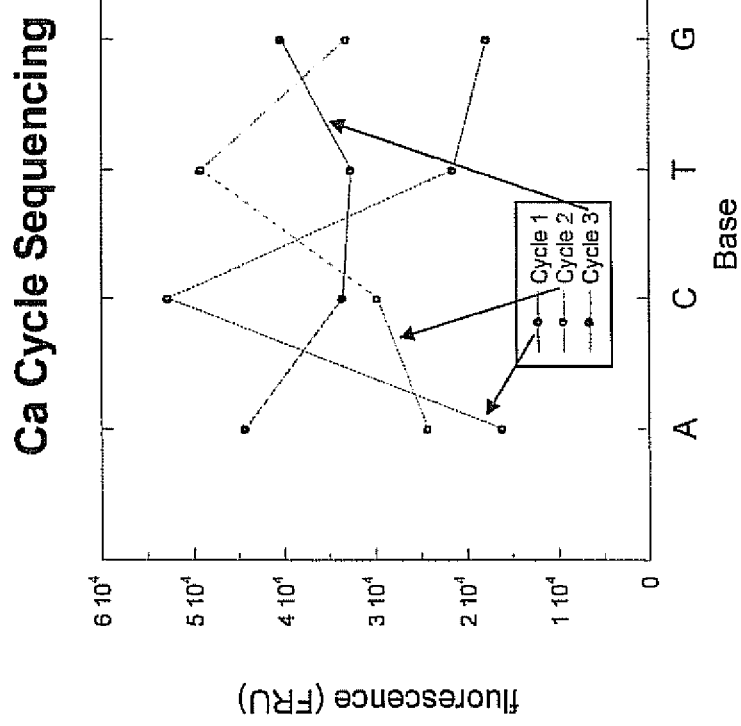
FIG. 11 shows data illustrating sequential incorporation of nucleotides in a polymerase-mediated, template-dependent primer extension reaction, where the reaction was iteratively initiated and arrested through the addition of catalytic and non-catalytic metal co-factors.

The complex is then allowed to proceed with incorporation of the nucleotide and consequent release of the label group by washing the complex with catalytic metal ions, e.g., $Mn^{2+}$ to allow incorporation to proceed, e.g., through step 108 of FIG. 1, resulting in a single base extended primer. The complex is then washed to remove catalytic metal ions from the complex and reaction mixture, and the process is repeated with a new wash of labeled nucleotides in a $Ca^{2+}$ containing buffer. See, for example, FIG. 11.

Accordingly, in one aspect, the present invention is directed to the use of a mixture of catalytic and non-catalytic metal ions in a nucleic acid synthesis reaction, to modulate the reaction kinetics of the complex. Thus, in at least one aspect, the invention is directed to nucleic acid synthesis reaction mixtures that include both catalytic and non-catalytic metals. The molar ratio of catalytic to non-catalytic metals in the reaction mixture will generally vary depending upon the type of kinetic modulation desired for a given synthesis reaction, where slower incorporation would suggest higher levels of non-catalytic metal ions. Typically, such ratios of catalytic to non-catalytic metals in the reaction mixture will vary from about 10:1 to about 1:10, and preferably, from about 10:1 to about 1:5, depending upon the desired level of modulation, the particular enzyme system employed, the catalytic and non-catalytic metal cofactors that are used, and the reaction conditions. In particularly preferred aspects, the ratios of catalytic to non-catalytic metals will be in the range of from about 5:1 to about 1:1, with ratios of from about 2.5:1 to about 1.5:1 being particularly preferred.

In addition to the presence of such metals at the ratios described herein, the absolute concentration of such metals in the reaction mixtures will typically range from about 0.05 mM to about 50 mM, in some cases from about 0.1 mM to about 10 mM, in some cases from about 0.1 mM to about 5 mM. The composition can include, for example, from about 0.1 mM $MnCl_2$ to about 1 mM $MnCl_2$ and from about 0.1 mM $CaCl_2$ to about 2 mM $CaCl_2$; or from about 0.2 mM $MnCl_2$ to about 1 mM $MnCl_2$ and from about 0.4 mM $CaCl_2$ to about 1.5 mM $CaCl_2$.

In addition to the catalytic and/or non-catalytic metal components, the compositions of the invention will typically include one or more of the other components of a nucleic acid synthesis reaction. In particular, such complexes typically will include one, and preferably more than one of the other various components for a nucleic acid synthesis reaction. Such components include, for example, a nucleic acid polymerizing enzyme. In preferred aspects, the nucleic acid polymerizing enzymes are selected from DNA polymerases, although RNA polymerases, reverse transcriptases, or the like are also envisioned. In the case of DNA polymerases, a variety of polymerases may be employed in the compositions of the invention, including for example, strand displacing polymerases, such as Phi29 derived polymerases (e.g., those described in U.S. Pat. No. 5,001,050, and published U.S. Patent Application No. 2007-0196846, the full disclosures of which are incorporated herein by reference in their entirety for all purposes), Taq polymerases, KOD polymerases, Klenow, 9° N polymerase, T7 DNA polymerase, *E. coli* pol I, *Bacillus stearothermophilus* pol I, DNA polymerases α, δ, ε, and γ, RB 69 polymerase, polIV (DINB), polV (UmuD'2C), and others.

C. Polymerase Reaction Substrates

The polymerase reactions of the invention include polymerase reaction substrates. The substrates that are selected can be selected to influence the kinetics of the polymerase reaction, and can be utilized to prepare a polymerase reaction system that exhibits two slow-step kinetics. The polymerase reaction substrates include the template nucleic acid, a primer, and one or more nucleotides. The template nucleic acid is the molecule for which the complimentary sequence is synthesized in the polymerase reaction. In some cases, the template nucleic acid is linear, in some cases, the template nucleic acid is circular. The template nucleic acid can be DNA, RNA, or can be a non-natural RNA analog or DNA analog. Any template nucleic acid that is suitable for replication by a polymerase enzyme can be used herein.

By "nucleic acid" or "oligonucleotide" or grammatical equivalents herein means at least two nucleotides covalently linked together. A nucleic acid of the present invention will generally contain phosphodiester bonds, although in some cases, nucleic acid analogs are included that may have alternate backbones, comprising, for example, phosphoramide, phosphorothioate, phosphorodithioate, and peptide nucleic acid backbones and linkages. Other analog nucleic acids include those with positive backbones; non-ionic backbones, and non-ribose backbones, including those described in U.S. Pat. Nos. 5,235,033 and 5,034,506. The template nucleic acid may also have other modifications, such as the inclusion of heteroatoms, the attachment of labels, such as dyes, or substitution with functional groups which will still allow for base pairing and for recognition by the enzyme.

The synthesis reaction will typically include a template or target nucleic acid sequence that is sought to be replicated, as well as a primer sequence that specifically hybridizes to a portion of the template or target sequence. The nucleic acid template and primer can be selected to influence the kinetics of the polymerase reaction, and can be utilized to prepare a system in which two slow-step kinetics is observed.

The template sequence may be provided in any of a number of different format types depending upon the desired application. For example, in some cases, the template sequence may be a linear single or double stranded nucleic acid sequence. In still other embodiments, the template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220,674, filed Jul. 25, 2008. Alternate functional circular constructs are also described in U.S. patent application Ser. No. 12/383,855, entitled "Method and Compositions for Nucleic Acid Sample Preparation" filed Mar. 27, 2009, and U.S. patent application Ser. No. 12/413,258, the full disclosures of each of which are incorporated herein by reference in their entirety for all purposes.

Briefly, such alternate constructs include template sequences that possess a central double stranded portion that is linked at each end by an appropriate linking oligonucleotide, such as a hairpin loop segment. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

The polymerase enzymes of the invention generally require a primer, which is usually a short oligonucleotide that is complementary to a portion of the template nucleic acid. The primers of the invention can comprise naturally occurring RNA or DNA oligonucleotides. The primers of the invention may also be synthetic analogs. The primers may have alternative backbones as described above for the nucleic acids of the invention. The primer may also have other modifications, such as the inclusion of heteroatoms, the attachment of labels, such as dyes, or substitution with functional groups which will still allow for base pairing and for recognition by the enzyme. Primers can select tighter binding primer sequences, e.g., GC rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template.

The primer can be selected to influence the kinetics of the polymerase reaction, and to prepare a system in which two slow-step kinetics is observed.

As used in the art, the term nucleotide refers both to the nucleoside triphosphates that are added to a growing nucleic acid chain in the polymerase reaction, and also to refer to the individual units of a nucleic acid molecule, for example the units of DNA and RNA. Herein, the term nucleotide used in this manner. Whether the term nucleotide refers to the substrate molecule to be added to the growing nucleic acid or to the units in the nucleic acid chain can be derived from the context in which the term used.

The nucleotides or set of nucleotides of the invention can be naturally occurring nucleotides or modified nucleotides (nucleotide analogs). The nucleotides used in the invention, whether natural, unnatural, modified or analog are suitable for participation in the polymerase reaction. For example, the term nucleotide is used to refer to nucleotides that are labeled with fluorescent dye group. The term nucleotide may also be used to refer to nucleotides having other than three phosphate groups, for example 4, 5, 6, 7 or more phosphate groups. Such nucleotides have been described, for example in U.S. Pat. Nos. 6,936,702 and 7,041,812. Labels such as fluorescent dye group may be located in various positions on the nucleotide. In some cases, a fluorescent dye is located on the terminal phosphate of the nucleotide. The term nucleotide as used herein also comprises nucleotide analogs.

The type of nucleotide or set of nucleotides in the polymerase reaction can be selected to obtain a system that exhibits two slow-step kinetics.

The nucleotide compositions may include nucleoside triphosphates, or analogs of such compounds. For example, in some cases, the reaction mixtures will include nucleotide analogs having longer phosphate chains, such as nucleoside tetra, penta-, hexa- or even heptaphosphates. In addition, the nucleotide analogs of the compositions of the invention may additionally include other components, such as detectable labeling groups. Such detectable labeling groups will typically impart an optically or electrochemically detectable property to the nucleotide analogs being incorporated into the synthesis reaction. In particularly preferred aspects, fluorescent labeling groups, i.e., labeling groups that emit light of one wavelength when excited with light of another wavelength, are used as the labeling groups. For purposes of the present disclosure, the foregoing or later discussed nucleotide or nucleotide analog compositions whether labeled or unlabeled, possessing of three or more phosphate groups, or otherwise modified, are generally referred to herein as nucleotides.

Typically, each of the different types of nucleotide analogs will be labeled with a detectably different fluorescent labeling group, e.g., that possesses a detectably distinct fluorescent emission and/or excitation spectrum, such that it may be identified and distinguished from different nucleotides upon incorporation. For example, each of the different types of nucleotides, e.g., A, T, G and C, will be labeled with a fluorophore having a different emission spectrum. For certain embodiments, the nucleotide may include a fluorescent labeling group coupled to a portion of the nucleotide that is incorporated into the nascent nucleic acid strand being produced during synthesis, e.g., the nucleobase or sugar moiety. Nucleotide compositions having fluorophores coupled to these portions have been previously described (See, e.g., U.S. Pat. Nos. 5,476,928 and 4,711,955 to Ward et al.). As a result of the label group being coupled to the base or sugar portion of the nucleotide, upon incorporation, the nascent strand will include the labeling group. This labeling group may then remain or be removed, e.g., through the use of cleavable linkages joining the label to the nucleotide (See, e.g., U.S. Pat. No. 7,057,026). A variety of different fluorophore types, including both organic and inorganic fluorescent materials, have been described for biological applications and are likewise applicable in the instant invention.

Alternatively and preferably, the labeling group is coupled to a portion of the polyphosphate chain that is removed by the polymerase action during the incorporation event, e.g., the beta, gamma or further distal phosphate group. Examples of such phosphate labeled nucleotide analogs and their use in sequencing applications are described in, e.g., U.S. Pat. Nos. 6,399,335, 6,762,048, 7,041,812 and published U.S. Patent Application No. 2006-0063173. Because the label is included on a portion of the nucleotide that is cleaved during incorporation, the labeling group is not actually incorporated into the nascent strand, but instead, diffuses away from the synthesis complex. As described previously, where the complex is provided within all optical confinement, e.g., a zero-mode waveguide, the act of incorporation provides a characteristic retention of the label prior to its cleavage and diffusion away, so as to permit the recognition of an incorporation event. Further, by identifying the spectral characteristics of the label associated with the base being incorporated, one can identify the specific type of base.

In certain embodiments, the nucleotides or the complex as a whole may be provided with cooperative fluorescent labeling groups, e.g., that act cooperatively as a donor-quencher or fluorescent resonant energy transfer pair, to provide labeling. As noted above, in this context, the necessity for optical confinement to eliminate background signal from unincorporated labels or nucleotides is reduced, as substantially only interacting labels brought into sufficient proximity by the incorporation event (in the case of complex and nucleotide bound interactive labels), or only labels separated by cleavage of the polyphosphate chain upon incorporation, will produce a characteristic signal indicative of incorporation.

Other fluorescent labeling groups may likewise be employed in the nucleotide compositions, including inorganic fluorescent materials, such as semiconductor nanocrystals, like II-VI or III-V semiconductor nanocrystals, including CdSe, CdTe, InS, ZnS or other nanocrystal compositions, available from, e.g., e-Biosciences, Inc. (San Diego, Calif.), and Life Technologies. Inc.

The nucleotides of the present invention include nucleotides having the structure:

B-S-P-L, wherein B is a natural or non-natural nucleobase, S is selected from a sugar moiety, an acyclic moiety or a carbocyclic moiety, P is a modified or unmodified polyphosphate, and L is a detectable label optionally including a linker.

The base moiety, B, incorporated into the compounds of the invention is generally selected from any of the natural or non-natural nucleobases or nucleobase analogs, including, e.g., purine or pyrimidine bases that are routinely found in nucleic acids and nucleic acid analogs, including adenine, thymine, guanine, cytidine, uracil, and in some cases, inosine. For purposes of the present description, nucleotides and nucleotide analogs are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

In the nucleotides of the invention, the S group is generally a sugar moiety that provides a suitable backbone for a synthesizing nucleic acid strand. In it most preferred aspect, the sugar moiety is selected from a D-ribosyl, 2' or 3' D-deoxyribosyl, 2',3'-D-dideoxyribosyl, 2',3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties may be incorporated as the "S" group in place of a sugar moiety, including, e.g., those described in published U.S. Patent Application No. 2003/0124576, previously incorporated herein by reference in its entirety for all purposes.

The P groups in the nucleotides of the invention are modified or unmodified polyphosphate groups. The number of phosphates in the polyphosphate can be 1, 2, 3, 4, 5, 5, 7, 8 or more modified or unmodified phosphates. The unmodified phosphates have linearly linked —O—P(O)$_2$— units, for example a monophosphate, diphosphate, triphosphate, tetraphosphate, pentaphosphate, hexaphosphate, heptaphosphate, or octaphosphate. The P groups also include modified polyphosphates, for example by virtue of the inclusion of one or more phosphonate groups, effectively substituting a non-ester linkage in the phosphorous containing chain of the analog, with a more stable linkage. Examples of preferred linkages include, e.g., CH$_2$, methylene derivatives (e.g., substituted independently at one or more hydrogens with F, Cl, OH, NH2, alkyl, alkenyl, alkynyl, etc.), CCl$_2$, CF$_2$, NH, S, CH$_2$CH$_2$, C(OH)(CH$_3$), C(NH$_2$)[(CH$_2$)$_6$CH$_3$], CH(NHR) (R is H or alkyl, alkenyl, alkynyl, aryl, C(OH)[(CH$_2$)$_n$NH2] (n is 2 or 3), and CNH$_2$. In particularly preferred aspects, methylene, amide or their derivatives are used as the linkages.

Other P groups of the invention have phosphate or modified phosphates in which one or more non-bridging oxygen is substituted, for example with S, or BH3. In one aspect of the invention, one or more, two or more, three or more, or four or more non-bridging oxygen atoms in the P group has an S substituted for an O. The substitution of, sulfur atoms for oxygen can change the polymerase reaction kinetics such that a system having two slow steps can be selected. While not being bound by theory, it is believed that the properties of the nucleotide, such as the metal chelation properties, electronegativity, or steric properties are the nucleotide can be altered by the substitution of non-bridging oxygen for sulfur in P. In some cases, it is believed that the substitution of two or more non-bridging oxygen atoms with sulfur can affect the metal chelation properties so as to lead to a two slow-step system.

Suitable nucleotides include nucleotides having 4, 5, 6, or 7 phosphates in which a sulfur is substituted for one of the non-bridging oxygens. In some embodiments, the single sulfur substitution is made such that substantially only one stereoisomer is present. The nucleotide can have 7 phosphates in which phosphate 2, 3, 4, 5, 6, or 7 has a non-bridging sulfur in place of oxygen. The nucleotide can have 6 phosphates in which phosphate 2, 3, 4, 5, or 6 has a non-bridging sulfur in place of oxygen. The nucleotide can have 5 phosphates in which phosphate 2, 3, 4, or 5 has a non-bridging sulfur in place of oxygen. The substituted phosphate in the nucleotide can be the R or the S stereoisomer.

The nucleotide can have 6 phosphates in which phosphate 2 has sulfur substituted for oxygen. The nucleotide can have 6 phosphates in which phosphate 2 has sulfur substituted for oxygen and phosphate 2 is the R stereoisomer. The nucleotide can have 6 phosphates in which phosphate 2 has sulfur substituted for oxygen and phosphate 2 is the S stereoisomer. The nucleotide can have 6 phosphates in which phosphate 6 has sulfur substituted for oxygen. The nucleotide can have 6 phosphates in which phosphate 6 has sulfur substituted for oxygen and phosphate 6 is the R stereoisomer. The nucleotide can have 6 phosphates in which phosphate 6 has sulfur substituted for oxygen and phosphate 6 is the S stereoisomer. The nucleotide can have 7 phosphates in which phosphate 2 has sulfur substituted for oxygen and phosphate 2 is the S stereoisomer. The nucleotide can have 7 phosphates in which phosphate 6 has sulfur substituted for oxygen. The nucleotide can have 7 phosphates in which phosphate 6 has sulfur substituted for oxygen and phosphate 6 is the R stereoisomer. The nucleotide can have 7 phosphates in which phosphate 6 has sulfur substituted for oxygen and phosphate 6 is the S stereoisomer.

Figure 23:
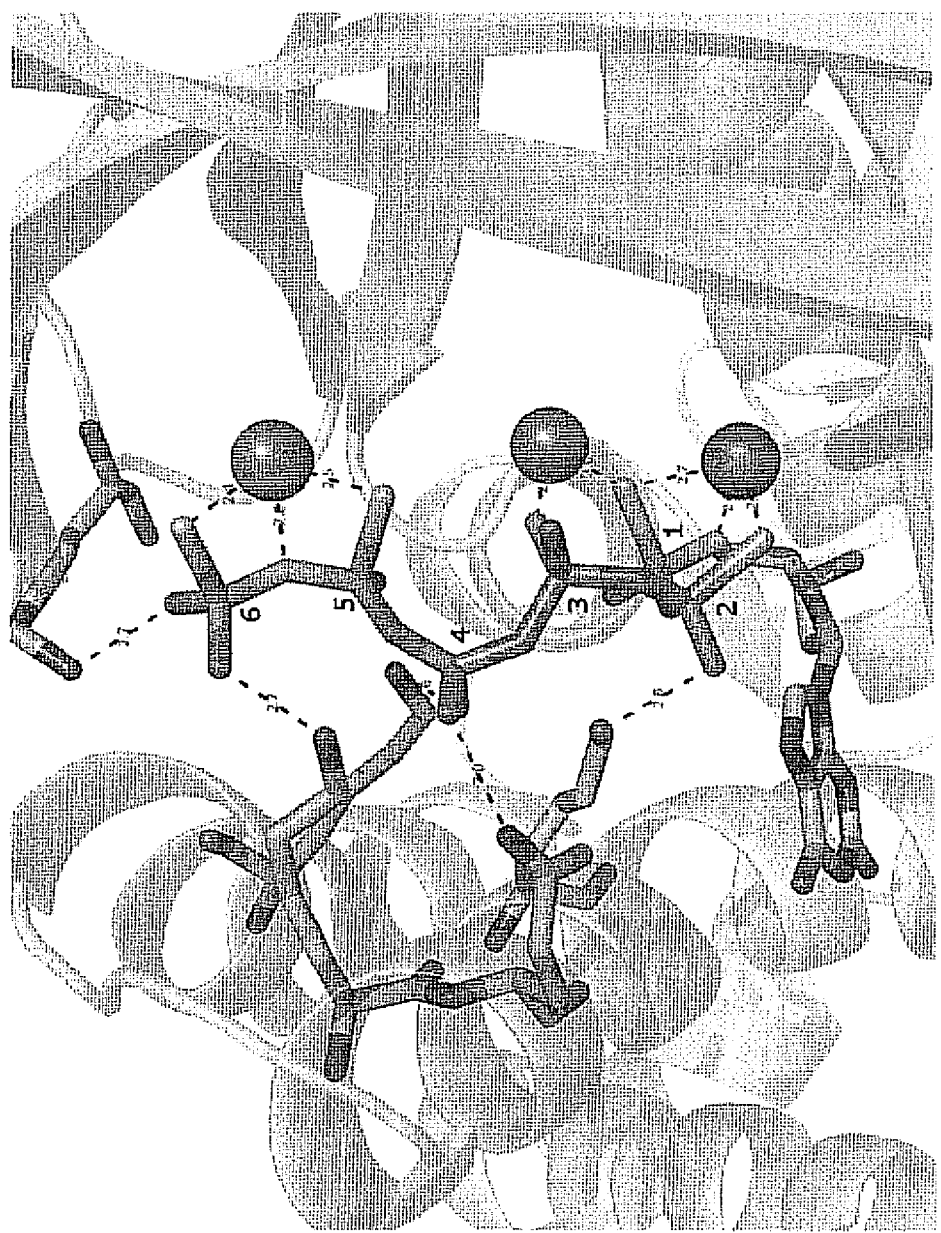
FIG. 23 shows a 3-dimensional model of a nucleotide having 6 phosphate units bound to the phi29 polymerase enzyme.

While not being bound by theory, it is believed that two-slow-step kinetics can be obtained from the stabilized metal ion coordination between the non-bridging sulfur on the nucleotide and the manganese or other metal cofactor atoms in the enzyme complex. Based on the structural analysis of a crystal structure of phi29 DNA polymerases, specific non-bridging oxygen atoms on the phosphate are coordinated with manganese atom. FIG. 23 shows a model of a nucleotide having 6 phosphate units bound to the enzyme. The phosphates are labeled 1 through 6. The non-bridging oxygens (or substituted sulfurs) can be seen as extending from the phosphorous atoms. Hydrogen bonding interactions and metal ion coordination are represented as black dashed lines. The manganese ions are shown as spheres. FIG. 23 shows that some non-bridging oxygen atoms on the phosphate are hydrogen bound to the positively charged residues on the polymerase L-helix. Other non-bridging oxygen atoms are in coordination with manganese atoms in the complex. Thus, in some cases, a specific stereoisomer can be useful for obtaining two slow-step kinetics, while the other isomer will not be effective. Note, for example, that the oxygens on the 2nd and 6th phosphates have contacts to manganese ions.

L generally refers to a detectable labeling group that is coupled to the terminal phosphorus atom via the R.sub.4 (or R.sub.10 or R.sub.12) group. The labeling groups employed in the analogs of the invention may comprise any of a variety of detectable labels. As used herein, labels or detectable labels generally denote a chemical moiety that provides a basis for detection of the analog compound separate and apart from the same compound lacking such a labeling group. Examples of labels include, e.g., optical labels, e.g., labels that impart a detectable optical property to the analog, electrochemical labels, e.g., labels that impart a detectable electrical or electrochemical property to the analog, physical labels, e.g., labels that impart a different physical or spatial property to the analog, e.g., a mass tag or molecular volume tag. In some cases individual labels or combinations may be used that impart more than one of the aforementioned properties to the nucleotide analogs of the invention.

In preferred aspects, the labeling groups incorporated into the analogs of the invention comprise optically detectable moieties, including luminescent, chemiluminescent, fluorescent, fluorogenic, chromophoric and/or chromogenic moieties, with fluorescent and/or fluorogenic labels being particularly preferred. A variety of different label moieties are readily employed in nucleotide analogs, and particularly, the compound of the invention. Such groups include fluorescein labels, rhodamine labels, cyanine labels (i.e., Cy3, Cy5, and the like, generally available from the Amersham Biosciences division of GE Healthcare), the Alexa family of fluorescent dyes and other fluorescent and fluorogenic dyes available from Molecular Probes/Invitrogen, Inc., and described in 'The Handbook—A Guide to Fluorescent Probes and Labeling Technologies, Tenth Edition' (2005) (available from Invitrogen, Inc./Molecular Probes). A variety of other fluorescent and fluorogenic labels for use with nucleoside polyphosphates, and which would be applicable to the compounds of the present invention are described in, e.g., Published U.S. Patent Application No. 2003/0124576, the full disclosure of which is incorporated herein in its entirety for all purposes.

The label group may be directly coupled to the terminal phosphorus atom of the analog structure, in alternative aspects, it may additionally include a linker molecule to provide the coupling through, e.g., an alkylphosphonate linkage. A wide variety of linkers and linker chemistries are known in the art of synthetic chemistry may be employed in coupling the labeling group to the analogs of the invention. For example, such linkers may include organic linkers such as alkane or alkene linkers of from about C2 to about C20, or longer, polyethyleneglycol (PEG) linkers, aryl, heterocyclic, saturated or unsaturated aliphatic structures comprised of single or connected rings, amino acid linkers, peptide linkers, nucleic acid linkers, PNA, LNAs, or the like or phosphate or phosphonate group containing linkers. In preferred aspects, allyl, e.g., alkane, alkene, alkyne alkoxy or alkenyl, or ethylene glycol linkers are used. Some examples of linkers are described in Published U.S. Patent Application No. 2004/0241716, which is incorporated herein by reference in its entirety for all purposes. Additionally, such linkers may be selectively cleavable linkers, e.g., photo- or chemically cleavable linkers or the like. The linkers can be allyl, aryl, or ester linkers. The linkers can be, amino-alkyl linkers, e.g., amino-hexyl linkers. In some cases, the linkers can be rigid linkers such as disclosed in U.S. patent application Ser. No. 12/403,090.

The B, S, P, and L groups can be connected directly, or can be connected using an linking unit such as an —O—, —S—, —NH—, or —CH$_2$— unit.

III. Single-Molecule Sequencing Processes and Systems

As noted, the mixtures of catalytic and non-catalytic metals in the reaction mixture provide for the modulation of the reaction kinetics of individual complexes. Accordingly, in particularly preferred aspects, the synthesis complexes in such reaction mixtures are arrayed so as to permit observation of the individual complexes that are being so modulated. In arraying individual complexes to be individually optically resolvable, the systems of the invention will position the complexes on solid supports such that there is sufficient distance between adjacent individual complexes as to allow optical signals from such adjacent complexes to be optically distinguishable from each other.

Typically, such complexes will be provided with at least 50 nm and more preferably at least 100 nm of distance between adjacent complexes, in order to permit optical signals, and particularly fluorescent signals, to be individually resolvable. Examples of arrays of individually resolvable molecules are described in, e.g., U.S. Pat. No. 6,787,308.

In some cases, individual complexes may be provided within separate discrete regions of a support. For example, in some cases, individual complexes may be provided within individual optical confinement structures, such as zero-mode waveguide cores. Examples of such waveguides and processes for immobilizing individual complexes therein are described in, e.g., Published International Patent Application No. WO 2007/123763, the full disclosure of which is incorporated herein by reference in its entirety for all purposes.

As noted previously, in preferred aspects, the synthesis complexes are provided immobilized upon solid supports, and preferably, upon supporting substrates. The complexes may be coupled to the solid supports through one or more of the different groups that make up the complex. For example, in the case of nucleic acid polymerization complexes, attachment to the solid support may be through an attachment with one or more of the polymerase enzyme, the primer sequence and/or the template sequence in the complex. Further, the attachment may comprise a covalent attachment to the solid support or it may comprise a non-covalent association. For example, in particularly preferred aspects, affinity based associations between the support and the complex are envisioned. Such affinity associations include, for example, avidin/streptavidin/neutravidin associations with biotin or biotinylated groups, antibody/antigen associations, GST/glutathione interactions, nucleic acid hybridization interactions, and the like. In particularly preferred aspects, the complex is attached to the solid support through the provision of an avidin group e.g., streptavidin, on the support, which specifically interacts with a biotin group that is coupled to the polymerase enzyme.

Methods of providing binding groups on the substrate surface that result in the immobilization of optically resolvable complexes are described in, e.g., published U.S. Patent Application No. 2007-0077564, incorporated herein by reference in its entirety for all purposes, and WO 2007123763, previously incorporated herein by reference.

The sequencing processes, e.g., using the substrates described above and the synthesis compositions of the invention, are generally exploited in the context of a fluorescence microscope system that is capable of illuminating the various complexes on the substrate, and obtaining detecting and separately recording fluorescent signals from these complexes. Such systems typically employ one or more illumination sources that provide excitation light of appropriate wavelength(s) for the labels being used. An optical train directs the excitation light at the reaction region(s) and collects emitted fluorescent signals and directs them to an appropriate detector or detectors. Additional components of the optical train can provide for separation of spectrally different signals, e.g., from different fluorescent labels, and direction of these separated signals to different portions of a single detector or to different detectors. Other components may provide for spatial filtering of optical signals, focusing and direction of the excitation and or emission light to and from the substrate.

Figure 4:
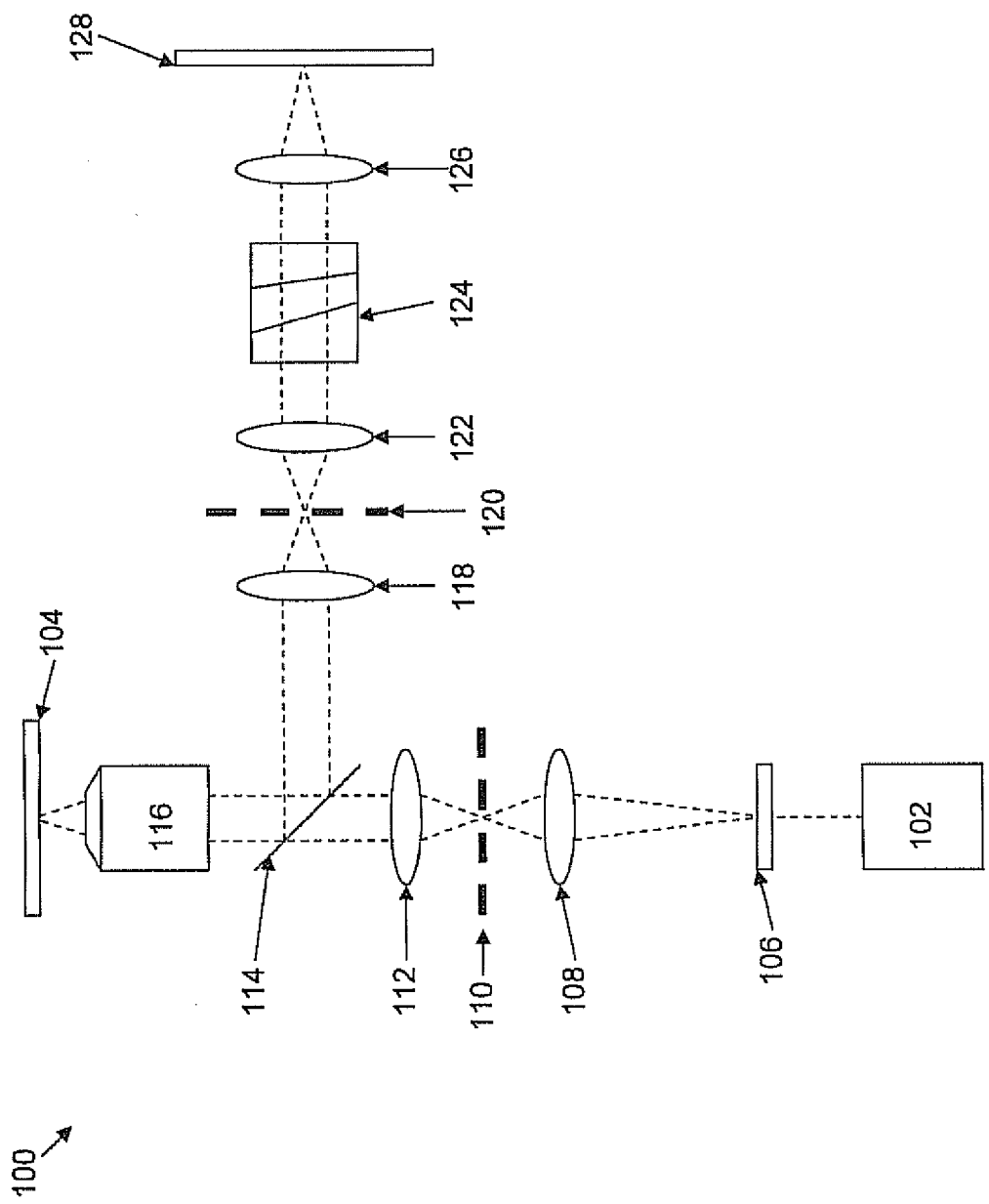
FIG. 4 schematically illustrates a simplified system for analysis of sequencing-by-incorporation reactions.

One such exemplary system is shown in FIG. 4. As shown, the overall system 300 generally includes an excitation illumination source 302. Typically, such illumination sources will comprise high intensity light sources such as lasers or other high intensity sources such as LEDs, high intensity lamps (mercury, sodium or xenon lamps), laser diodes, and the like. In preferred aspects, the sources will have a relatively narrow spectral range and will include a focused and/or collimated or coherent beam. For the foregoing reasons, particularly preferred light sources include lasers, solid state laser diodes, and the like. An exemplar system is also described in Lundquist et al., Optics Letters, Vol. 33, Issue 9, pp. 1026-1028, the full disclosure of which is incorporated herein by reference in its entirety for all purposes.

The excitation illumination source 302 is positioned to direct light of an appropriate excitation wavelength or wavelength range, at a desired fluorescent signal source, e.g., substrate 304, through an optical train. As shown, the optical train includes a number of elements to appropriately direct excitation illumination at the substrate 304, and receive and transmit emitted signals from the substrate to an appropriate detection system such as detector 328. The excitation illumination from illumination source 302 is directed first through an optical multiplex element 306, or elements, to multiply the number of illumination beams or spots from an individual beam or spot from the illumination source 302. The multiplexed beam(s) is then directed via focusing lens 308 through optional first spatial filter 310, and focusing lens 312. As discussed in greater detail below, spatial filter 310 optionally provides control over the extent of multiplex beams continuing through the optical train reduces the amount of any scattered excitation light from reaching the substrate. The spatially filtered excitation light is then passed through dichroic 314 into objective lens 316, whereupon the excitation light is focused upon the substrate 304. Dichroic 314 is configured to pass light of the spectrum of the excitation illumination while reflecting light having the spectrum of the emitted signals from the substrate 304. Because the excitation illumination is multiplexed into multiple beams, multiple discrete regions of the substrate are separately illuminated.

Fluorescent signals that are emitted from those portions of the substrate that are illuminated, are then collected through the objective lens 316, and, because of their differing spectral characteristics, they are reflected by dichroic 314, through focusing lens 318, and second spatial filter, such as confocal mask 320, and focusing lens 322. Confocal mask 320 is typically positioned in the focal plane of lens 318, so that only in-focus light is passed through the confocal mask, and out-of focus light components are blocked. This results in a substantial reduction in noise levels from the system, e.g., that derive from out of focus contributors, such as autofluorescence of the substrate and other system components.

As with the excitation illumination, the signals from the multiple discrete illuminated regions on the substrate are separately passed through the optical train. The fluorescent signals that have been subjected to spatial filtering are then passed through a dispersive optical element, such as prism assembly 324, to separately direct spectrally different fluorescent signal components, e.g., color separation, which separately directed signals are then passed through focusing lens 326 and focused upon detector 328, e.g., an imaging detector such as a CCD, ICCD, EMCCD or CMOS based detection element. Again, the spectrally separated components of each individual signal are separately imaged upon the detector, so that each signal from the substrate will be imaged as separate spectral components corresponding to that signal from the substrate. For a discussion of the spectral separation of discrete optical signals, see, e.g., Published U.S. Patent Application No. 2007-0036511, incorporated herein by reference in its entirety for all purposes.

As will be appreciated, a more conventional configuration that employs reflected excitation light and transmitted fluorescence may also be employed by altering the configuration of and around dichroic 314. In particular, dichroic 314 could be selected to be reflective of the excitation light from illumination source 302, and transmissive to fluorescence from the substrate 304. The various portions of the optical train are then arranged accordingly around dichroic 314. Notwithstanding the foregoing, fluorescence reflective optical trains are particularly preferred in the applications of the systems of the invention. For a discussion on the advantages of such systems, see, e.g., U.S. patent application Ser. No. 11/704,689, filed Feb. 9, 2007, U.S. patent application Ser. No. 11/483,413, filed Jul. 7, 2006, and U.S. patent application Ser. No. 11/704,733, filed Feb. 9, 2007, the full disclosures of which are incorporated herein by reference in their entirety for all purpose.

In addition to the foregoing composition components, additional components may also be included within the compositions of the invention. For example, such compositions will typically include buffering agents, salts, and other agents that facilitate the desired reactions.

In certain embodiments, the sequencing compositions described herein will be provided in whole, or in part, in kit form enabling one to carry out the processes described herein. Such kits will typically comprise one or more components of the reaction complex, such as the polymerase enzyme and primer sequences. Such kits will also typically include buffers and reagents that provide the catalytic and non-catalytic metal co-factors employed in the processes described herein. The kits will also optionally include other components for carrying out sequencing applications in accordance with those methods described herein. In particular, such kits may include ZMW array substrates for use in observing individual reaction complexes as described herein.

In addition to the various components set forth above, the kits will typically include instructions for combining the various components in the amounts and/or ratios set forth herein, to carry out the desired processes, as also described or referenced herein, e.g., for performing sequence by incorporation reactions.

VI. Examples

Example 1

Single-Molecule Sequencing in Zero-Mode Waveguides

Sequencing reactions are carried out in a zero-mode waveguide array having 3000 discrete cores. The reaction is observed using a highly multiplexed confocal fluorescent microscope providing a targeted illumination profile, e.g., a separate spot for each core (See, e.g., U.S. patent application Ser. No. 12/151,979, filed May 9, 2008, and incorporated herein by reference in its entirety for all purposes). Fluorescent signals from the various ZMWs are detected on an EMCCD camera for 5-7 minutes, and are subjected to pulse recognition and base calling processes (See, e.g., Published U.S. Patent Application No. 2009-0024331, and incorporated herein by reference in its entirety for all purposes).

Example 2

Catalytic and Non-Catalytic Metals

The effects of catalytic and non-catalytic metal ions and mixtures thereof on nucleotide incorporation in polymerase mediated template dependent primer extension reactions.

A. Stopped Flow Incorporation Assays.

The oligonucleotides that constitute the template/primer complex were purchased from Integrated DNA Technologies (Coralville, Iowa). The position iAmMC6T has an Int amino modified C6 dT substituted for dT at this position. The "template" oligonucleotide was labeled at position "iAmMC6T" with alexa fluor 488 fluorescent dye.

Sequence of oligonucleotides used for the assays.

```
5'-GGT GAT GTA GAT AGG TGG TAG GTG GTG TCA         GAT C

3'-CCA CTA CAT CTA TCC ACC ATC CAC CAC AG/iAmMC6T/ CTA GGC ATA ATA ACA GTT GCA GCA
```

The double stranded sequence above corresponds to SEQ ID NO 1 hybridized to SEQ ID 2.

This stopped flow assay relies on the quenching, for example by fluorescent resonance energy transfer (FRET) of the fluorescence of the Alexa fluor 488 attached to the template by a dye labeled nucleotide. A nucleotide having an Alexa fluor 555 as a terminal phosphate label, such as Alexa fluor 555-O-aminohexyl-dT6P (A555-O-dC6P), having six phosphates, is used in the polymerase reaction, which will quench the fluorescence of the Alexa fluor 488 dye attached to the template only when the nucleotide is associated with (bound to) the polymerase enzyme.

The drop in the fluorescent signal, measured at 535 nm, is attributed to binding of the Alexa-555-dC6P nucleotide to the enzyme-DNA complex. Because quenching only occurs when the two dyes are in close proximity, a significant drop in the fluorescence of alexa fluor 488 due to the presence of alexa fluor 555 in solution would not be expected to occur. Alexa-555-dC6P bound in the active site of the enzyme, however, will cause a drop in the fluorescence of alexa fluor 488 labeled oligonucleotide. The rate of drop of the measured fluorescence signal is a function of the rate of binding of the nucleotide to the active site of the enzyme.

Once bound, the nucleotide analog can undergo nucleotidyl transfer catalyzed by the polymerase enzyme, extending the oligonucleotide. Subsequent to extension of the oligonucleotide, the product, the alexa fluor 555-pentaphosphate is released from the enzyme. Once released from the enzyme DNA complex, the alexa fluor 555-pentaphosphate no longer quenches the alexa fluor 488 attached to the template in the enzyme-DNA complex, and the measured fluorescence signal increases at a rate that is a function of the release of product.

Figure 5:
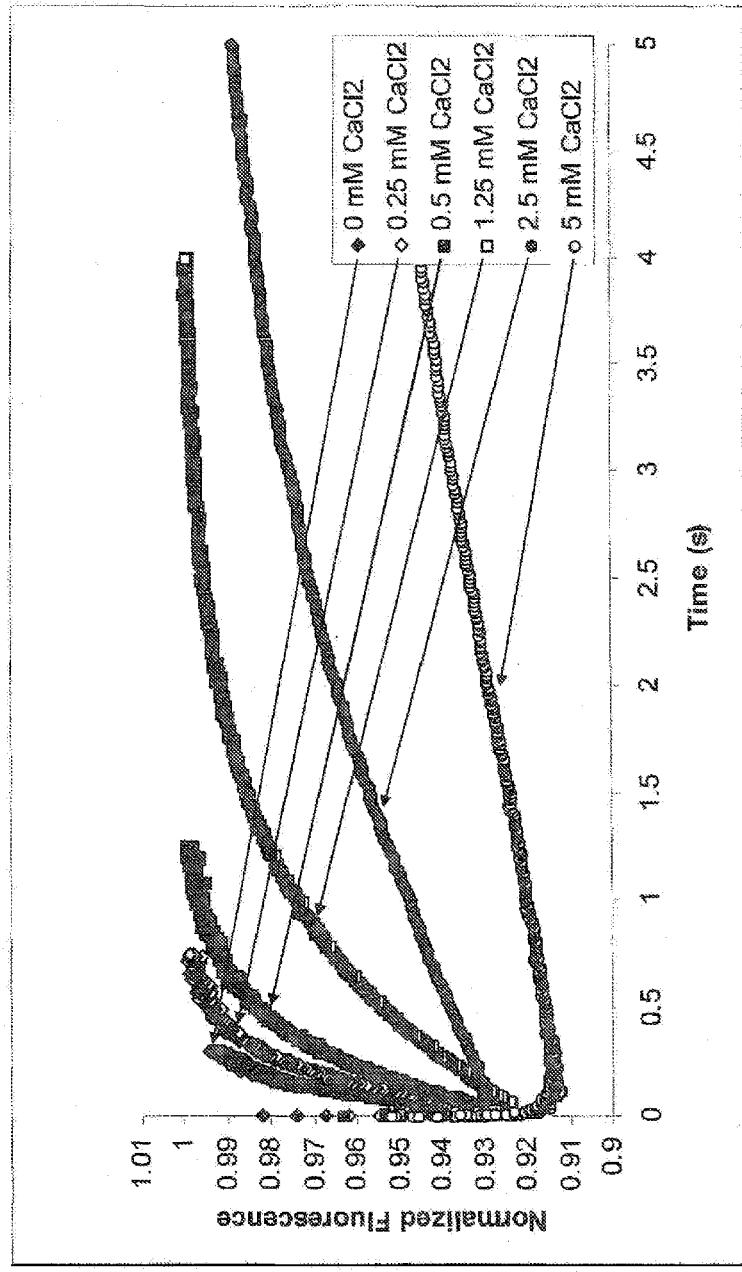
FIG. 5 shows a plot of the effects of $Ca^{2+}$ ion concentration on nucleotide binding and incorporation by DNA polymerase in the presence of manganese.

The DNA polymerase (recombinant DNA polymerase (see published U.S. Patent Application No. 2007-0196846, which is incorporated herein by reference in its entirety for all purposes), at 150 nM) was incubated with an oligonucleotide primer-template complex (20 nM) in a buffer solution containing 50 mM ACES, pH 7.1, 75 mM potassium acetate, and 5 mM dithiothreitol (Buffer A). This solution was rapidly mixed with a solution containing Buffer A and 6 µM Alexa Fluor 555-dC6P, 1.4 mM manganese chloride, and varying concentrations of calcium chloride from 0 to 5 mM using a SF-2004 stopped flow instrument (Kintek Corporation, Austin, Tex.). The observed fluorescent trace was fit to a double exponential equation $(y)=A_1e^{-k_1 t}+A_2e^{-k_2 t}+c)$ to extract the observed rate constant for nucleotide binding and the observed rate constant for incorporation. This was performed over a series of CaCl$_2$ concentrations (0, 0.25, 0.5, 1.25, 2.5, and 5 mM) in order to map the effects of CaCl$_2$ on the rate constants for nucleotide binding and incorporation. The fluorescence traces are shown in FIG. 5. The rate constant for incorporation decreased from 8.5±0.1 s$^{-1}$ (at 0 mM CaCl$_2$) to 0.110±0.001 s$^{-1}$ (at 5 mM CaCl$_2$). The single-exponential nature of the fluorescence increase and the equivalence of the magnitude of the fluorescence increase over all concentrations of CaCl$_2$ assayed implies rapid exchange of the divalent metal ions in this assay. The observed rate constant for incorporation was then plotted as a function of the CaCl$_2$ concentration and then fitted to a hyperbolic equation $$\left(k_{obs} = k_{max} * \left(1 - \frac{[CaCl_2]}{K_i + [CaCl_2]}\right) + c\right).$$

Figure 6:
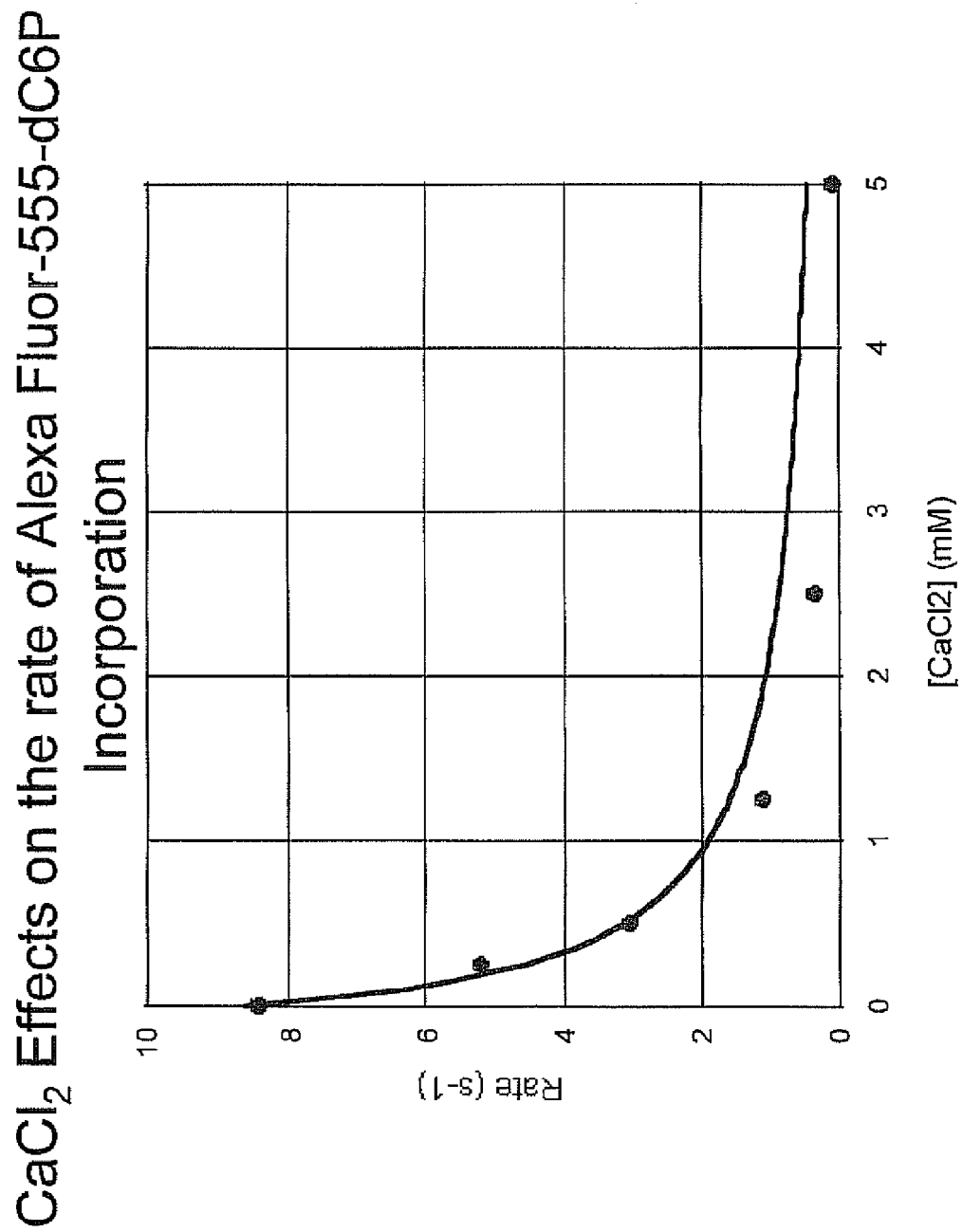
FIG. 6 shows a plot of the effects of $Ca^{2+}$ ion concentration on the rate of incorporation of nucleotides by a polymerase, fit to a hyperbolic equation.

The hyperbolic fit generated a maximum rate of incorporation of 8.6±0.5 s$^{-1}$ and an apparent $K_i$ for CaCl$_2$ of 0.29±0.6 mM. The hyperbolic fit of the observed incorporation rate constants vs. [CaCl$_2$] is shown in FIG. 6.

B. Alexa-555-dC6P Release Assay

Figure 7:
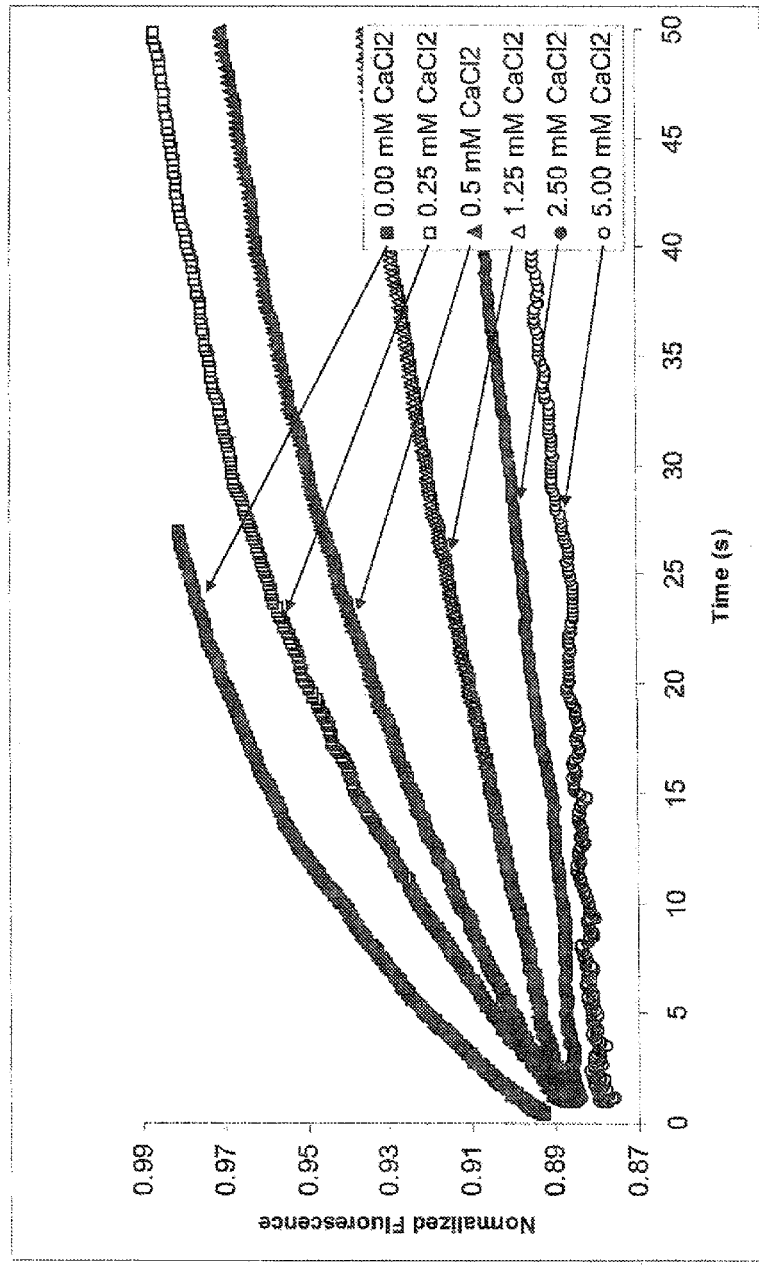
FIG. 7 shows a plot of the effects of $Ca^{2+}$ ion concentration on nucleotide release by DNA polymerase in the presence of manganese.
Figure 8:
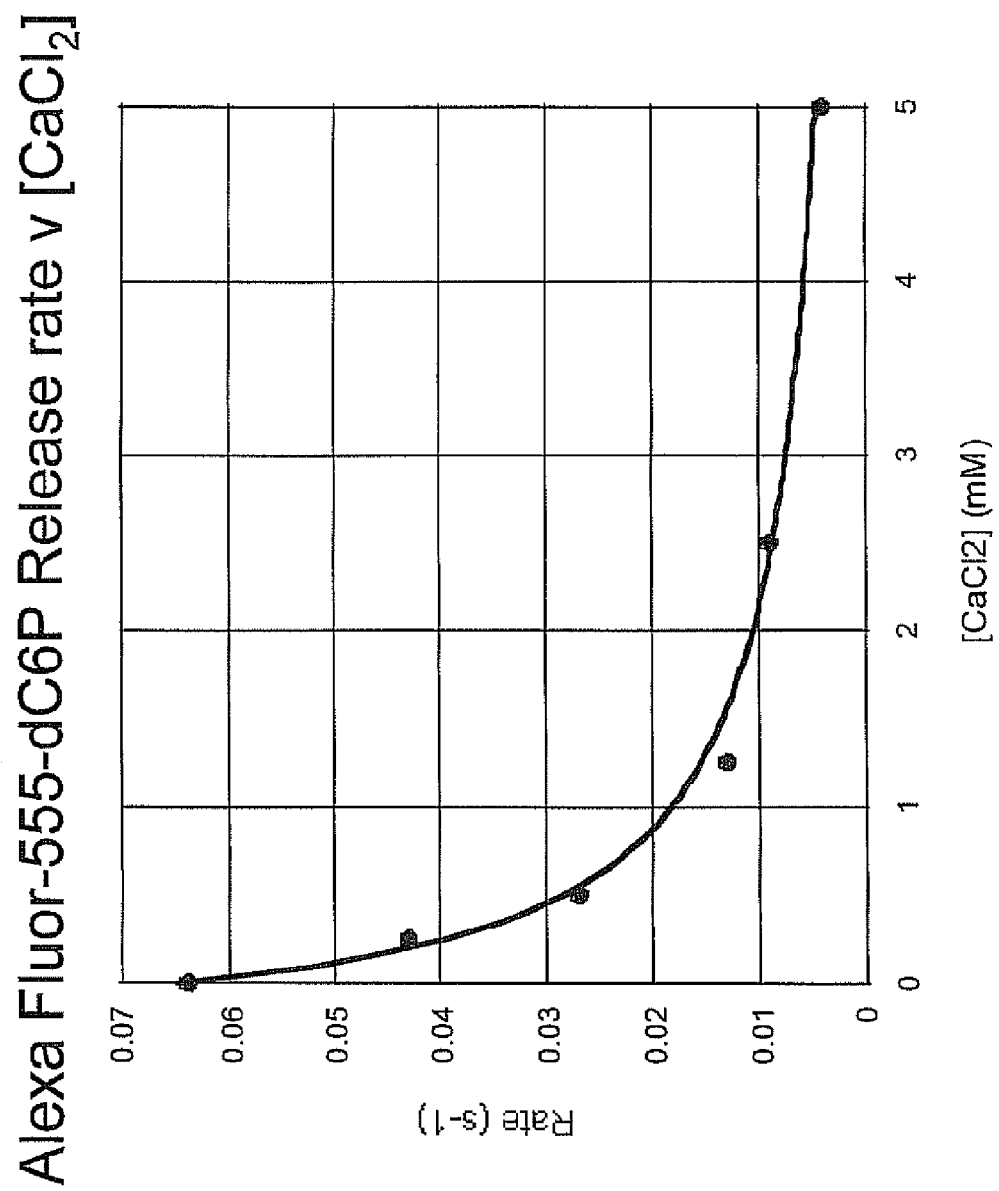
FIG. 8 shows a plot of the effects of $Ca^{2+}$ ion concentration on the rate of nucleotide release by polymerase enzyme, fit to a hyperbolic equation.

This experiment was carried out using the stopped flow instrument in "double-mixing mode" which allows the mixing of two samples prior to the addition of a third solution. The DNA polymerase (250 nM) was incubated with an oligonucleotide primer-template complex (50 nM) in Buffer A). The sequences of the primer and the template for this assay are identical to those in the incorporation assay, except that the primer for this assay has a 3' terminal dideoxy-CMP. This solution was mixed with a solution containing 6 µM Alexa Fluor-555-dC6P in Buffer A with 1.4 mM manganese chloride, and varying concentrations of CaCl$_2$ (0, 0.5, 1, 2.5, 5, and 10 mM). This mixture was allowed to incubate for 0.4 seconds prior to mixing with a solution containing 750 µM dCTP in Buffer A with 0.7 mM manganese chloride, and varying concentrations of CaCl$_2$ (0, 0.25, 0.5, 1.25, 2.5, 5 mM). The Alexa Fluor-488 dye on the DNA template was excited at 488 nm and emission was monitored at 515 nm. The FRET quenching of the fluorescence signal, observed in the stopped flow incorporation assay, occurs during the unobservable first mixing event. Because the primer for this experiment is 3'-dideoxyCMP terminated, no incorporation of the Alexa Fluor-555-dC6P can occur. The observed increase in the fluorescent signal is attributed to the release of the Alexa Fluor-555-dC6P from the enzyme-DNA-nucleotide complex. The fluorescence change was plotted versus time (FIG. 7) and fit to a single exponential equation (y=Ae$^{-kt}$+c). The rate of the change was plotted versus CaCl$_2$ concentration and fit to a hyperbolic equation (FIG. 8). This fit generated a maximum rate of release of 0.065±0.002 s$^{-1}$ and an apparent $K_i$ for CaCl$_2$ of 0.39±0.04 mM.

C. Exonuclease Assay

Figure 9:
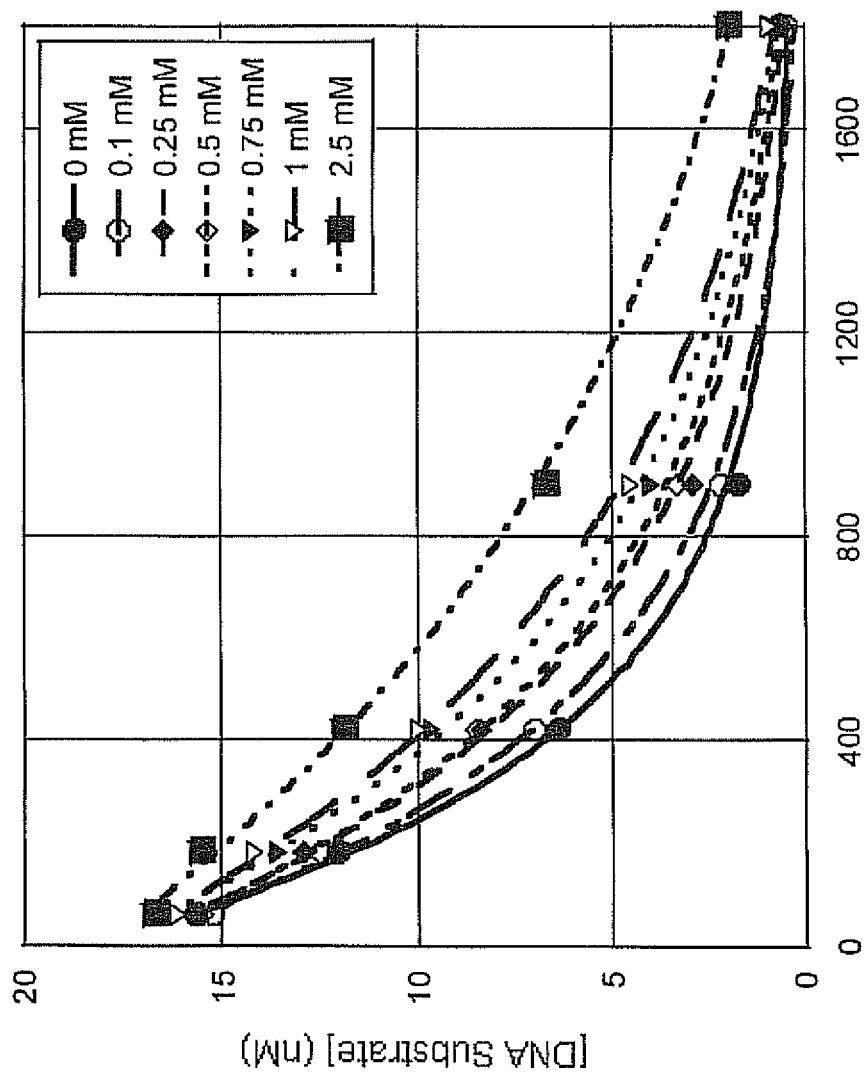
FIG. 9 shows a plot of $Ca^{2+}$ on exonuclease activity of a DNA polymerase enzyme in the presence of manganese.
Figure 10:
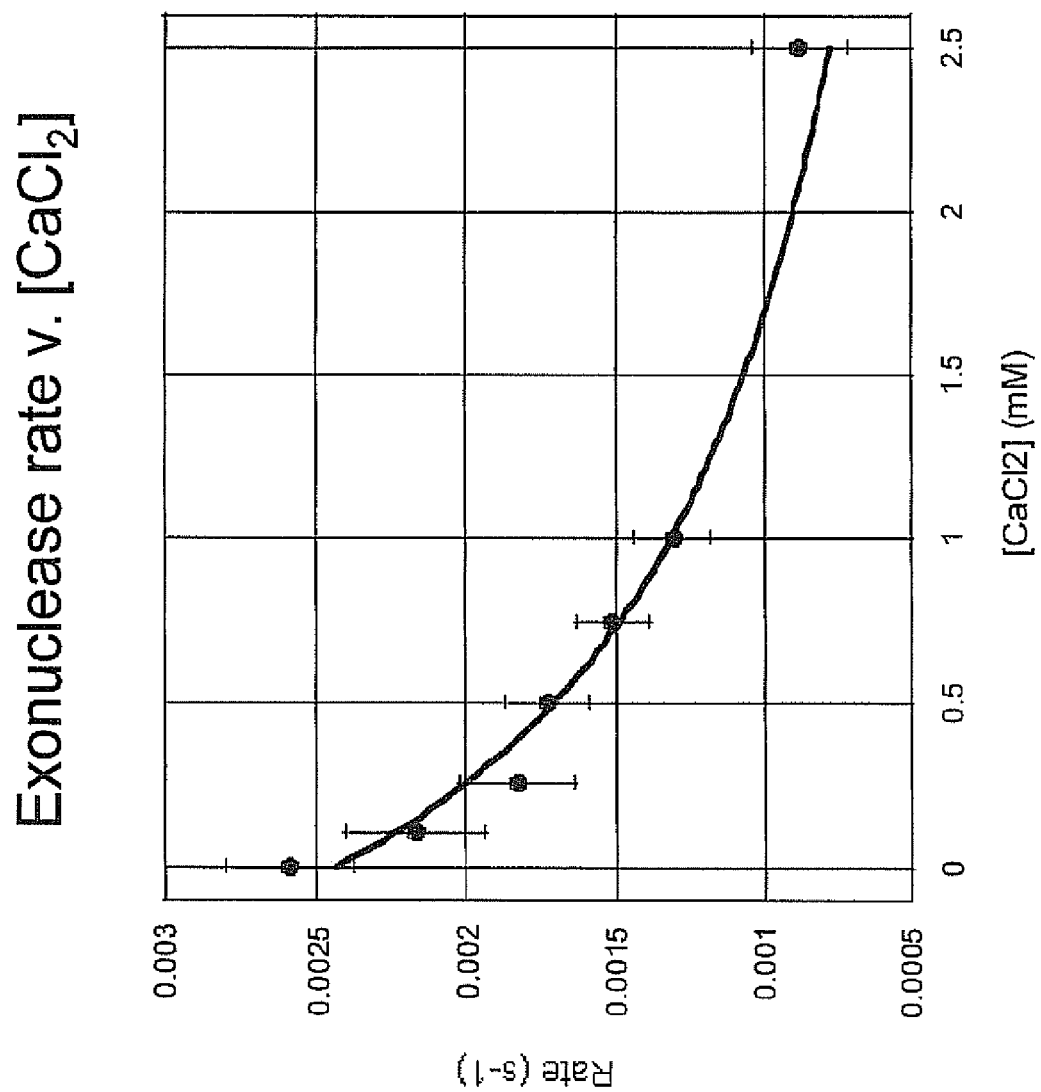
FIG. 10 shows a plot of the effects of $Ca^{2+}$ concentration on the exonuclease rate of a DNA polymerase, fit to a hyperbolic equation.

The DNA polymerase was preincubated with an oligonucleotide primer-template complex in Buffer A and varying concentrations of CaCl$_2$ (0, 0.1, 0.25, 0.5, 0.75, 1, 2.5, and 5 mM). This solution was rapidly mixed with Buffer A with 1.4 mM manganese chloride, and varying concentrations of CaCl$_2$ (0, 0.1, 0.25, 0.5, 0.75, 1, 2.5, and 5 mM). This reaction mixture was allowed to incubate for 30 minutes, with time points taken periodically from zero to 30 minutes. The time points were quenched in 0.5 M EDTA to stop the reaction, the products of the reactions were separated using 16% polyacrylamide gel electrophoresis, and visualized using a Typhoon 9400 variable mode scanner (Molecular Dynamics). The intensities of the product bands were quantified in order to determine the amount of substrate primer remaining at each time point. The substrate remaining was plotted against time and fit to a single exponential equation (FIG. 9). The observed rate constant for exonuclease activity was plotted against [CaCl$_2$] and fit to a hyperbolic equation (FIG. 10). The hyperbolic fit generated a maximum rate of exonuclease activity of 0.0019±0.0001 s$^{-1}$ and an apparent $K_i$ for CaCl$_2$ of 0.5±0.1 mM.

D. Cycle Sequencing

Nucleotide incorporation was monitored using an iterative process of cycling catalytic and noncatalytic metals through the reaction mixture as provided below.

A recombinant DNA polymerase covalently modified with biotin was incubated for 30 minutes with a primed DNA template (1 µM each) in buffer B (50 mM Aces pH 7.1, 130 mM KOAc, 5 mM DTT, 0.03% Tween20). Four wells of a Streptavidin Coated High Binding Capacity Clear 96-well plate (Prod# 15500 from ThermoScientific) were briefly hydrated and rinsed with 50 mM Tris pH 7.5. The buffer was completely removed from the four wells and 30 µl of the DNA polymerase-DNA complexes were added at room temperature and allowed to incubate for 30 minutes to adhere the complexes to the streptavidin-coated plate. The solution was removed and the wells were rinsed with 50 µl Buffer of Buffer B. A different sequencing mix (30 µl) was added to each of four wells in the first column of the plate. Well A1 contained 1 µM Alexa555-dA6P (See, e.g., Eid et al.,) plus 1 µM each of dCTP, dGTP, and dTTP in Buffer B with 1 mM CaCl$_2$. Well B1 contained 1 µM Alexa555-dC6P plus 1 µM each of dATP, dGTP, and dTTP in Buffer B with 1 mM CaCl$_2$. Well C1 contained 1 µM Alexa555-dT6P plus 1 µM each of dATP, dGTP, and dCTP in Buffer B with 1 mM CaCl$_2$. Well D1 contained 1 µM Alexa555-dT6P plus 1 µM each of dATP, dCTP, and dTCP in Buffer B with 1 mM CaCl$_2$. The sequencing mix was removed from each well and replaced with 50 µl Buffer B with 1 mM CaCl$_2$. The plate was read in a fluorescent plate reader (Beckman Paradigm with excitation wavelength 535 nm and emission wavelength 595 nm). The raw fluorescence intensity is plotted for each well (designated by the inclusion of fluorescently labeled base) in FIG. 11. The calcium buffer was removed and replaced with 40 µl Buffer B with 0.7 mM MnCl$_2$ to allow the bound base to be incorporated. The manganese buffer was removed and the wells were then rinsed with 50 µl Buffer B with 1 mM CaCl$_2$. A next cycle of sequencing was then performed in an identical manner by replacing the calcium buffer in each well with the appropriate sequencing mix detailed above. Three consecutive rounds of cycle sequencing with calcium are demonstrated in FIG. 11. The first three incorporations should be "C" then "T" and then "G". The first and second round clearly distinguishes the correct bases demonstrating the principle of the technique. Rising background fluorescence confounds the third base read which presumable could be mitigated by more stringent washes between cycles or shorter cycle time by an automated procedure.

Figure 12:
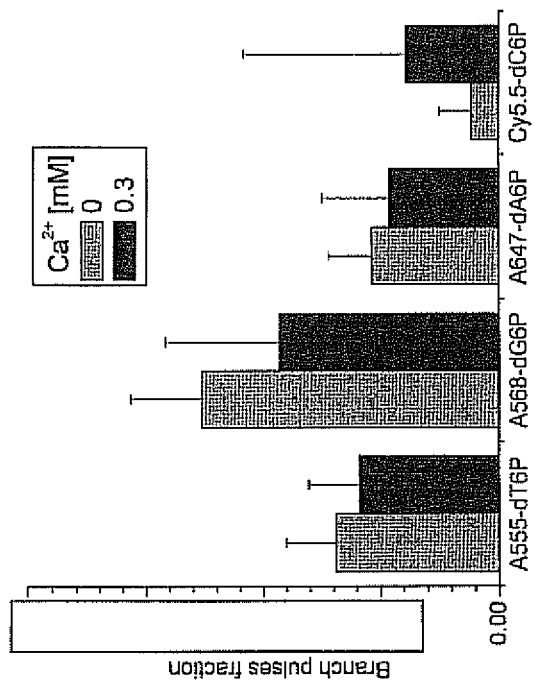
FIG. 12 shows the effect of the addition of $Ca^{2+}$ (0.3 mM) to a DNA sequencing reaction on the relative insertion or deletion errors for such process.
Figure 12:
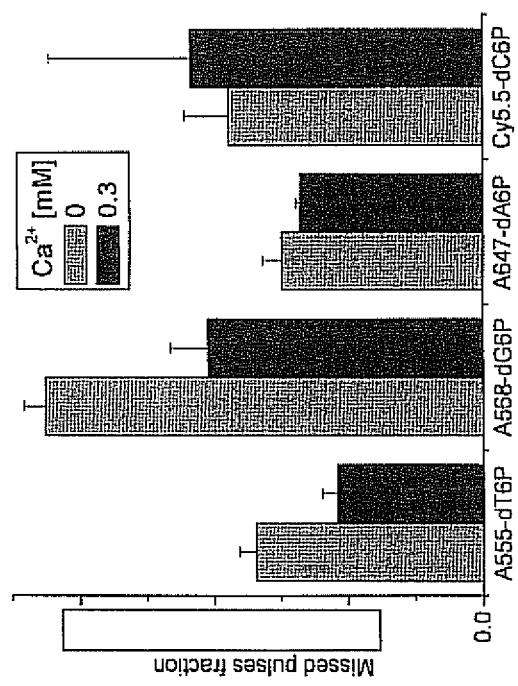

Error analysis was performed as a function of addition of 0.3 mM CaCl$_2$ to a single-molecule, real-time DNA sequencing reaction. The control sequencing reactions and error analysis were carried out as described in Eid, J. et al., Science, 323(5910), 133-138 (2009). For the 0.3 mM CaCl$_2$ condition, 0.3 mM CaCl$_2$ was included in the immobilization, wash and reaction buffers. Because the addition of CaCl$_2$ increases the nucleotide incorporation residence times, the errors caused by missed pulses is reduced, while extra pulses due to premature release events are unchanged within the error of the measurement. The results are plotted in FIG. 12 for each of the four types of bases. As can be seen, the error rates for insertion and deletions are reduced upon the inclusion of non-catalytic metals.

Example 3

Non-Catalytic Metal Cofactors—Inhibition of DNA Polymerase

The degree by which different metal cofactors can inhibit DNA polymerization by phi29 DNA pol was surveyed in the presence of a constant concentration of catalytic manganese metal cofactor (0.7 mM $MnCl_2$). DNA synthesis rate was measured using a real-time, steady-state DNA polymerization assay utilizing 4-MU derivitized nucleotides (4 methylumbelliferyl coumarin, M. Kozlov, V. Bergendahl, R. Burgess, A. Goldfarb, A. Mustaev, Anal. Biochem. 342, 206 (2005)). The assay utilizes rolling circle DNA polymerization on a primed 72 base circular single-stranded DNA template. Three of the deoxyribonucleotides (A, T, and G) are phospholinked with 4-MU. Incorporation of the derivatized nucleotides releases the non-fluorescent pentaphosphate 4-MU.

In a fast coupled reaction, Shrimp Alkaline Phosphatase (SAP) hydrolyzes the pendant phosphates creating the nascent fluorescent 7-hydroxyl methylumbelliferyl coumarin (Eid et al. Science. 2009 Jan. 2;323(5910):133-8). The increase in the fluorescent signal with time is proportional to the rate of DNA polymerization. Steady state polymerization reactions were carried out using 25 nM phi29 DNA polymerase mutant, 5 nM primed circular DNA template, 10 μM 4MU-dA6P, 4MU-dG6P, 4MU-dT6P, and 5 mM Alexa 555-dC6P in 50 mM ACES pH 7.1, 130 mM KOAc, 5 mM DTT, 0.7 mM $MnCl_2$, and 0.04 U/ul SAP. The fluorescence was monitored in plate format using a Beckman Paradigm fluorescence plate reader (excitation 360 nm, emission 465 nm).

Figure 13:
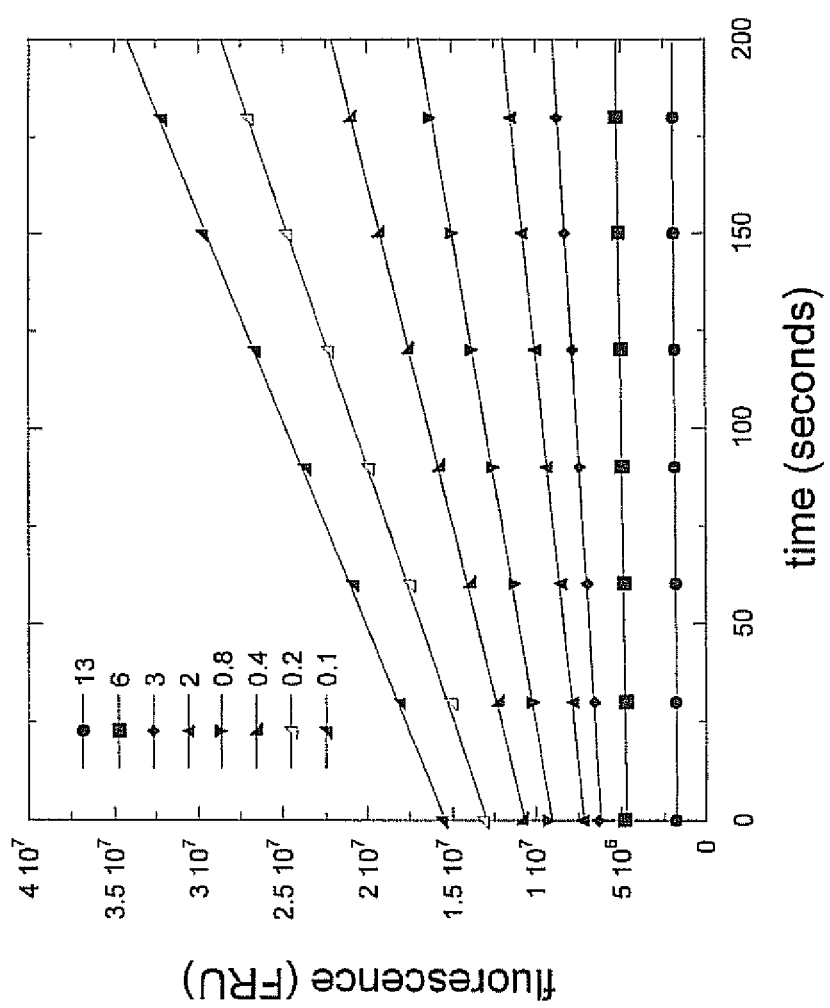
FIG. 13 shows data for fluorescence versus time for reactions at varying concentrations of added $ZnSO_4$.
Figure 14:
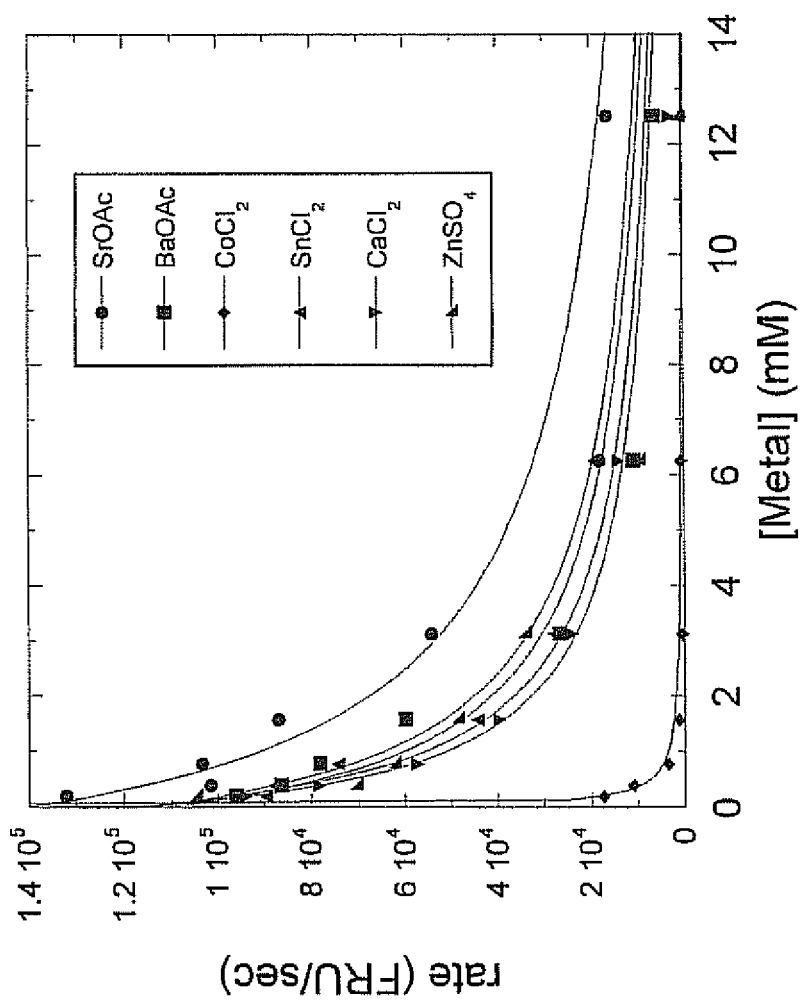
FIG. 14 shows polymerase reaction rate as a function of concentration for various non-catalytic metal cofactors.
Figure 15:
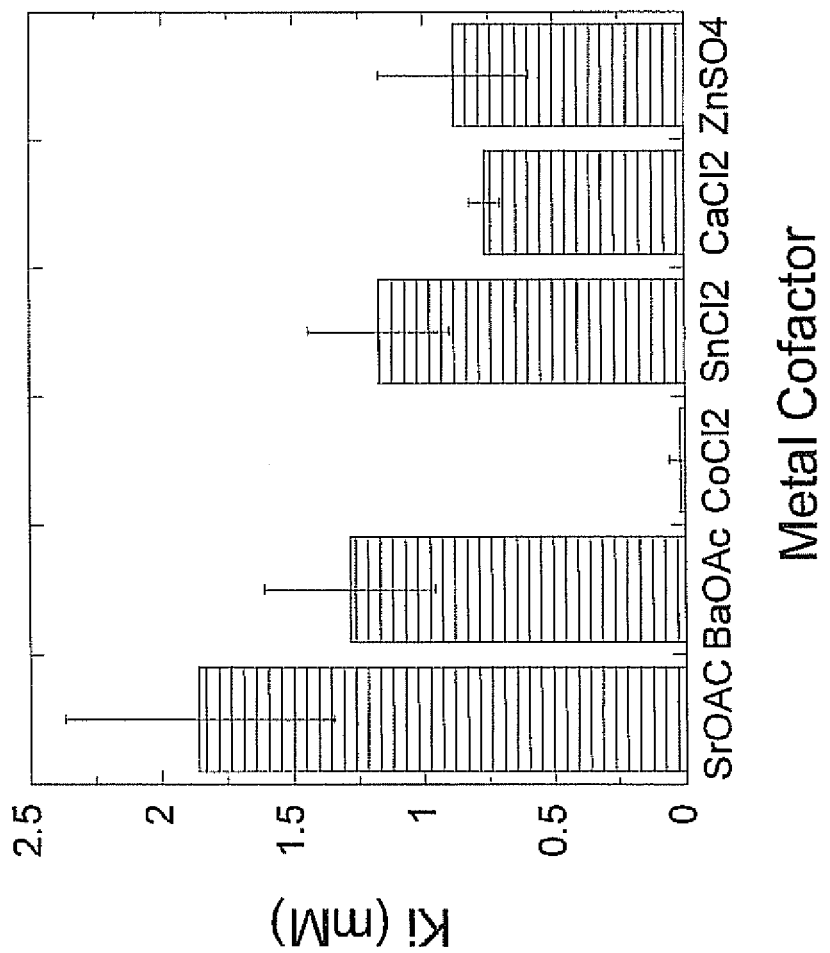
FIG. 15 shows the Ki values determined for various non-catalytic metal cofactors.

FIG. 13 shows the fluorescence plotted as a function of time at varying concentrations of added $ZnSO_4$. The slope (rate) of each time course was determined by fitting the data using linear regression. The rate is plotted as a function of the metal ion concentration in FIG. 14 along with a similar analysis performed for Sr, Ba, Co, Sn, and Ca. The degree of inhibition of polymerase activity can be compared by fitting the inhibition profiles using nonlinear regression to the equation:

$$\text{rate} = \text{rate}_0\left(1 - \frac{[\text{metal}]}{[\text{metal}] + K_i}\right)$$

where $\text{rate}_0$ is the rate of the reaction without additional metal added and Ki is the inhibition constant for a given metal ion. The inhibition constants are plotted in FIG. 15 where lower values of Ki indicate a greater degree of inhibition. Assays of this type can be used to identify potential non- or lower catalytic metal cofactors for phi29 DNA polymerase. Experiments performed using single metals can likewise be performed to identify metal that can support DNA polymerization (catalytic).

Example 4

Deuterium Addition

This example demonstrates the increase in mean pulse width for single molecule sequencing observed with the addition of deuterium in the form of $D_2O$. Experiments were conducted using a Single Molecule Real Time (SMRT™) 4 color sequencing technology instrument as described herein. A modified phi29 DNA polymerase having the mutations N62D/T368F/E375Y/K512Y and modified for streptavidin binding (polymerase R, 5 nM) was mixed with a circular template/primer complex (30 nM) as described in U.S. patent application Ser. No. 12/383,855, entitled "Method and Compositions for Nucleic Acid Sample Preparation" filed Mar. 27, 2009, and U.S. patent application Ser. No. 12/413,258, and other reagents (e.g. Ca2+ salt, 1 mM and A555-T nucleotide analog, 500 nM) in MOPS pH 7.4 buffer and kept above room temperature for at least 1 hr to form a polymerase R/template/primer complex. Then solution of the Polymerase R/template/primer complex was diluted by MOPS pH 7.4 buffer, an aliquot was added to the chip and kept at room temperature in high humidity chamber for least 15 min. The chip was then washed at least 5 times with ACES pH 7.1 buffer and a solution containing 4 fluorescently labeled analogs (A555-O-aminohexyl-dT6P(A555-T)—channel 1, A568-O-aminohexyl-dG6P (A568-G)—channel 2, A647-O-aminohexyl-dA6P (A647-A)—channel 3, and Cy5.5-NH$(CH_2)_5$C(O)NH $(CH_2)_6$O-dC6P-(Cy5.5-C)—channel 4)—all 500 nM) in ACES pH7.1 buffer was added to the chip. The chip was then placed inside the prototype sequencing instrument and sequencing reaction was started by adding another solution containing 4 fluorescently labeled analogs and Mn2+ (0.7 mM). Seven minute data movies were recorded for each condition and data was processed and analyzed. D2O (99.95+% isotopic purity) was purchased from Alfa Aesar and used as received. To obtain the final concentration on the chip, D2O was introduced into the concentrated ACES buffer and/or used as diluting agent instead of H2O.

Figure 16:
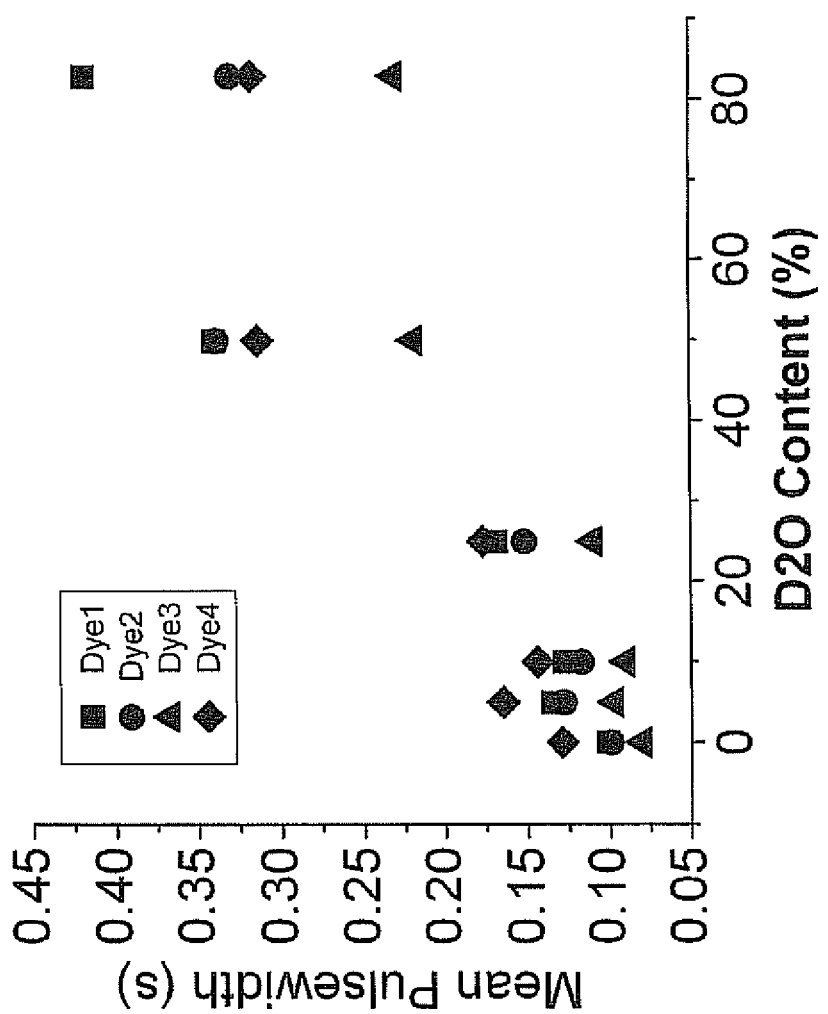
FIG. 16 shows data for the mean pulse width as a function of $D_2O$ content in single-molecule sequencing reactions.

FIG. 16 shows the mean pulse widths for each of the four dyes corresponding to the four nucleotides. It can be seen that for each of the four dyes, the mean pulse width increases with the addition of higher percentages of $D_2O$. It was determined that the yield at 25% $D_2O$ was comparable to the yield at 100% H2O, while the mean pulse width increased by a factor of about 1.5 for all of the nucleotide analogs tested.

Example 5

Solvent Additives

Experiments were conducted using a Single Molecule Real Time (SMRT™) 4-color sequencing instrument as described herein to collect the data. Polymerase R (5nM) was mixed with a circular template/primer complex (30 nM) as described in U.S. Patent Application Ser. No. 12/383,855, entitled "Method and Compositions for Nucleic Acid Sample Preparation" filed Mar. 27, 2009, and U.S. patent application Ser. No. 12/413,258 and other reagents (e.g. Ca2+ salt, 1 mM and A555-T analogs 500 nM) in MOPS pH 7.4 buffer and kept above room temperature for at least 1 hr to form a Polymerase R/template/primer complex. Then solution of the Polymerase R/template/primer complex was diluted 10 times by MOPS pH 7.4 buffer, an aliquot was added to the chip and kept at room temperature in high humidity chamber for least 15 min. The chip was then washed at least 5 times with 8 ACES pH 7.1 buffer and a solution containing 4 fluorescently labeled analogs (A555-T, A568-G, A647-A, Cy5.5-C—all 500nM) in ACES pH 7.1 buffer was added to the chip. The chip was then placed inside the prototype sequencing instrument and sequencing reaction was started by adding another solution containing 4 fluorescently labeled analogs and Mn2+ (0.7 mM). Seven minute data movies were recorded for each condition and data was processed and analyzed.

Solvents (dimethylacetamide (DMA—anhydrous, 99.8%), dimethylsulfoxide (DMSO—99.5%), ethanol (absolute), dioxane (anhydrous, 99.8%), tetrahydrofuran (THF—99.9%, Chromasolv grade)—all from Aldrich and methanol (HPLC grade, 99.8%), acetonitrile (HPLC grade, 99.8%), dimethylformamide (DMF—Drysolv grade, 99.8%)—all from EMD) were used as received. To obtain the final concentration, organic solvent additives were introduced into the concentrated buffers and/or used as diluting agents in place of water.

Figure 17:
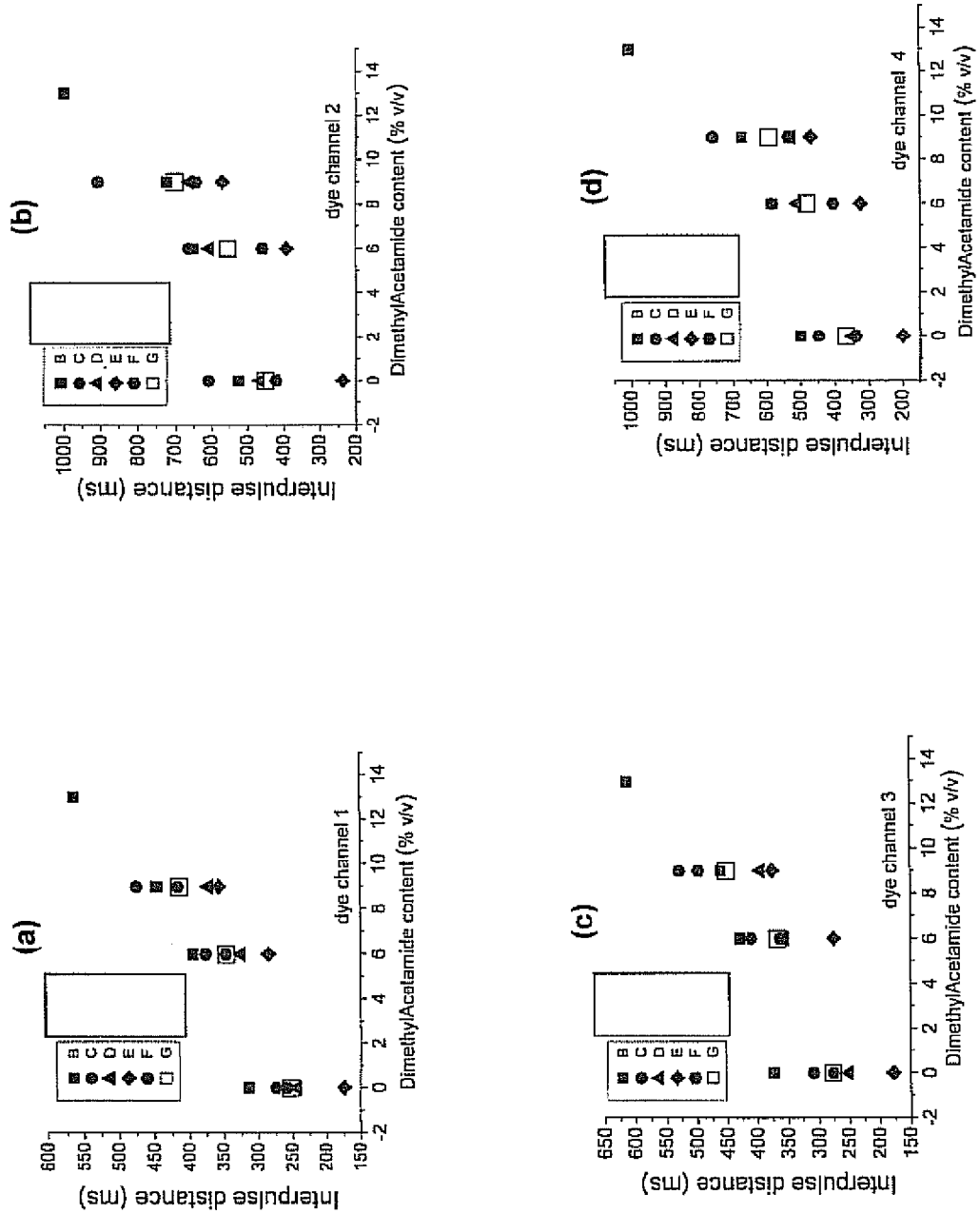
FIGS. 17 (a)-(d) shows data for the interpulse distance as a function of the amount of dimethylacetamide (DMA) in single-molecule sequencing reactions for 4 dye channels.

FIG. 17 shows the mean interpulse distance in milliseconds for each of the nucleotides for a single molecule sequencing reaction run with various concentrations of dimethylacetamide (DMA). The data for 5 separate experiments and the average for the 5 experiments is shown in the figure. It can be seen that as the concentration of DMA is increased, the interpulse distance also increases for all four of the nucleotides. The measured pulse widths showed very little change with the addition of DMA (no measurable change for channels 1-3 and a slight increase for channel 4).

Figure 18:
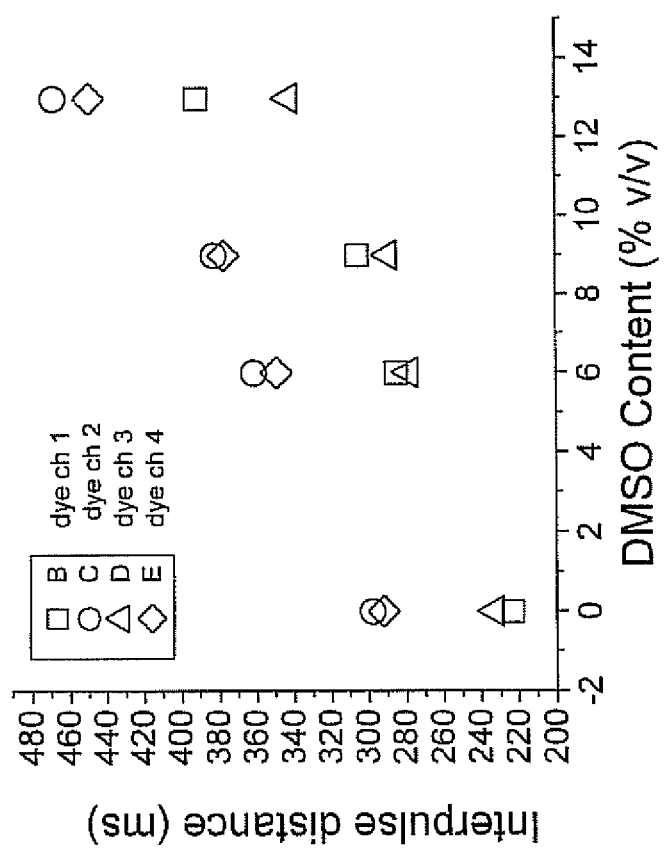
FIG. 18 shows data for the interpulse distance as a function of the amount of dimethylsulfoxide (DMSO) in single-molecule sequencing reactions for 4 dye channels.

FIG. 18 shows the mean interpulse distance in milliseconds for the each of the 4 dye channels for a single molecule sequencing reaction run with various concentrations of dimethysulfoxide (DMSO). The data show that as the DMSO concentration is increased, the interpulse distance also increases. The pulse widths increased on the addition of DMSO in channels 1, 2, and 4, and were unchanged in channel 3.

Example 6

Polymerase Systems Having Two Kinetically Observable Steps—Stopped Flow Measurements This experiment describes the observation of a polymerase system having two kinetically observable steps (two slow steps) where the two kinetically observable steps occur while the nucleotide is associated with the enzyme (after nucleotide binding and through product release. In the experiment described here, the two kinetically observable steps would correspond to steps occurring in the bright state of a single-molecule sequencing system using nucleotides having dyes attached to the terminal phosphate of the nucleotides.

For this assay we use a SF-2004 stopped flow instrument (Kintek Corp, Austin, Tex.) to monitor the fluorescence at 535 nm (using a band pass filter), to measure Alexa fluor 488 emission. The experimental design is the same as for example 2. The enzyme, DNA, buffer, potassium acetate, and dithiothreitol (DTT) are mixed in one sample and allowed to equilibrate. Alexa-555-dC6P (a terminally labeled hexaphosphate nucleotide substrate), buffer, potassium acetate, DTT, $MnCl_2$, and $CaCl_2$ are mixed in a second sample. The stopped flow instrument rapidly mixes these samples and reads the fluorescent signal at 535 nm as a function of time.

The binding of the nucleotide to the enzyme-DNA complex is often observed to occur as a single exponential decrease in the fluorescence signal, indicating a process with a single kinetically observable step. Where the steps of the polymerase reaction from after binding through release of the pentaphosphate-dye molecule are governed by a single rate-limiting step a single exponential increase in the fluorescent signal is expected. Thus, in the scenario where nucleotide binding and the subsequent steps through product release are each governed by single rate-limiting steps, we observe a fluorescent signal that is adequately described by a sum of two exponentials.

Figure 19:
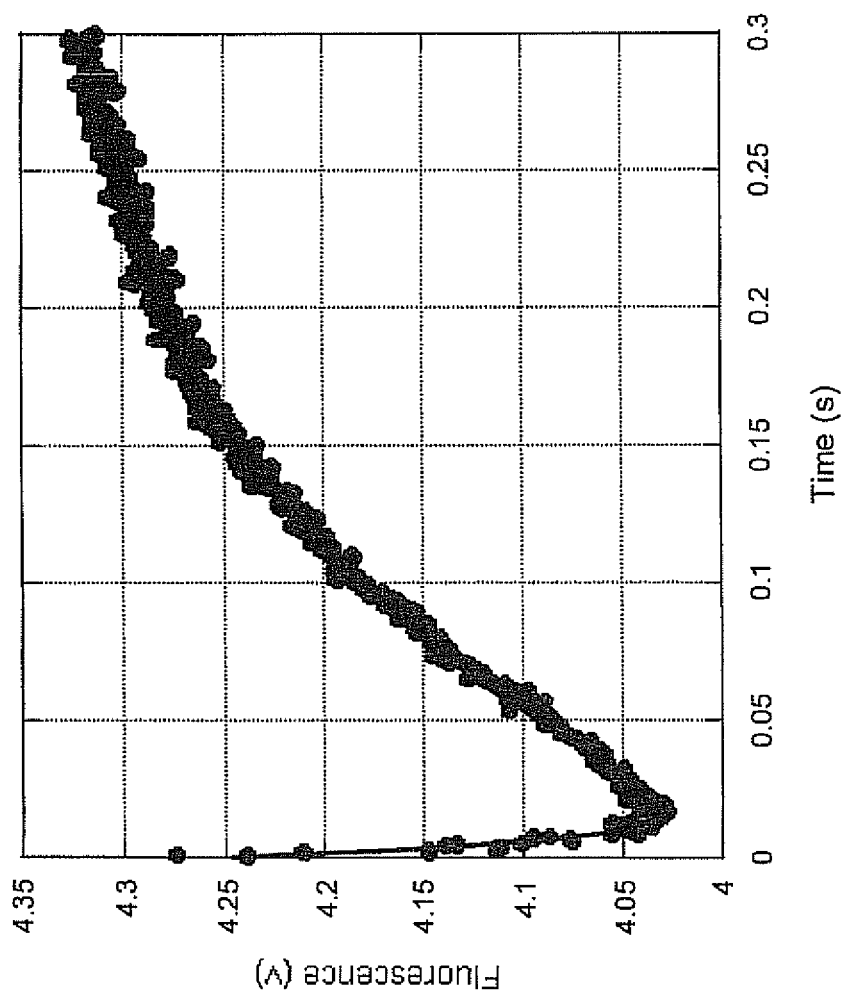
FIG. 19 shows the results of a stopped-flow experiment for a polymerase reaction system in which the decrease in the fluorescent signal fits to a single exponential and the increase in signal fits to a single exponential.

FIG. 19 shows the data from a polymerase reaction system in which the decrease in the fluorescent signal fits to a single exponential having an observed rate constant of $156\pm3$ $s^{-1}$, and the increase in signal fits to a single exponential having an observed rate constant of $8.5\pm0.1$ $s^{-1}$. FIG. 19 includes both the experimental data and the curve fits for single exponential decay and rise in fluorescence. The polymerase reaction shown in FIG. 19 involved the polymerase enzyme Polymerase R in 50 mM ACES buffer at a pH of 7.1. The assay was performed with the following components and amounts: 0.125 µM polymerase R enzyme, 0.025 µM DNA, 50 mM ACES, pH 7.1, 0.7 mM $MnCl_2$, 75 mM potassium acetate, 5 mM dithiothreitol, 3 µM alexa 555-dC6P. The observed fluorescent signal was fit to a sum of two exponentials, where the rate of the drop is $156\pm3$ $s^{-1}$, and the rate of the increase in signal is $8.5\pm0.1$ $s^{-1}$.

Figure 20:
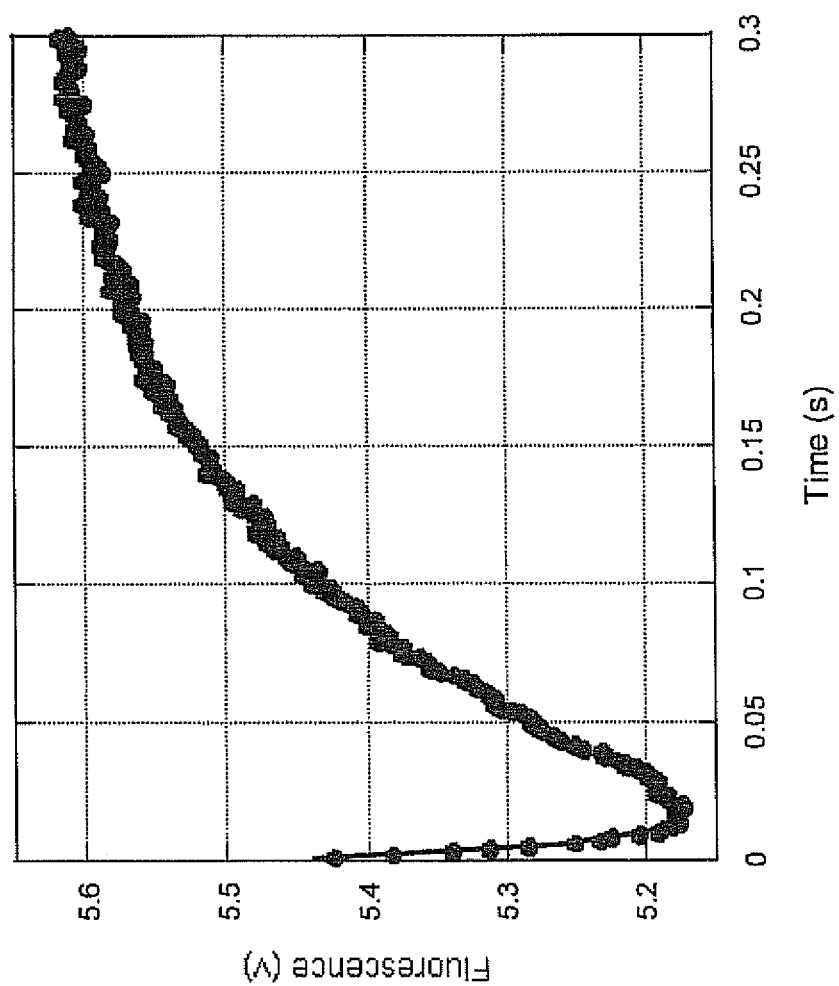
FIG. 20 shows the results of a stopped-flow experiment for a polymerase reaction system in which the decrease in the fluorescent signal fits to a single exponential and the increase in signal is best described by two exponentials.

FIG. 20 shows the data for a polymerase reaction system which exhibits two kinetically observable steps for the steps after nucleotide binding through product release. The polymerase reaction used the enzyme polymerase R in 50 mM Tris buffer, at pH 7.1, with 0.25 mM $CaCl_2$. The assay used 0.125 µM polymerase R enzyme, 0.025 µM DNA, 50 mM Tris, pH 7.1, 0.7 mM $MnCl_2$, 0.25 mM $CaCl_2$, 75 mM potassium acetate, 5 mM dithiothreitol, 3 µM alexa 555-dC6P. A good fit to the data could not be obtained with two exponentials. However, a good quality fit was obtained using the sum of three exponentials. The drop in fluorescence occurs with a single exponential having an observed rate constant of $172\pm12$ $s^{-1}$. The increase in fluorescence is best described as the sum of two exponentials, where the faster of the two steps occurs with an observed rate constant of $60\pm10$ $s^{-1}$, and the slower of the two steps occurs with an observed rate constant of $12.0\pm0.1$ $s^{-1}$. The behavior of this system is best described by two kinetically observable steps during the part of the polymerase reaction in which the nucleotide is associated with the enzyme. Each of the steps is partially rate-limiting. The observed fluorescent signal is fit to a sum of three exponentials, where the observed rate constant for the drop in fluorescence is $172\pm12$ $s^{-1}$, and the increase in fluorescence exhibits two kinetically observable rate constants, one at $60\pm10$ $s^{-1}$ and the other at $12.0\pm0.1$ $s^{-1}$.

Figure 21:
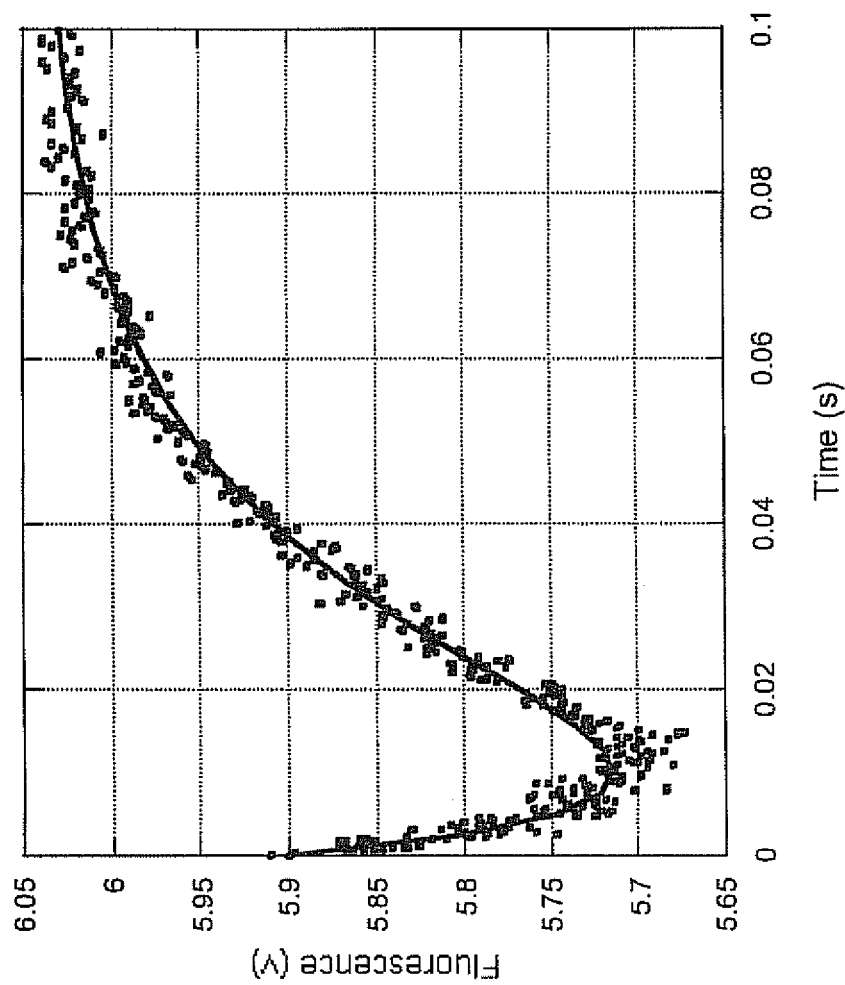
FIG. 21 shows the results of a stopped-flow experiment for a polymerase reaction system in which the decrease in the fluorescent signal fits to a single exponential and the increase in signal fits to a single exponential.

FIG. 21 shows stopped flow experimental data for a polymerase having a drop in fluorescence and a rise in fluorescence which each can be fit to a single exponential. FIG. 21 shows the incorporation of Alexa 555-dC6P by a phi29 DNA polymerase enzyme having the mutations N62D/T368F/E375Y/A484E/K512Y and modified for streptavidin binding (polymerase T) in 50 mM Tris buffer, pH 7.1. The assay used 0.125 µM polymerase T enzyme, 0.025 µM DNA, 50 mM Tris, pH 7.1, 0.7 mM MnCl2, 75 mM potassium acetate, 5 mM dithiothreitol, 3 µM alexa 555-dC6P. The observed fluorescent signal is fit to a sum of two exponentials, where the rate of the drop has an observed rate constant of $118\pm4$ $s^{-1}$, and the increase in the signal rate-limiting step occurs with an observed rate constant of $46\pm1$ $s^{-1}$.

Figure 22:
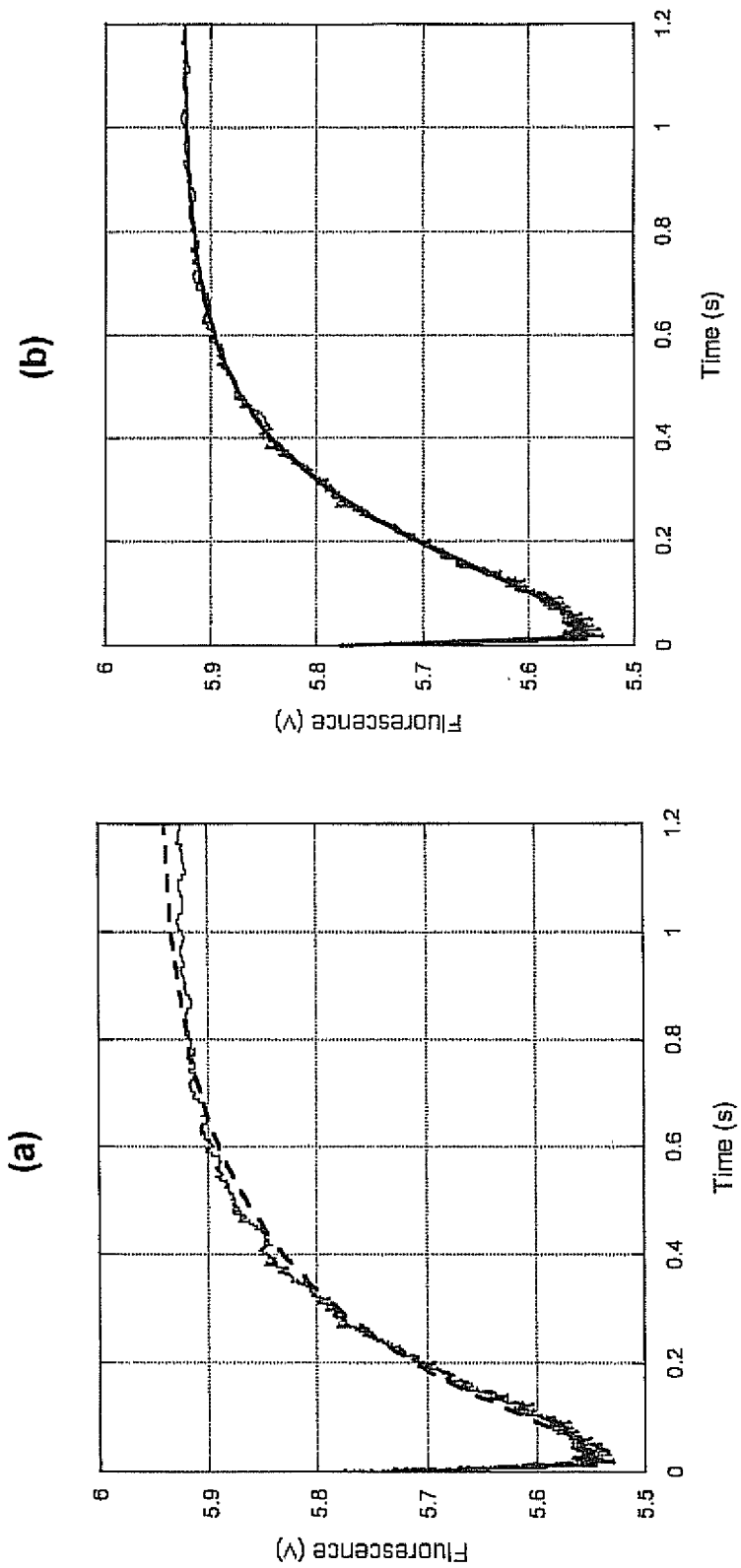
FIG. 22 shows the results of a stopped-flow experiment for a polymerase reaction system in which the decrease in the fluorescent signal fits to a single exponential and the increase in signal is best described by to two exponentials (22(b)), and is poorly fit by a single exponential (22(a)).

FIG. 22 illustrates how changing the polymerase reaction conditions can produce a polymerase reaction system which exhibits two kinetically observable rate-limiting steps for the steps after nucleotide binding through product release. In this case, we believe that specific enzyme mutations in the polymerase T enzyme, coupled with the presence of $Ca^{++}$ under the conditions of the polymerase reaction described results in additional mutations of the enzyme has changed the kinetic performance of the system to obtain a system in which there are two kinetically observable rate constants between nucleotide binding through product release with almost equal rate constants. FIG. 22 shows stopped flow data for the incorporation of Alexa 555-dC6P by polymerase enzyme polymerase T in 50 mM Tris buffer, pH 7.1, with 1.25 mM $CaCl_2$. The assay used 0.125 µM polymerase T enzyme, 0.025 µM DNA, 50 mM Tris, pH 7.1, 0.7 mM $MnCl_2$, 1.25 mM $CaCl_2$, 75 mM potassium acetate, 5 mM dithiothreitol, 3 µM alexa 555-dC6P. FIG. 22(a) shows an attempt to fit the data with two exponentials, one for the decay, and the other for the rise in fluorescence. It can be seen from FIG. 22(a) that the data is not well described in this manner. 22(b) shows the observed fluorescent signal fit to a sum of three exponentials where the rate constant for the drop in fluorescence is $157\pm5$ $s^{-1}$, and the increase in the signal exhibits two kinetically observable steps, where one step exhibits an observed rate constant of $9\pm2$ $s^{-1}$ and the other step exhibits a rate constant of $7\pm1$ $s^{-1}$. We note that the conditions that resulted in the two kinetically observable steps of FIG. 22(b) are the same as those for the experiment shown in FIG. 21, except for the presences of $CaCl_2$ at a concentration of 1.25 mM in this experiment, illustrating that a polymerase reaction exhibiting two slow steps can be produced by controlling the polymerase reaction conditions.

Example 7

Rapid Chemical Quench Experiment to Observe Two Kinetically Observable Steps for the Steps after Product Release Through Nucleotide Binding The presence of two kinetically observable steps after product release through nucleic acid binding can be observed by measuring the difference in the kinetics of single incorporation and multiple incorporations. First, a transient incorporation nucleotide incorporation assay (rapid chemical quench flow or stopped flow fluorescence) is run in order to determine the apparent rate constant for binding of a first nucleotide. Next, the experiment is run such that two nucleotides are incorporated. By comparing the kinetic parameters for the incorporation of two nucleotides as compared to those for incorporating one nucleotide, it can be determined whether there is an intervening step, such as translocation or isomerization which significantly limits the rate. Where such a step is identified, the pseudo first order rate constant of the nucleotide binding step can be lowered by lowering the concentration of nucleotide. In this manner, a system having two slow steps in the phase after product release and through nucleotide binding can be produced by matching the apparent rate constant of nucleotide binding with that the preceding isomerization or translocation event.

Example 8

Effect of L-Cysteine on Single Molecule Sequencing

Figure 24:
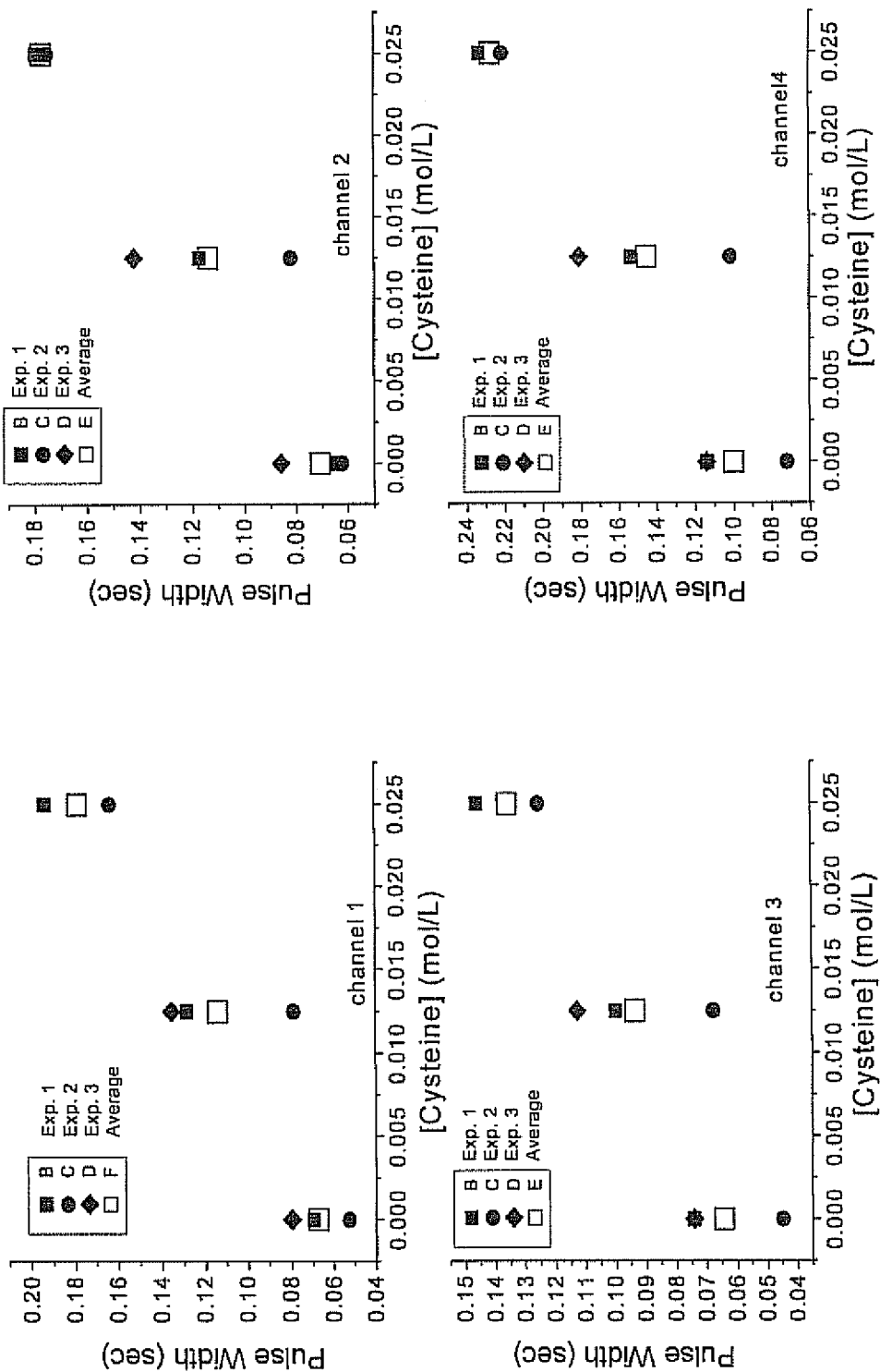
FIG. 24 shows data for the pulse width as a function of the amount of added cysteine to single molecule sequencing reactions for each of four dye channels.

Experiments were conducted using a Single Molecule Real Time (SMRT™) 4-color sequencing instrument as described above for solvent additives. L-Cysteine, Hydrochloride (99.6%) was purchased from Calbiochem and used as received. Cysteine solution was introduced in a solution of ACES buffer. FIG. 24 shows that the pulse width increases with increasing amounts of added cysteine to the sequencing reaction mixture. The effect is seen in all four nucleotide/dye channels. In addition to the increase in pulse width, the addition of cysteine led to increases in accuracy and in yield. When 0.25 mM cysteine was added, the overall yield increased 2.5 times, and accuracy was increased by 4.7%. over a control reaction having no added cysteine.

Example 9

High Throughput Screen for Polymerase Mutants with Slow Product Release

As described above, polymerases exhibiting slow release of polyphosphate product are of particular interest, e.g., in producing polymerases exhibiting two slow steps for use in single molecule sequencing. Screening polymerase mutants using a stopped-flow assay to determine kinetic parameters, however, can be time-consuming. A higher throughput format for identifying polymerase variants exhibiting slow product release has thus been developed.

In the screen, each candidate polymerase mutant is employed in a primer extension reaction using a DNA template (e.g., a circular DNA template) and four dNTPs or analogs, in the presence or absence of a competitive inhibitor. Nucleotide incorporation is measured based upon elongation rate of the polymerization reaction, as determined from the change in synthesis product size (e.g., as determined by agarose gel electrophoresis).

Suitable competitive inhibitors include, but are not limited to, Z-6-aminohexylpentaphosphate (Cbz-X-5P). Synthesis of Cbz-X-5P has been described in U.S. patent application Ser. No. 12/370,472, which also describes additional exemplary inhibitors. Without limitation to any particular mechanism, Cbz-X-5P mimics the polyphosphate reaction product and competes with dNTP binding, slowing primer extension. The assay is predicated on product affinity as an indication of slow product release; that is, mutants with slower product release are expected to have greater affinity for the competitive inhibitor and thus show a slower extension rate. Candidate mutants identified by the primer extension screen as potentially having decreased product release rates can be verified if desired, e.g., by stopped-flow measurements. The screen is optionally automated or partially automated.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

We claim:

1. A method of sequencing a nucleic acid, comprising:
providing a complex comprising a Phi-29 DNA polymerase enzyme, a template nucleic acid, and primer sequence complementary to at least a portion of the template nucleic acid;
contacting the complex with a reaction mixture that comprises a mixture of divalent metal ions comprising at least one catalytic metal ion and at least one non-catalytic metal ion, wherein the catalytic metal is selected from $Mg^{2+}$, $Mn^{2+}$ and mixtures thereof, and the non-catalytic metal is selected from $Ca^{2+}$, $Sr^{2+}$, or $Ba^{2+}$ and mixtures thereof, and one or more types of nucleotides or nucleotide analogs wherein a ratio of catalytic metal to non-catalytic metal in the reaction mixture is from about 10:1 to about 1:5;
detecting incorporation of one or more of the nucleotide into the complex; and
using the detected incorporation to determine the sequence of the template nucleic acid.

2. The method of claim 1, wherein the catalytic metal comprises $Mn^{2+}$ and the non-catalytic metal comprises $Ca^{2+}$.

3. The method of claim 1, wherein a ratio of catalytic metal to non-catalytic metal in the reaction mixture is from about 5:1 to about 1:1.

4. The method of claim 1, wherein a ratio of catalytic metal to non-catalytic metal in the reaction mixture is from about 2.5:1 to about 1.5:1.

5. The method of claim 1, wherein the catalytic metal and non-catalytic metal are present in the reaction mixture at a total concentration of from about 0.1 mM to about 10 mM.

6. The method of claim 1, wherein the detecting step comprises detecting incorporation of nucleotides in real-time as they are incorporated into the complex.

7. The method of claim 6, wherein the complex is immobilized on a solid support.

8. The method of claim 7, wherein the complex is immobilized on a solid support in an individually optically resolvable configuration.

9. A method of sequencing a nucleic acid, comprising:
providing a complex comprising a Phi-29 DNA polymerase enzyme, a template nucleic acid, and a primer sequence complementary to at least a portion of the template nucleic acid;
contacting the complex with a reaction mixture that comprises a plurality of types of nucleotides, and a mixture of divalent metal ions comprising at least one catalytic metal ion and at least one non-catalytic metal ion at first and second concentrations, respectively, wherein the catalytic metal is selected from Mg2+, Mn2+ and mixtures thereof, and the non-catalytic metal is selected from Ca2+, Sr2+, or Ba2+ and mixtures thereof wherein a ratio of catalytic metal to non-catalytic metal in the reaction mixture is from about 10:1 to about 1:5, wherein the mixture of divalent metal ions is selected to provide improved sequencing accuracy over a complex exposed to the first concentration of the catalytic metal in the absence of the non-catalytic metal;
detecting incorporation of a nucleotide into the complex; and
using the detected incorporation to determine the sequence of the template nucleic acid.

10. The method of claim 9 wherein the Phi-29 DNA polymerase enzyme comprises a modified recombinant Phi-29 DNA polymerase enzyme.

* * * * *

SEQUENCE LISTING

<160> NUMBER OF SEQ ID NOS: 2

<210> SEQ ID NO 1

-continued

```
<211> LENGTH: 34
<212> TYPE: DNA
<213> ORGANISM: Artificial Sequence
<220> FEATURE:
<223> OTHER INFORMATION: Synthesized

<400> SEQUENCE: 1
ggtgatgtag ataggtggta ggtggtgtca gatc                                34

<210> SEQ ID NO 2
<211> LENGTH: 54
<212> TYPE: DNA
<213> ORGANISM: Artificial Sequence
<220> FEATURE:
<223> OTHER INFORMATION: synthesized
<220> FEATURE:
<221> NAME/KEY: modified_base
<222> LOCATION: (25)..(25)
<220> FEATURE:
<221> NAME/KEY: misc_feature
<222> LOCATION: (25)..(25)
<223> OTHER INFORMATION: iAmMC6T

<400> SEQUENCE: 2
acgacgttga caataatacg gatcngacac cacctaccac ctatctacat cacc           54
```